US012558092B2

(12) United States Patent
Thompson et al.

(10) Patent No.: US 12,558,092 B2
(45) Date of Patent: **\*Feb. 24, 2026**

(54) END EFFECTORS, SURGICAL STAPLING DEVICES, AND METHODS OF USING SAME

(71) Applicant: Standard Bariatrics, Inc., Cincinnati, OH (US)

(72) Inventors: Jonathan Thompson, Cincinnati, OH (US); Bennie Thompson, Blue Ash, OH (US); Richard P. Nuchols, Williamsburg, OH (US); Russell L. Holscher, Maineville, OH (US)

(73) Assignee: Standard Bariatrics, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/125,976

(22) Filed: Mar. 24, 2023

(65) Prior Publication Data

US 2023/0233205 A1    Jul. 27, 2023

Related U.S. Application Data

(63) Continuation of application No. 17/005,050, filed on Aug. 27, 2020, now Pat. No. 11,717,295, which is a
(Continued)

(51) Int. Cl.
*A61B 17/00* (2006.01)
*A61B 17/072* (2006.01)
*A61B 17/29* (2006.01)

(52) U.S. Cl.
CPC .................. *A61B 17/07207* (2013.01); *A61B 2017/00477* (2013.01); *A61B 2017/00876* (2013.01);
(Continued)

(58) Field of Classification Search
CPC .... A61B 17/07207; A61B 2017/00477; A61B 2017/00876; A61B 2017/07214;
(Continued)

(56) References Cited

U.S. PATENT DOCUMENTS 770,871 A    9/1904   Slater
848,126 A    3/1907   Roosevelt
(Continued)

FOREIGN PATENT DOCUMENTS

AU    62460/00 A    4/2001
CA    2143247 A1    8/1995
(Continued)

OTHER PUBLICATIONS

National Instruments Corp.: Motion Control: FlexMotion -6C Hardware User Manual; Jul. 1999; 86 pages; United States of America.
(Continued)

*Primary Examiner* — Robert F Long
(74) *Attorney, Agent, or Firm* — BakerHostetler

(57)    ABSTRACT

An end effector for stapling and cutting an anatomical structure includes an anvil, a cartridge, and a blade. The anvil has an anvil face and a plurality of staple pockets positioned on the anvil face. The cartridge has a cartridge face defining a cartridge blade channel, the cartridge being configured to retain a plurality of staples. Each of the plurality of staples comprises a first staple leg, a second staple leg, and a crown connecting the first and second staple legs and having a midpoint. Each of the plurality of staples comprises an open staple configuration and a closed staple configuration where a first portion of the first staple leg and a second portion of the second staple leg are bent relative to the crown such that the first portion of the first staple leg and the second portion of the second staple leg cross the midpoint of the crown.

24 Claims, 42 Drawing Sheets

Related U.S. Application Data continuation of application No. 16/818,252, filed on Mar. 13, 2020, now abandoned, which is a continuation of application No. 16/538,480, filed on Aug. 12, 2019, now Pat. No. 10,624,638, which is a continuation of application No. 15/633,399, filed on Jun. 26, 2017, now Pat. No. 10,405,860, which is a continuation of application No. 15/129,366, filed as application No. PCT/US2015/022990 on Mar. 27, 2015, now Pat. No. 9,724,096.

(60) Provisional application No. 62/046,726, filed on Sep. 5, 2014, provisional application No. 61/972,274, filed on Mar. 29, 2014.

(52) U.S. Cl.
CPC ............... *A61B 2017/07214* (2013.01); *A61B 2017/07221* (2013.01); *A61B 2017/07235* (2013.01); *A61B 2017/07242* (2013.01); *A61B 2017/0725* (2013.01); *A61B 2017/07257* (2013.01); *A61B 2017/07271* (2013.01); *A61B 2017/07278* (2013.01); *A61B 2017/07285* (2013.01); *A61B 2017/2919* (2013.01); *A61B 2017/2927* (2013.01); *A61B 2017/2937* (2013.01); *A61B 2017/2939* (2013.01)

(58) Field of Classification Search
CPC ........... A61B 2017/07221; A61B 2017/07235; A61B 2017/07242; A61B 2017/0725; A61B 2017/07257; A61B 2017/07271; A61B 2017/07278; A61B 2017/07285; A61B 2017/2919; A61B 2017/2927; A61B 2017/2937; A61B 2017/2939
USPC ............ 227/175.1–182.1; 606/139, 142, 143
See application file for complete search history.

(56) References Cited

U.S. PATENT DOCUMENTS

| | | | |
|---|---|---|---|
| 1,413,896 A | | 4/1922 | Harold |
| 2,659,371 A | | 11/1953 | Schnee |
| 2,686,520 A | | 8/1954 | Jarvis |
| 3,017,637 A | | 1/1962 | Arnold |
| 3,050,578 A | | 8/1962 | Huebner |
| 3,490,675 A | | 1/1970 | Green |
| 3,551,987 A | | 1/1971 | Wilkinson |
| 3,877,434 A | | 4/1975 | Ferguson |
| 4,216,891 A | | 8/1980 | Behlke |
| 4,241,861 A | * | 12/1980 | Fleischer ............. A61B 17/072 |
| | | | 227/135 |
| 4,269,190 A | | 5/1981 | Behney |
| 4,289,133 A | | 9/1981 | Rothfuss |
| 4,319,576 A | | 3/1982 | Rothfuss |
| 4,354,628 A | | 10/1982 | Green |
| 4,442,964 A | | 4/1984 | Becht |
| 4,458,681 A | | 7/1984 | Hopkins |
| 4,494,057 A | | 1/1985 | Hotta |
| 4,520,817 A | | 6/1985 | Green |
| 4,526,174 A | * | 7/1985 | Froehlich ........... A61B 17/0684 |
| | | | 227/19 |
| 4,527,724 A | | 7/1985 | Chow |
| 4,558,699 A | | 12/1985 | Bashour |
| 4,566,620 A | | 1/1986 | Green |
| 4,589,582 A | | 5/1986 | Bilotti |
| 4,605,001 A | | 8/1986 | Rothfuss |
| 4,605,004 A | | 8/1986 | Di Giovanni |
| 4,608,981 A | | 9/1986 | Rothfuss |
| 4,610,383 A | | 9/1986 | Rothfuss |
| 4,617,928 A | | 10/1986 | Alfranca |
| 4,632,290 A | | 12/1986 | Green |
| 4,633,861 A | | 1/1987 | Chow |

| | | | |
|---|---|---|---|
| 4,676,774 A | | 6/1987 | Semm |
| 4,679,557 A | | 7/1987 | Opie |
| 4,705,038 A | | 11/1987 | Sjostrom |
| 4,784,137 A | | 11/1988 | Kulik |
| 4,803,985 A | | 2/1989 | Hill |
| 4,805,823 A | | 2/1989 | Rothfuss |
| 4,819,853 A | | 4/1989 | Green |
| 4,848,637 A | | 7/1989 | Pruitt |
| 4,930,503 A | | 6/1990 | Pruitt |
| 4,930,674 A | | 6/1990 | Barak |
| 4,935,006 A | | 6/1990 | Hasson |
| 4,941,623 A | | 7/1990 | Pruitt |
| 4,951,861 A | | 8/1990 | Schulze |
| 4,976,721 A | | 12/1990 | Blasnik |
| 4,978,049 A | | 12/1990 | Green |
| 5,040,715 A | | 8/1991 | Green |
| 5,136,220 A | | 8/1992 | Philipp |
| 5,152,744 A | | 10/1992 | Krause |
| 5,176,651 A | | 1/1993 | Allgood |
| 5,205,459 A | | 4/1993 | Brinkerhoff |
| 5,219,111 A | | 6/1993 | Bilotti |
| 5,221,036 A | | 6/1993 | Takase |
| 5,222,961 A | | 6/1993 | Nakao |
| 5,258,009 A | * | 11/1993 | Conners ................. A61L 31/06 |
| | | | 411/457 |
| 5,295,977 A | | 3/1994 | Cohen |
| 5,307,976 A | | 5/1994 | Olson |
| 5,308,576 A | | 5/1994 | Green |
| 5,312,410 A | | 5/1994 | Miller |
| 5,327,914 A | | 7/1994 | Shlain |
| 5,333,772 A | | 8/1994 | Rothfuss |
| 5,345,949 A | | 9/1994 | Shlain |
| 5,350,400 A | | 9/1994 | Esposito |
| 5,358,506 A | | 10/1994 | Green |
| 5,389,098 A | | 2/1995 | Tsuruta |
| 5,395,030 A | | 3/1995 | Kuramoto |
| 5,395,034 A | | 3/1995 | Allen |
| 5,411,481 A | * | 5/1995 | Allen ................. A61B 17/0469 |
| | | | 606/208 |
| 5,413,267 A | | 5/1995 | Solyntjes |
| 5,415,334 A | | 5/1995 | Williamson, IV |
| 5,431,323 A | | 7/1995 | Smith |
| 5,443,475 A | | 8/1995 | Auerbach |
| 5,452,836 A | | 9/1995 | Huitema |
| 5,452,837 A | | 9/1995 | Williamson, IV |
| 5,456,401 A | | 10/1995 | Green |
| 5,465,895 A | | 11/1995 | Knodel |
| 5,465,896 A | | 11/1995 | Allen |
| 5,469,840 A | | 11/1995 | Tanii |
| 5,470,006 A | | 11/1995 | Rodak |
| 5,470,009 A | | 11/1995 | Rodak |
| 5,480,089 A | * | 1/1996 | Blewett ................. A61B 17/072 |
| | | | 227/19 |
| 5,485,952 A | | 1/1996 | Fontayne |
| 5,487,500 A | | 1/1996 | Knodel |
| 5,496,333 A | | 3/1996 | Sackier |
| 5,503,638 A | | 4/1996 | Cooper |
| 5,507,426 A | | 4/1996 | Young |
| 5,507,773 A | | 4/1996 | Huitema |
| 5,514,098 A | | 5/1996 | Pfoslgraf |
| 5,531,744 A | | 7/1996 | Nardella |
| 5,535,935 A | * | 7/1996 | Vidal ............... A61B 17/07207 |
| | | | 227/176.1 |
| 5,549,621 A | | 8/1996 | Bessler |
| 5,551,622 A | | 9/1996 | Yoon |
| 5,554,169 A | | 9/1996 | Green |
| 5,560,530 A | | 10/1996 | Bolanos |
| 5,562,701 A | | 10/1996 | Huitema |
| 5,562,702 A | | 10/1996 | Huitema |
| 5,571,116 A | | 11/1996 | Bolanos |
| 5,571,131 A | | 11/1996 | Ek |
| 5,573,543 A | | 11/1996 | Akopov |
| 5,586,711 A | | 12/1996 | Plyley |
| 5,597,107 A | | 1/1997 | Knodel |
| 5,630,540 A | | 5/1997 | Blewett |
| 5,632,432 A | | 5/1997 | Schulze |
| 5,636,780 A | | 6/1997 | Green |
| 5,655,698 A | | 8/1997 | Yoon |
| 5,662,667 A | | 9/1997 | Knodel |

(56) References Cited

U.S. PATENT DOCUMENTS

| | | | |
|---|---|---|---|
| 5,676,674 A | 10/1997 | Bolanos | |
| 5,689,159 A | 11/1997 | Culp | |
| 5,697,542 A | 12/1997 | Knodel | |
| 5,702,409 A | 12/1997 | Rayburn | |
| 5,704,534 A | 1/1998 | Huitema | |
| 5,707,369 A | 1/1998 | Vaitekunas | |
| 5,732,871 A | 3/1998 | Clark | |
| 5,762,256 A | 6/1998 | Mastri | |
| 5,779,130 A | 7/1998 | Alesi | |
| 5,779,132 A | 7/1998 | Knodel | |
| 5,782,396 A | 7/1998 | Mastri | |
| 5,797,538 A | 8/1998 | Heaton | |
| 5,810,240 A | 9/1998 | Robertson | |
| 5,814,055 A | 9/1998 | Knodel | |
| 5,819,240 A | 10/1998 | Kara | |
| 5,820,009 A | 10/1998 | Melling | |
| 5,865,361 A | 2/1999 | Milliman | |
| 5,868,760 A | 2/1999 | McGuckin, Jr. | |
| 5,871,135 A | 2/1999 | Williamson IV | |
| 5,893,863 A | 4/1999 | Yoon | |
| 5,897,562 A * | 4/1999 | Bolanos | A61B 17/07207 |
| | | | 227/176.1 |
| 5,901,895 A | 5/1999 | Heaton | |
| 5,902,312 A | 5/1999 | Frater | |
| 5,954,259 A | 9/1999 | Viola | |
| 5,964,394 A | 10/1999 | Robertson | |
| 5,980,248 A | 11/1999 | Kusakabe | |
| 5,988,479 A | 11/1999 | Palmer | |
| 6,032,849 A | 3/2000 | Mastri | |
| 6,032,965 A | 3/2000 | Sabounjian | |
| 6,048,330 A | 4/2000 | Atala | |
| 6,099,551 A | 8/2000 | Gabbay | |
| 6,264,087 B1 | 7/2001 | Whitman | |
| 6,270,507 B1 | 8/2001 | Callicrate | |
| 6,315,184 B1 | 11/2001 | Whitman | |
| 6,325,810 B1 | 12/2001 | Hamilton | |
| 6,345,754 B1 | 2/2002 | Jeng | |
| 6,439,541 B1 | 8/2002 | Nosel | |
| 6,488,196 B1 | 12/2002 | Fenton, Jr. | |
| 6,505,768 B2 | 1/2003 | Whitman | |
| 6,511,490 B2 | 1/2003 | Robert | |
| 6,616,446 B1 | 9/2003 | Schmid | |
| 6,716,233 B1 | 4/2004 | Whitman | |
| 6,769,590 B2 | 8/2004 | Vresh | |
| 6,793,652 B1 | 9/2004 | Whitman | |
| 6,835,199 B2 | 12/2004 | McGuckin, Jr. | |
| RE38,708 E | 3/2005 | Bolanos | |
| 6,953,138 B1 * | 10/2005 | Dworak | A61B 17/07207 |
| | | | 227/181.1 |
| 6,978,921 B2 | 12/2005 | Shelton, IV | |
| 6,986,451 B1 | 1/2006 | Mastri | |
| 6,988,649 B2 | 1/2006 | Shelton, IV | |
| 7,025,791 B2 | 4/2006 | Levine | |
| 7,032,799 B2 | 4/2006 | Viola | |
| 7,037,344 B2 | 5/2006 | Kagan | |
| 7,044,353 B2 | 5/2006 | Mastri | |
| 7,070,083 B2 | 7/2006 | Jankowski | |
| 7,128,253 B2 | 10/2006 | Mastri | |
| 7,134,587 B2 | 11/2006 | Schwemberger | |
| 7,175,648 B2 | 2/2007 | Nakao | |
| 7,207,472 B2 | 4/2007 | Wukusick | |
| 7,225,964 B2 | 6/2007 | Mastri | |
| 7,229,428 B2 | 6/2007 | Gannoe | |
| 7,235,089 B1 | 6/2007 | McGuckin, Jr. | |
| 7,258,262 B2 | 8/2007 | Mastri | |
| 7,278,562 B2 | 10/2007 | Mastri | |
| 7,278,563 B1 | 10/2007 | Green | |
| 7,288,100 B2 | 10/2007 | Molina Trigueros | |
| 7,308,998 B2 | 12/2007 | Mastri | |
| RE40,237 E | 4/2008 | Bilotti | |
| 7,398,908 B2 | 7/2008 | Holsten | |
| 7,401,721 B2 | 7/2008 | Holsten | |
| 7,404,508 B2 | 7/2008 | Smith | |
| 7,407,075 B2 | 8/2008 | Holsten | |
| 7,407,076 B2 | 8/2008 | Racenet | |
| 7,407,077 B2 | 8/2008 | Ortiz | |
| 7,422,138 B2 | 9/2008 | Bilotti | |
| 7,434,716 B2 | 10/2008 | Viola | |
| 7,434,717 B2 | 10/2008 | Shelton, IV | |
| 7,438,209 B1 | 10/2008 | Hess | |
| 7,455,676 B2 | 11/2008 | Holsten | |
| 7,467,740 B2 | 12/2008 | Shelton, IV | |
| 7,472,815 B2 | 1/2009 | Shelton, IV | |
| 7,481,349 B2 | 1/2009 | Holsten | |
| 7,500,979 B2 | 3/2009 | Hueil | |
| 7,506,791 B2 | 3/2009 | Omaits | |
| 7,510,107 B2 | 3/2009 | Timm | |
| 7,549,564 B2 | 6/2009 | Boudreaux | |
| 7,549,654 B2 | 6/2009 | Anderson | |
| 7,565,993 B2 | 7/2009 | Milliman | |
| 7,588,175 B2 | 9/2009 | Timm | |
| 7,588,176 B2 | 9/2009 | Timm | |
| 7,588,177 B2 | 9/2009 | Racenet | |
| 7,604,151 B2 | 10/2009 | Hess | |
| 7,617,961 B2 | 11/2009 | Viola | |
| 7,635,074 B2 | 12/2009 | Olson | |
| 7,641,091 B2 | 1/2010 | Olson | |
| 7,645,285 B2 | 1/2010 | Cosgrove | |
| 7,658,312 B2 | 2/2010 | Vidal | |
| 7,665,647 B2 | 2/2010 | Shelton, IV | |
| 7,669,746 B2 | 3/2010 | Shelton, IV | |
| 7,669,747 B2 | 3/2010 | Weisenburgh | |
| 7,673,781 B2 | 3/2010 | Swayze | |
| 7,673,782 B2 | 3/2010 | Hess | |
| 7,690,547 B2 | 4/2010 | Racenet | |
| 7,694,864 B2 | 4/2010 | Okada | |
| 7,704,264 B2 | 4/2010 | Ewers | |
| 7,708,684 B2 | 5/2010 | Demarais | |
| 7,717,312 B2 | 5/2010 | Beetel | |
| 7,726,537 B2 | 6/2010 | Olson | |
| 7,726,538 B2 | 6/2010 | Holsten | |
| 7,726,539 B2 | 6/2010 | Holsten | |
| 7,731,072 B2 | 6/2010 | Timm | |
| 7,735,703 B2 | 6/2010 | Morgan | |
| 7,744,613 B2 | 6/2010 | Ewers | |
| 7,758,493 B2 | 7/2010 | Gingras | |
| 7,770,774 B2 | 8/2010 | Mastri | |
| 7,775,967 B2 | 8/2010 | Gertner | |
| D624,182 S | 9/2010 | Thouement | |
| 7,793,812 B2 | 9/2010 | Moore | |
| 7,794,475 B2 | 9/2010 | Hess | |
| 7,815,092 B2 | 10/2010 | Whitman | |
| 7,819,896 B2 | 10/2010 | Racenet | |
| 7,828,188 B2 | 11/2010 | Jankowski | |
| 7,837,079 B2 | 11/2010 | Holsten | |
| 7,846,149 B2 | 12/2010 | Jankowski | |
| 7,857,184 B2 | 12/2010 | Viola | |
| 7,866,525 B2 | 1/2011 | Scirica | |
| 7,866,528 B2 | 1/2011 | Olson | |
| 7,871,416 B2 * | 1/2011 | Phillips | A61B 17/122 |
| | | | 606/151 |
| 7,891,531 B1 | 2/2011 | Ward | |
| 7,891,533 B2 | 2/2011 | Green | |
| 7,913,893 B2 | 3/2011 | Mastri | |
| 7,918,869 B2 | 4/2011 | Saadat | |
| 7,918,873 B2 * | 4/2011 | Cummins | A61B 17/0644 |
| | | | 606/219 |
| 7,934,630 B2 | 5/2011 | Shelton, IV | |
| 7,955,340 B2 | 6/2011 | Michlitsch | |
| 7,959,050 B2 | 6/2011 | Smith | |
| 7,963,907 B2 | 6/2011 | Gertner | |
| 7,966,799 B2 | 6/2011 | Morgan | |
| 7,992,757 B2 | 8/2011 | Wheeler | |
| 7,997,469 B2 | 8/2011 | Olson | |
| 8,016,176 B2 | 9/2011 | Kasvikis | |
| 8,020,741 B2 | 9/2011 | Cole | |
| 8,028,884 B2 | 10/2011 | Sniffin | |
| 8,033,442 B2 | 10/2011 | Racenet | |
| 8,034,077 B2 | 10/2011 | Smith | |
| 8,052,697 B2 | 11/2011 | Phillips | |
| 8,056,788 B2 | 11/2011 | Mastri | |
| 8,061,577 B2 | 11/2011 | Racenet | |
| 8,062,236 B2 | 11/2011 | Soltz | |
| 8,066,168 B2 | 11/2011 | Vidal | |

(56) References Cited

U.S. PATENT DOCUMENTS

| | | | |
|---|---|---|---|
| 8,070,034 B1 | 12/2011 | Knodel |
| 8,070,036 B1 | 12/2011 | Knodel |
| 8,087,563 B2 | 1/2012 | Milliman |
| 8,091,756 B2 | 1/2012 | Viola |
| 8,096,459 B2 | 1/2012 | Ortiz |
| 8,113,406 B2 | 2/2012 | Holsten |
| 8,132,704 B2 | 3/2012 | Whitman |
| 8,141,762 B2 | 3/2012 | Bedi |
| 8,147,506 B2 | 4/2012 | Ortiz |
| 8,167,186 B2 | 5/2012 | Racenet |
| 8,172,122 B2 | 5/2012 | Kasvikis |
| 8,186,560 B2 | 5/2012 | Hess |
| 8,196,795 B2 | 6/2012 | Moore |
| 8,205,780 B2 | 6/2012 | Sorrentino |
| 8,210,415 B2 | 7/2012 | Ward |
| 8,216,159 B1 | 7/2012 | Leiboff |
| 8,220,690 B2 | 7/2012 | Hess |
| 8,226,602 B2 | 7/2012 | Quijana |
| 8,245,898 B2 | 8/2012 | Smith |
| 8,252,009 B2 | 8/2012 | Weller |
| 8,256,655 B2 | 9/2012 | Sniffin |
| 8,267,849 B2 | 9/2012 | Wazer |
| 8,276,801 B2 | 10/2012 | Zemlok |
| 8,276,802 B2 | 10/2012 | Kostrzewski |
| 8,292,153 B2 | 10/2012 | Jankowski |
| 8,308,725 B2 | 11/2012 | Bell |
| 8,317,070 B2 | 11/2012 | Hueil |
| 8,322,455 B2 | 12/2012 | Shelton, IV |
| 8,328,061 B2 | 12/2012 | Kasvikis |
| 8,328,064 B2 | 12/2012 | Racenet |
| 8,343,175 B2 | 1/2013 | Ewers |
| 8,348,127 B2 | 1/2013 | Marczyk |
| 8,348,129 B2 | 1/2013 | Bedi |
| 8,348,130 B2 | 1/2013 | Shah |
| 8,348,131 B2 | 1/2013 | Omaits |
| 8,353,436 B2 | 1/2013 | Kasvikis |
| 8,360,297 B2 | 1/2013 | Shelton, IV |
| 8,365,973 B1 | 2/2013 | White |
| 8,365,976 B2 | 2/2013 | Hess |
| 8,371,491 B2 | 2/2013 | Huitema |
| 8,382,775 B1 | 2/2013 | Bender |
| 8,393,513 B2 | 3/2013 | Jankowski |
| 8,393,514 B2 | 3/2013 | Shelton, IV |
| 8,403,197 B2 | 3/2013 | Vidal |
| 8,403,956 B1 | 3/2013 | Thompson |
| 8,408,442 B2 | 4/2013 | Racenet |
| 8,424,739 B2 | 4/2013 | Racenet |
| 8,439,244 B2 | 5/2013 | Holcomb |
| 8,439,246 B1 | 5/2013 | Knodel |
| 8,449,460 B2 | 5/2013 | Duke |
| 8,449,560 B2 | 5/2013 | Roth |
| 8,453,906 B2 | 6/2013 | Huang |
| 8,453,912 B2 | 6/2013 | Mastri |
| 8,453,913 B2 | 6/2013 | Milliman |
| 8,453,914 B2 | 6/2013 | Laurent |
| 8,464,923 B2 | 6/2013 | Shelton, IV |
| 8,465,507 B2 | 6/2013 | Cosgrove |
| 8,469,252 B2 | 6/2013 | Holcomb |
| 8,469,977 B2 | 6/2013 | Balbierz |
| 8,479,969 B2 | 7/2013 | Shelton, IV |
| 8,485,412 B2 | 7/2013 | Shelton, IV |
| 8,496,155 B2 | 7/2013 | Knodel |
| 8,496,156 B2 | 7/2013 | Sniffin |
| 8,499,993 B2 | 8/2013 | Shelton, IV |
| 8,523,041 B2 | 9/2013 | Ishitsuki |
| 8,529,585 B2 | 9/2013 | Jacobs |
| 8,540,128 B2 | 9/2013 | Shelton, IV |
| 8,540,130 B2 | 9/2013 | Moore |
| 8,544,712 B2 | 10/2013 | Jankowski |
| 8,561,872 B2 | 10/2013 | Wheeler |
| 8,573,465 B2 | 11/2013 | Shelton, IV |
| 8,574,243 B2 | 11/2013 | Saadat |
| 8,579,176 B2 | 11/2013 | Smith |
| 8,579,178 B2 | 11/2013 | Holsten |
| 8,590,762 B2 | 11/2013 | Hess |
| 8,596,513 B2 | 12/2013 | Olson |
| 8,608,043 B2 | 12/2013 | Scirica |
| 8,608,046 B2 | 12/2013 | Laurent |
| 8,613,384 B2 | 12/2013 | Pastorelli |
| 8,616,427 B2 | 12/2013 | Viola |
| 8,616,431 B2 | 12/2013 | Timm |
| 8,617,185 B2 | 12/2013 | Bonutti |
| 8,628,544 B2 | 1/2014 | Farascioni |
| 8,628,547 B2 | 1/2014 | Weller |
| 8,647,350 B2 | 2/2014 | Mohan |
| 8,663,245 B2 | 3/2014 | Francischelli |
| 8,668,130 B2 | 3/2014 | Hess |
| 8,672,208 B2 | 3/2014 | Hess |
| 8,672,830 B2 | 3/2014 | Dlugos, Jr. |
| 8,684,253 B2 | 4/2014 | Giordano |
| 8,701,958 B2 | 4/2014 | Shelton, IV |
| 8,714,429 B2 | 5/2014 | Demmy |
| 8,720,766 B2 | 5/2014 | Hess |
| 8,727,197 B2 | 5/2014 | Hess |
| 8,727,199 B2 | 5/2014 | Wenchell |
| 8,733,613 B2 | 5/2014 | Huitema |
| 8,740,035 B2 | 6/2014 | Mastri |
| 8,758,392 B2 | 6/2014 | Crainich |
| 8,763,875 B2 | 7/2014 | Morgan |
| 8,800,838 B2 | 8/2014 | Shelton, IV |
| 8,800,840 B2 | 8/2014 | Jankowski |
| 8,801,732 B2 | 8/2014 | Harris |
| 8,808,161 B2 | 8/2014 | Gregg |
| 8,808,325 B2 | 8/2014 | Hess |
| 8,827,136 B2 | 9/2014 | Hessler |
| 8,840,004 B2 | 9/2014 | Holsten |
| 8,852,218 B2 * | 10/2014 | Hughett, Sr. .... A61B 17/12022 606/157 |
| 8,864,009 B2 | 10/2014 | Shelton, IV |
| 8,882,766 B2 | 11/2014 | Couture |
| 8,899,465 B2 | 12/2014 | Shelton, IV |
| 8,925,788 B2 | 1/2015 | Hess |
| 8,945,163 B2 | 2/2015 | Voegele |
| 8,956,390 B2 | 2/2015 | Shah |
| 8,973,804 B2 | 3/2015 | Hess |
| 8,978,956 B2 | 3/2015 | Schall |
| 8,991,676 B2 | 3/2015 | Hess |
| 8,991,677 B2 | 3/2015 | Moore |
| 8,998,058 B2 | 4/2015 | Moore |
| 8,998,061 B2 | 4/2015 | Williams |
| 9,011,437 B2 | 4/2015 | Woodruff |
| 9,016,541 B2 | 4/2015 | Viola |
| 9,028,511 B2 | 5/2015 | Weller |
| 9,033,203 B2 | 5/2015 | Woodard, Jr. |
| 9,050,084 B2 | 6/2015 | Schmid |
| 9,066,721 B2 | 6/2015 | Ichihara |
| 9,084,600 B1 | 7/2015 | Knodel |
| 9,084,601 B2 | 7/2015 | Moore |
| 9,095,339 B2 | 8/2015 | Moore |
| 9,113,862 B2 | 8/2015 | Morgan |
| 9,113,868 B2 | 8/2015 | Felder |
| 9,119,627 B2 | 9/2015 | Cosgrove |
| 9,138,226 B2 | 9/2015 | Racenet |
| 9,149,325 B2 | 10/2015 | Worrell |
| 9,155,528 B2 | 10/2015 | Bender |
| 9,168,039 B1 | 10/2015 | Knodel |
| 9,179,911 B2 | 11/2015 | Morgan |
| 9,180,035 B2 | 11/2015 | Stack |
| 9,211,120 B2 | 12/2015 | Scheib |
| 9,216,019 B2 | 12/2015 | Schmid |
| 9,254,131 B2 | 2/2016 | Soltz |
| 9,289,206 B2 | 3/2016 | Hess |
| 9,289,207 B2 | 3/2016 | Shelton, IV |
| 9,307,981 B2 | 4/2016 | Mikkaichi |
| 9,314,362 B2 | 4/2016 | Bender |
| 9,326,768 B2 | 5/2016 | Shelton, IV |
| 9,339,442 B2 | 5/2016 | Tai |
| 9,345,478 B2 | 5/2016 | Knodel |
| 9,364,225 B2 | 6/2016 | Sniffin |
| 9,370,362 B2 | 6/2016 | Petty |
| 9,398,917 B2 | 7/2016 | Whitfield |
| 9,408,604 B2 | 8/2016 | Shelton, IV |
| 9,433,411 B2 | 9/2016 | Racenet |
| 9,439,541 B2 | 9/2016 | Ito |

(56) References Cited

U.S. PATENT DOCUMENTS

| | | | |
|---|---|---|---|
| 9,439,633 B2 | 9/2016 | John | |
| 9,498,219 B2 | 11/2016 | Moore | |
| 9,549,733 B2 | 1/2017 | Knodel | |
| 9,561,032 B2 | 2/2017 | Shelton, IV | |
| 9,603,595 B2 | 3/2017 | Shelton, IV | |
| 9,603,598 B2 | 3/2017 | Shelton, IV | |
| 9,615,952 B2 | 4/2017 | Scott | |
| 9,636,114 B2 | 5/2017 | Cole | |
| 9,675,355 B2 | 6/2017 | Shelton, IV | |
| 9,687,233 B2 | 6/2017 | Fernandez | |
| 9,687,237 B2 | 6/2017 | Schmid | |
| 9,693,816 B2 | 7/2017 | Orszulak | |
| 9,700,321 B2 | 7/2017 | Shelton, IV | |
| 9,706,991 B2 | 7/2017 | Hess | |
| 9,724,091 B2 | 8/2017 | Shelton, IV | |
| 9,724,093 B2 | 8/2017 | Farascioni | |
| 9,724,096 B2 | 8/2017 | Thompson | |
| 9,730,692 B2 | 8/2017 | Shelton, IV | |
| 9,775,613 B2 | 10/2017 | Shelton, IV | |
| 9,795,380 B2 | 10/2017 | Shelton, IV | |
| 9,801,627 B2 | 10/2017 | Harris | |
| 9,801,628 B2 | 10/2017 | Harris | |
| 9,801,630 B2 | 10/2017 | Harris | |
| 9,808,246 B2 | 11/2017 | Shelton, IV | |
| 9,808,257 B2 | 11/2017 | Armenteros | |
| 9,820,742 B2 | 11/2017 | Covach | |
| 9,827,002 B2 | 11/2017 | Hausen | |
| 9,844,370 B2 | 12/2017 | Viola | |
| 9,848,873 B2 | 12/2017 | Shelton, IV | |
| 9,848,875 B2 | 12/2017 | Aronhalt | |
| 9,848,878 B2 | 12/2017 | Racenet | |
| 9,855,040 B2 | 1/2018 | Kostrzewski | |
| 9,861,366 B2 | 1/2018 | Aranyi | |
| 9,872,682 B2 | 1/2018 | Hess | |
| 9,901,344 B2 | 2/2018 | Moore | |
| 9,901,346 B2 | 2/2018 | Moore | |
| 9,913,646 B2 | 3/2018 | Shelton, IV | |
| 9,924,947 B2 | 3/2018 | Shelton, IV | |
| 9,936,953 B2 | 4/2018 | Thompson | |
| 9,936,954 B2 | 4/2018 | Shelton, IV | |
| 9,937,001 B2 | 4/2018 | Nakamura | |
| 9,980,729 B2 | 5/2018 | Moore | |
| 9,999,426 B2 | 6/2018 | Moore | |
| 9,999,431 B2 | 6/2018 | Shelton, IV | |
| 10,004,505 B2 | 6/2018 | Moore | |
| 10,045,780 B2 | 8/2018 | Adams | |
| 10,085,751 B2 | 10/2018 | Overmyer | |
| 10,085,754 B2 | 10/2018 | Sniffin | |
| 10,130,360 B2 | 11/2018 | Olson | |
| 10,130,363 B2 | 11/2018 | Huitema | |
| 10,172,616 B2 | 1/2019 | Murray | |
| 10,194,912 B2 | 2/2019 | Scheib | |
| 10,226,250 B2 | 3/2019 | Beckman | |
| 10,231,734 B2 | 3/2019 | Thompson | |
| 10,238,517 B2 | 3/2019 | Gingras | |
| 10,245,032 B2 | 4/2019 | Shelton, IV | |
| 10,258,334 B2 | 4/2019 | Adams | |
| 10,265,073 B2 | 4/2019 | Scheib | |
| 10,278,695 B2 | 5/2019 | Milo | |
| 10,278,699 B2 | 5/2019 | Thompson | |
| 10,278,707 B2 | 5/2019 | Thompson | |
| 10,285,712 B2 | 5/2019 | Cosgrove, III | |
| 10,285,837 B1 | 5/2019 | Thompson | |
| 10,292,706 B2 | 5/2019 | Jankowski | |
| 10,307,161 B2 | 6/2019 | Jankowski | |
| 10,307,163 B2 | 6/2019 | Moore | |
| 10,314,580 B2 | 6/2019 | Scheib | |
| 10,314,589 B2 | 6/2019 | Shelton, IV | |
| 10,342,538 B2 | 7/2019 | Racenet | |
| 10,383,628 B2 | 8/2019 | Kang | |
| 10,390,826 B2 | 8/2019 | Badawi | |
| 10,405,856 B2 | 9/2019 | Knodel | |
| 10,405,860 B2 | 9/2019 | Thompson | |
| 10,420,559 B2 | 9/2019 | Marczyk | |
| 10,420,560 B2 | 9/2019 | Shelton, IV | |
| 10,441,283 B1 | 10/2019 | Thompson | |
| 10,456,571 B2 | 10/2019 | Cairns | |
| 10,470,911 B2 | 11/2019 | Thompson | |
| 10,485,540 B2 | 11/2019 | Hodgkinson | |
| 10,499,912 B2 | 12/2019 | Scheib | |
| 10,537,325 B2 | 1/2020 | Bakos | |
| 10,542,986 B2 | 1/2020 | Thompson | |
| 10,548,597 B2 | 2/2020 | Dunki-Jacobs | |
| 10,561,419 B2 * | 2/2020 | Beardsley | A61B 17/07207 |
| 10,610,226 B2 | 4/2020 | Shelton, IV | |
| 10,624,638 B2 | 4/2020 | Thompson | |
| 10,687,807 B2 | 6/2020 | Simms | |
| 10,687,810 B2 | 6/2020 | Shelton, IV | |
| 10,687,814 B2 | 6/2020 | Dunki-Jacobs | |
| 10,716,564 B2 | 7/2020 | Shelton, IV | |
| 10,758,231 B2 | 9/2020 | Harris | |
| 10,849,623 B2 | 12/2020 | Dunki-Jacobs | |
| 10,912,562 B2 | 2/2021 | Dunki-Jacobs | |
| 10,966,721 B2 | 4/2021 | Dunki-Jacobs | |
| 10,987,108 B2 | 4/2021 | Thompson | |
| 11,173,060 B2 | 11/2021 | Thompson | |
| 11,197,672 B2 | 12/2021 | Dunki-Jacobs | |
| 2001/0044656 A1 | 11/2001 | Williamson | |
| 2002/0143346 A1 | 10/2002 | McGuckin | |
| 2002/0185517 A1 | 12/2002 | Vresh | |
| 2003/0009193 A1 | 1/2003 | Corsaro | |
| 2003/0125734 A1 | 7/2003 | Mollenauer | |
| 2003/0135091 A1 | 7/2003 | Nakazawa | |
| 2003/0178465 A1 | 9/2003 | Bilotti | |
| 2003/0208209 A1 | 11/2003 | Gambale | |
| 2003/0220660 A1 | 11/2003 | Kortenbach | |
| 2004/0006351 A1 | 1/2004 | Gannoe | |
| 2004/0006372 A1 | 1/2004 | Racenet | |
| 2004/0068267 A1 | 4/2004 | Harvie | |
| 2004/0094597 A1 | 5/2004 | Whitman | |
| 2004/0181239 A1 | 9/2004 | Dorn | |
| 2004/0215216 A1 | 10/2004 | Gannoe | |
| 2005/0006432 A1 | 1/2005 | Racenet | |
| 2005/0006434 A1 | 1/2005 | Wales | |
| 2005/0080444 A1 | 4/2005 | Kraemer | |
| 2005/0139633 A1 | 6/2005 | Wukusick | |
| 2005/0203547 A1 | 9/2005 | Weller | |
| 2005/0203548 A1 * | 9/2005 | Weller | A61B 17/07207 |
| | | | 606/139 |
| 2005/0256533 A1 | 11/2005 | Roth | |
| 2006/0011698 A1 | 1/2006 | Okada | |
| 2006/0016853 A1 | 1/2006 | Racenet | |
| 2006/0020277 A1 | 1/2006 | Gostout | |
| 2006/0036267 A1 | 2/2006 | Saadat et al. | |
| 2006/0041270 A1 | 2/2006 | Lenker | |
| 2006/0085030 A1 | 4/2006 | Bettuchi | |
| 2006/0122462 A1 | 6/2006 | Roth | |
| 2006/0151568 A1 * | 7/2006 | Weller | A61B 17/07207 |
| | | | 227/175.1 |
| 2006/0229665 A1 | 10/2006 | Wales | |
| 2006/0241692 A1 | 10/2006 | McGuckin | |
| 2007/0023477 A1 | 2/2007 | Whitman | |
| 2007/0027469 A1 | 2/2007 | Smith | |
| 2007/0029364 A1 | 2/2007 | Kruszynski | |
| 2007/0034666 A1 | 2/2007 | Holsten | |
| 2007/0034667 A1 | 2/2007 | Holsten | |
| 2007/0039997 A1 | 2/2007 | Mather | |
| 2007/0056932 A1 | 3/2007 | Whitman | |
| 2007/0075114 A1 | 4/2007 | Shelton | |
| 2007/0083233 A1 | 4/2007 | Ortiz | |
| 2007/0114261 A1 | 5/2007 | Ortiz | |
| 2007/0131732 A1 | 6/2007 | Holsten | |
| 2007/0179528 A1 | 8/2007 | Soltz | |
| 2007/0194079 A1 | 8/2007 | Hueil | |
| 2007/0194080 A1 | 8/2007 | Swayze | |
| 2007/0194081 A1 | 8/2007 | Hueil | |
| 2007/0198408 A1 | 8/2007 | Beer | |
| 2007/0213743 A1 | 9/2007 | McGuckin, Jr. | |
| 2007/0246505 A1 | 10/2007 | Pace-Floridia | |
| 2007/0246508 A1 | 10/2007 | Green | |
| 2007/0262116 A1 | 11/2007 | Hueil | |
| 2007/0265644 A1 | 11/2007 | Ichihara | |
| 2008/0015631 A1 | 1/2008 | Lee | |
| 2008/0023522 A1 | 1/2008 | Olson | |

(56)        References Cited

U.S. PATENT DOCUMENTS

| | | | |
|---|---|---|---|
| 2008/0033457 A1* | 2/2008 | Francischelli ..... A61B 17/1285 | |
| | | 606/157 | |
| 2008/0035702 A1 | 2/2008 | Holsten | |
| 2008/0041918 A1 | 2/2008 | Holsten | |
| 2008/0058716 A1 | 3/2008 | Dubrul | |
| 2008/0078800 A1 | 4/2008 | Hess | |
| 2008/0082124 A1 | 4/2008 | Hess | |
| 2008/0087707 A1 | 4/2008 | Jankowski | |
| 2008/0097332 A1 | 4/2008 | Greenhalgh | |
| 2008/0149684 A1 | 6/2008 | Viola | |
| 2008/0164297 A1 | 7/2008 | Holsten | |
| 2008/0169329 A1 | 7/2008 | Shelton | |
| 2008/0169332 A1 | 7/2008 | Shelton | |
| 2008/0190990 A1 | 8/2008 | Holsten | |
| 2008/0203134 A1 | 8/2008 | Shah | |
| 2008/0249404 A1 | 10/2008 | Mikkaichi | |
| 2008/0275480 A1 | 11/2008 | Jacobs | |
| 2008/0294179 A1 | 11/2008 | Balbierz | |
| 2008/0308602 A1 | 12/2008 | Timm | |
| 2008/0308606 A1 | 12/2008 | Timm | |
| 2008/0308607 A1 | 12/2008 | Timm | |
| 2009/0001122 A1 | 1/2009 | Prommersberger | |
| 2009/0001130 A1 | 1/2009 | Hess | |
| 2009/0012556 A1 | 1/2009 | Boudreaux | |
| 2009/0020584 A1 | 1/2009 | Soltz | |
| 2009/0039137 A1 | 2/2009 | Viola | |
| 2009/0065552 A1 | 3/2009 | Knodel | |
| 2009/0078739 A1 | 3/2009 | Viola | |
| 2009/0095791 A1 | 4/2009 | Eskaros | |
| 2009/0101692 A1* | 4/2009 | Whitman ............... A61B 90/98 | |
| | | 227/175.1 | |
| 2009/0134200 A1 | 5/2009 | Tarinelli | |
| 2009/0173766 A1 | 7/2009 | Wenchell | |
| 2009/0206134 A1 | 8/2009 | Swayze | |
| 2009/0209946 A1 | 8/2009 | Swayze | |
| 2009/0209986 A1 | 8/2009 | Stewart | |
| 2009/0212088 A1 | 8/2009 | Okada | |
| 2009/0255974 A1* | 10/2009 | Viola ............... A61B 17/07207 | |
| | | 227/176.1 | |
| 2009/0261144 A1 | 10/2009 | Sniffin | |
| 2009/0281554 A1 | 11/2009 | Viola | |
| 2009/0302092 A1 | 12/2009 | Kasvikis | |
| 2009/0308907 A1 | 12/2009 | Nalagatla | |
| 2010/0010512 A1 | 1/2010 | Taylor | |
| 2010/0038403 A1* | 2/2010 | D'Arcangelo ....... A61B 17/072 | |
| | | 227/176.1 | |
| 2010/0072255 A1 | 3/2010 | Olson | |
| 2010/0072258 A1 | 3/2010 | Farascioni | |
| 2010/0108739 A1 | 5/2010 | Holsten | |
| 2010/0108740 A1 | 5/2010 | Pastorelli | |
| 2010/0114124 A1* | 5/2010 | Kelleher ............ A61B 17/1227 | |
| | | 606/151 | |
| 2010/0121356 A1 | 5/2010 | Hartmann | |
| 2010/0137904 A1 | 6/2010 | Wenchell | |
| 2010/0145324 A1 | 6/2010 | Nihalani | |
| 2010/0213240 A1* | 8/2010 | Kostrzewski ...... A61B 17/3209 | |
| | | 227/180.1 | |
| 2010/0256634 A1 | 10/2010 | Voegele | |
| 2010/0282820 A1 | 11/2010 | Kasvikis | |
| 2010/0331866 A1 | 12/2010 | Surti | |
| 2011/0004062 A1 | 1/2011 | Asai | |
| 2011/0004210 A1 | 1/2011 | Johnson | |
| 2011/0011916 A1 | 1/2011 | Levine | |
| 2011/0017800 A1 | 1/2011 | Viola | |
| 2011/0036888 A1 | 2/2011 | Pribanic | |
| 2011/0046653 A1 | 2/2011 | Addington | |
| 2011/0071555 A1 | 3/2011 | McBrayer | |
| 2011/0084113 A1 | 4/2011 | Bedi | |
| 2011/0087169 A1 | 4/2011 | Parihar | |
| 2011/0087279 A1 | 4/2011 | Shah | |
| 2011/0152895 A1* | 6/2011 | Nyuli ................... A61B 17/122 | |
| | | 606/151 | |
| 2011/0160752 A1 | 6/2011 | Aguirre | |
| 2011/0178454 A1 | 7/2011 | Gagner | |
| 2011/0186614 A1 | 8/2011 | Kasvikis | |
| 2011/0190791 A1* | 8/2011 | Jacobs ............... A61B 17/1285 | |
| | | 606/139 | |
| 2011/0208211 A1 | 8/2011 | Whitfield | |
| 2011/0226837 A1 | 9/2011 | Baxter, III | |
| 2011/0248064 A1 | 10/2011 | Marczyk | |
| 2011/0278343 A1* | 11/2011 | Knodel ............ A61B 17/07207 | |
| | | 227/176.1 | |
| 2011/0290851 A1* | 12/2011 | Shelton, IV ..... A61B 17/07207 | |
| | | 227/176.1 | |
| 2011/0297729 A1 | 12/2011 | Whitman | |
| 2011/0315739 A1* | 12/2011 | Sniffin ............. A61B 17/07207 | |
| | | 227/176.1 | |
| 2012/0035631 A1* | 2/2012 | Hughett, Sr ....... A61B 17/1285 | |
| | | 606/157 | |
| 2012/0037686 A1 | 2/2012 | Hessler | |
| 2012/0059400 A1 | 3/2012 | Williamson, IV | |
| 2012/0080492 A1 | 4/2012 | Scirica | |
| 2012/0080494 A1 | 4/2012 | Thompson | |
| 2012/0116379 A1 | 5/2012 | Yates | |
| 2012/0123463 A1 | 5/2012 | Jacobs | |
| 2012/0138660 A1 | 6/2012 | Shelton, IV | |
| 2012/0175398 A1* | 7/2012 | Sandborn ............. A61B 17/072 | |
| | | 227/175.1 | |
| 2012/0193395 A1 | 8/2012 | Pastorelli | |
| 2012/0193396 A1 | 8/2012 | Zemlok | |
| 2012/0193398 A1* | 8/2012 | Williams ........... A61B 17/1155 | |
| | | 227/179.1 | |
| 2012/0203247 A1 | 8/2012 | Shelton, IV | |
| 2012/0234899 A1 | 9/2012 | Scheib | |
| 2012/0234900 A1 | 9/2012 | Swayze | |
| 2012/0248169 A1 | 10/2012 | Widenhouse | |
| 2012/0277525 A1 | 11/2012 | O'Dea | |
| 2012/0286022 A1 | 11/2012 | Olson | |
| 2012/0289979 A1 | 11/2012 | Eskaros | |
| 2012/0325893 A1 | 12/2012 | Pastorelli | |
| 2013/0062394 A1 | 3/2013 | Smith | |
| 2013/0075447 A1 | 3/2013 | Weisenburgh, II | |
| 2013/0075450 A1 | 3/2013 | Schmid | |
| 2013/0082086 A1 | 4/2013 | Hueil | |
| 2013/0092718 A1 | 4/2013 | Soltz | |
| 2013/0092720 A1 | 4/2013 | Williams | |
| 2013/0098970 A1* | 4/2013 | Racenet ........... A61B 17/07207 | |
| | | 227/180.1 | |
| 2013/0105549 A1 | 5/2013 | Holsten | |
| 2013/0105554 A1 | 5/2013 | Kostrzewski | |
| 2013/0131440 A1 | 5/2013 | Gabriel | |
| 2013/0146638 A1 | 6/2013 | Mandakolathur Vasudevan | |
| 2013/0146641 A1 | 6/2013 | Shelton, IV | |
| 2013/0146642 A1 | 6/2013 | Shelton, IV | |
| 2013/0153625 A1 | 6/2013 | Felder | |
| 2013/0153634 A1 | 6/2013 | Carter | |
| 2013/0153642 A1 | 6/2013 | Felder | |
| 2013/0161374 A1 | 6/2013 | Swayze | |
| 2013/0165774 A1 | 6/2013 | Nocca | |
| 2013/0172929 A1 | 7/2013 | Hess | |
| 2013/0193190 A1 | 8/2013 | Carter | |
| 2013/0214025 A1 | 8/2013 | Zemlok | |
| 2013/0214030 A1 | 8/2013 | Aronhalt | |
| 2013/0240595 A1* | 9/2013 | Penna .............. A61B 17/07207 | |
| | | 227/175.1 | |
| 2013/0245652 A1 | 9/2013 | Cosgrove | |
| 2013/0256372 A1 | 10/2013 | Baxter, III | |
| 2013/0256373 A1 | 10/2013 | Schmid | |
| 2013/0256375 A1 | 10/2013 | Shelton, IV | |
| 2013/0256377 A1 | 10/2013 | Schmid | |
| 2013/0284791 A1 | 10/2013 | Olson | |
| 2013/0306704 A1 | 11/2013 | Balbierz | |
| 2013/0327809 A1* | 12/2013 | Shelton, IV ......... A61B 17/072 | |
| | | 227/176.1 | |
| 2013/0334288 A1 | 12/2013 | Shelton, IV | |
| 2013/0341374 A1 | 12/2013 | Shelton, IV | |
| 2014/0005678 A1* | 1/2014 | Shelton, IV ......... A61B 17/068 | |
| | | 606/130 | |
| 2014/0008412 A1 | 1/2014 | Zemlok | |
| 2014/0008413 A1 | 1/2014 | Williams | |
| 2014/0018722 A1 | 1/2014 | Scott | |
| 2014/0021239 A1 | 1/2014 | Kostrzewski | |

(56) References Cited

U.S. PATENT DOCUMENTS

| | | | |
|---|---|---|---|
| 2014/0027493 A1 | 1/2014 | Jankowski | |
| 2014/0046345 A1 | 2/2014 | Armenteros | |
| 2014/0048580 A1 | 2/2014 | Merchant | |
| 2014/0074131 A1 | 3/2014 | Armenteros | |
| 2014/0081176 A1 | 3/2014 | Hassan et al. | |
| 2014/0082497 A1 | 3/2014 | Chalouhi | |
| 2014/0107698 A1 | 4/2014 | Inge | |
| 2014/0110457 A1 | 4/2014 | Zhang | |
| 2014/0114121 A1 | 4/2014 | Trivedi | |
| 2014/0131418 A1 | 5/2014 | Kostrzewski | |
| 2014/0131419 A1 | 5/2014 | Bettuchi | |
| 2014/0144968 A1 | 5/2014 | Shelton, IV | |
| 2014/0148731 A1 | 5/2014 | Radl et al. | |
| 2014/0155915 A1 | 6/2014 | Mikkaichi | |
| 2014/0166726 A1 | 6/2014 | Schellin | |
| 2014/0171744 A1 | 6/2014 | Racenet | |
| 2014/0183242 A1 | 7/2014 | Farascioni | |
| 2014/0184519 A1 | 7/2014 | Benchenaa | |
| 2014/0191015 A1 | 7/2014 | Shelton, IV | |
| 2014/0214025 A1 | 7/2014 | Worrell | |
| 2014/0231489 A1 | 8/2014 | Balbierz | |
| 2014/0239037 A1 | 8/2014 | Boudreaux | |
| 2014/0257353 A1 | 9/2014 | Whitman | |
| 2014/0257370 A1 | 9/2014 | Taylor | |
| 2014/0263570 A1 | 9/2014 | Hopkins | |
| 2014/0276932 A1 | 9/2014 | Williams | |
| 2014/0291379 A1 | 10/2014 | Schellin | |
| 2015/0048141 A1 | 2/2015 | Felder | |
| 2015/0083780 A1 | 3/2015 | Shelton, IV | |
| 2015/0133740 A1 | 5/2015 | Dierking | |
| 2015/0157318 A1 | 6/2015 | Beardsley | |
| 2015/0157323 A1 | 6/2015 | Williams | |
| 2015/0173746 A1* | 6/2015 | Baxter, III | A61B 17/07207 |
| | | | 227/176.1 |
| 2015/0173755 A1 | 6/2015 | Baxter, III | |
| 2015/0173762 A1 | 6/2015 | Shelton, IV | |
| 2015/0209034 A1 | 7/2015 | Viola | |
| 2015/0223809 A1 | 8/2015 | Scheib | |
| 2015/0265276 A1 | 9/2015 | Huitema | |
| 2015/0297224 A1 | 10/2015 | Hall | |
| 2015/0297227 A1 | 10/2015 | Huitema | |
| 2015/0297236 A1 | 10/2015 | Harris | |
| 2015/0320423 A1 | 11/2015 | Aranyi | |
| 2015/0351763 A1 | 12/2015 | Shelton, IV | |
| 2015/0351764 A1 | 12/2015 | Shelton, IV | |
| 2016/0058447 A1 | 3/2016 | Posada | |
| 2016/0058594 A1 | 3/2016 | Armenteros | |
| 2016/0066916 A1 | 3/2016 | Overmyer | |
| 2016/0067074 A1 | 3/2016 | Thompson | |
| 2016/0089148 A1 | 3/2016 | Harris | |
| 2016/0157926 A1 | 6/2016 | Boudreaux | |
| 2016/0166256 A1 | 6/2016 | Baxter, III | |
| 2016/0183945 A1 | 6/2016 | Shelton, IV | |
| 2016/0192927 A1 | 7/2016 | Kostrzewski | |
| 2016/0199061 A1 | 7/2016 | Shelton, IV | |
| 2016/0199088 A1 | 7/2016 | Shelton, IV | |
| 2016/0213302 A1 | 7/2016 | Frushour | |
| 2016/0235409 A1 | 8/2016 | Shelton, IV | |
| 2016/0242768 A1 | 8/2016 | Moore | |
| 2016/0242769 A1 | 8/2016 | Moore | |
| 2016/0242770 A1 | 8/2016 | Moore | |
| 2016/0242783 A1 | 8/2016 | Shelton, IV | |
| 2016/0256152 A1* | 9/2016 | Kostrzewski | A61B 17/42 |
| 2016/0262744 A1 | 9/2016 | Milo | |
| 2016/0262750 A1* | 9/2016 | Hausen | A61B 17/32 |
| 2016/0262921 A1 | 9/2016 | Balbierz | |
| 2016/0270792 A1 | 9/2016 | Sniffin | |
| 2016/0287251 A1* | 10/2016 | Shelton, IV | A61B 17/07207 |
| 2016/0296272 A1 | 10/2016 | Heard | |
| 2016/0324527 A1 | 11/2016 | Thompson et al. | |
| 2016/0354085 A1 | 12/2016 | Shelton, IV | |
| 2016/0367250 A1 | 12/2016 | Racenet | |
| 2017/0007248 A1 | 1/2017 | Shelton, IV | |
| 2017/0014125 A1 | 1/2017 | Shelton, IV | |
| 2017/0027633 A1 | 2/2017 | Wham | |

| | | | |
|---|---|---|---|
| 2017/0055981 A1 | 3/2017 | Vendely | |
| 2017/0055991 A1 | 3/2017 | Kang | |
| 2017/0056016 A1 | 3/2017 | Barton | |
| 2017/0086847 A1 | 3/2017 | DiNardo | |
| 2017/0095251 A1* | 4/2017 | Thompson | A61F 5/0089 |
| 2017/0105728 A1 | 4/2017 | Scheib | |
| 2017/0172571 A1* | 6/2017 | Thompson | A61B 17/07207 |
| 2017/0231633 A1 | 8/2017 | Marczyk | |
| 2017/0281187 A1 | 10/2017 | Shelton, IV | |
| 2017/0290588 A1 | 10/2017 | Thompson | |
| 2017/0303952 A1 | 10/2017 | Nativ | |
| 2017/0319210 A1 | 11/2017 | Moore | |
| 2017/0333041 A1 | 11/2017 | Moore | |
| 2017/0360447 A1 | 12/2017 | Armenteros | |
| 2017/0367697 A1 | 12/2017 | Shelton, IV | |
| 2018/0008260 A1 | 1/2018 | Baxter, III | |
| 2018/0014826 A1 | 1/2018 | Scheib | |
| 2018/0036000 A1 | 2/2018 | Terada | |
| 2018/0036005 A1 | 2/2018 | Covach | |
| 2018/0092641 A1 | 4/2018 | Aranyi | |
| 2018/0125491 A1 | 5/2018 | Aranyi | |
| 2018/0168594 A1 | 6/2018 | Shelton, IV | |
| 2018/0168620 A1* | 6/2018 | Huang | A61B 17/072 |
| 2018/0168633 A1 | 6/2018 | Shelton, IV | |
| 2018/0199939 A1 | 7/2018 | Thompson | |
| 2018/0199941 A1 | 7/2018 | Thompson | |
| 2018/0235625 A1 | 8/2018 | Shelton, IV | |
| 2018/0235626 A1 | 8/2018 | Shelton, IV | |
| 2018/0280020 A1 | 10/2018 | Hess | |
| 2018/0317905 A1 | 11/2018 | Olson | |
| 2019/0000455 A1 | 1/2019 | Adams | |
| 2019/0046186 A1 | 2/2019 | Dunki-Jacobs | |
| 2019/0046189 A1* | 2/2019 | Dunki-Jacobs | |
| | | | A61B 17/07207 |
| 2019/0046190 A1 | 2/2019 | Dunki-Jacobs | |
| 2019/0046191 A1 | 2/2019 | Dunki-Jacobs | |
| 2019/0046192 A1 | 2/2019 | Dunki-Jacobs | |
| 2019/0046193 A1 | 2/2019 | Dunki-Jacobs | |
| 2019/0105042 A1 | 4/2019 | Huitema | |
| 2019/0133577 A1 | 5/2019 | Weadock | |
| 2019/0150924 A1 | 5/2019 | Thompson | |
| 2019/0209173 A1 | 7/2019 | Thompson | |
| 2019/0209175 A1 | 7/2019 | Thompson | |
| 2019/0224029 A1 | 7/2019 | Thompson | |
| 2019/0261985 A1 | 8/2019 | Adams | |
| 2019/0261991 A1 | 8/2019 | Beckman | |
| 2019/0269404 A1 | 9/2019 | Nie | |
| 2019/0269408 A1 | 9/2019 | Jankowski | |
| 2019/0274677 A1 | 9/2019 | Shelton, IV | |
| 2019/0274678 A1 | 9/2019 | Shelton, IV | |
| 2019/0274679 A1 | 9/2019 | Shelton, IV | |
| 2019/0274680 A1 | 9/2019 | Shelton, IV | |
| 2019/0307450 A1 | 10/2019 | Thompson | |
| 2019/0343519 A1 | 11/2019 | Thompson | |
| 2019/0380742 A1 | 12/2019 | Hall | |
| 2019/0388092 A1 | 12/2019 | Thompson | |
| 2020/0008964 A1 | 1/2020 | Thompson | |
| 2020/0015822 A1 | 1/2020 | Marczyk | |
| 2020/0054326 A1 | 2/2020 | Harris | |
| 2020/0100790 A1 | 4/2020 | DiNardo | |
| 2020/0205810 A1 | 7/2020 | Posey | |
| 2020/0205827 A1 | 7/2020 | Bakos | |
| 2020/0206805 A1 | 7/2020 | Nalagatla | |
| 2020/0214703 A1 | 7/2020 | Thompson | |
| 2020/0229818 A1 | 7/2020 | Thompson | |
| 2020/0268385 A1 | 8/2020 | Dunki-Jacobs | |
| 2020/0297344 A1 | 9/2020 | Dunki-Jacobs | |
| 2020/0305865 A1 | 10/2020 | Shelton, IV | |
| 2020/0305868 A1 | 10/2020 | Shelton, IV | |
| 2020/0305869 A1 | 10/2020 | Shelton, IV | |
| 2020/0305870 A1* | 10/2020 | Shelton, IV | A61B 17/29 |
| 2020/0305873 A1 | 10/2020 | Dunki-Jacobs | |
| 2020/0305989 A1 | 10/2020 | Schuh | |
| 2020/0390443 A1 | 12/2020 | Thompson | |
| 2021/0128335 A1 | 5/2021 | Thompson | |
| 2021/0177411 A1 | 6/2021 | Williams | |
| 2021/0369330 A1 | 12/2021 | Brandt | |
| 2021/0393319 A1 | 12/2021 | Shelton, IV | |
| 2022/0061862 A1 | 3/2022 | Shelton, IV | |

(56) References Cited

U.S. PATENT DOCUMENTS

| | | | |
|---|---|---|---|
| 2022/0079590 A1 | 3/2022 | Harris | |
| 2022/0409205 A1 | 12/2022 | Thompson | |
| 2023/0049352 A1 | 2/2023 | Shelton, IV | |

FOREIGN PATENT DOCUMENTS

| | | | |
|---|---|---|---|
| CA | 2663002 A1 | 10/2009 | |
| EP | 0140552 A2 | 5/1985 | |
| EP | 0399699 A1 | 11/1990 | |
| EP | 0503662 A1 | 9/1992 | |
| EP | 0666057 A2 | 8/1995 | |
| EP | 0669104 A1 | 8/1995 | |
| EP | 1090592 A1 | 4/2001 | |
| EP | 0749288 B1 * | 10/2003 | |
| EP | 1616526 A1 | 1/2006 | |
| EP | 1722691 A1 | 11/2006 | |
| EP | 1769766 A1 | 4/2007 | |
| EP | 1774916 A1 | 4/2007 | |
| EP | 1806101 A1 | 7/2007 | |
| EP | 1875868 A1 | 1/2008 | |
| EP | 1875870 A1 | 1/2008 | |
| EP | 1938759 A2 | 7/2008 | |
| EP | 2005896 A2 | 12/2008 | |
| EP | 2005897 A2 | 12/2008 | |
| EP | 2005898 A2 | 12/2008 | |
| EP | 2005899 A2 | 12/2008 | |
| EP | 2005900 A2 | 12/2008 | |
| EP | 2005901 A1 | 12/2008 | |
| EP | 2090247 A1 | 8/2009 | |
| EP | 2111803 A2 | 10/2009 | |
| EP | 2245993 A2 | 11/2010 | |
| EP | 2319424 A1 | 5/2011 | |
| EP | 2382928 A1 | 11/2011 | |
| EP | 2019633 B1 | 8/2012 | |
| EP | 2486860 A2 | 8/2012 | |
| FR | 2731895 A1 | 9/1996 | |
| GB | 2298905 A | 9/1996 | |
| JP | 6113667 B2 | 4/2017 | |
| WO | 01/54594 A1 | 8/2001 | |
| WO | 02/60328 A1 | 8/2002 | |
| WO | 03/94747 A1 | 11/2003 | |
| WO | 2005/092210 A1 | 10/2005 | |
| WO | 2007/009099 A2 | 1/2007 | |
| WO | 2007/019268 A2 | 2/2007 | |
| WO | 2007/102152 A2 | 9/2007 | |
| WO | 2007/127664 A1 | 11/2007 | |
| WO | 2008/039238 A1 | 4/2008 | |
| WO | 2008/039249 A1 | 4/2008 | |
| WO | 2008/039250 A1 | 4/2008 | |
| WO | 2008/039270 A1 | 4/2008 | |
| WO | 2008/042021 A1 | 4/2008 | |
| WO | 2008/042022 A1 | 4/2008 | |
| WO | 2008/042043 A1 | 4/2008 | |
| WO | 2008/042044 A2 | 4/2008 | |
| WO | 2008/042045 A2 | 4/2008 | |
| WO | 2008/094210 A1 | 8/2008 | |
| WO | 2008/141288 A1 | 11/2008 | |
| WO | 2009/038550 A1 | 3/2009 | |
| WO | 2010/011661 A1 | 1/2010 | |
| WO | 2011/044032 A2 | 4/2011 | |
| WO | 2011/094700 A1 | 8/2011 | |
| WO | 2012/125615 A2 | 9/2012 | |
| WO | 2012/141679 A1 | 10/2012 | |
| WO | 2013/151888 A1 | 10/2013 | |
| WO | 2014/026170 A2 | 2/2014 | |
| WO | 2014/085099 A1 | 6/2014 | |
| WO | 2015/063609 A2 | 5/2015 | |
| WO | 2015/153324 A1 | 10/2015 | |
| WO | 2015/153340 A2 | 10/2015 | |
| WO | 2016/033221 A1 | 3/2016 | |

OTHER PUBLICATIONS

Chekan, E. et al.; Surgical stapling device-tissue interactions: what surgeons need to know to improve patient outcomes; Dovepress;

Medical Devices: Evidence and Research 2014(7):305-18; Sep. 12, 2014; URL: https://www.ncbi.nlm.nih.gov/pmc/articles/PMC4168870/.

International Search Report and Written Opinion of the International Searching Authority received in International Patent App. No. PCT/US2020/058960; mailed Feb. 2, 2021; 16 pages.

Atricure, Inc.; 510(k) Summary for AtriClip LAA Exclusion System with preloaded Gillinov-Cosgrove Clip; published Jun. 10, 2010; 6 pages.

Communication pursuant to Article 94(3) EPC received in European Patent Appln. No. 18 845 739.4; mailed Apr. 28, 2022; 9 pages.

de Petz, A; Aseptic Technic of Stomach Resections; 86 Annals of Surgery 388; Sep. 1927; 5 pages.

Dept. of Health and Human Services; CMS Description of Open Left Atrial Appendage Occlusion with "U" Fastener Implant; Mar. 9, 2011; 1 page.

European Search Report received in European Application No. 15774247; dated Dec. 23, 2016; 11 pages.

Examination Report of the European Patent Office, Issued in European Application No. 15772561.5-1122; dated Oct. 29, 2018; 7 pages.

Examination Report received in Australian Application No. 2015241193; dated Dec. 11, 2018; 5 pages.

Examination Report received in Australian Application No. 2015241267; dated Feb. 25, 2019; 6 pages.

Examination Report received in Australian Application No. 2016208416; dated May 18, 2017; 4 pages.

Examination Report received in Australian Application No. 2018203527; dated Oct. 22, 2018; 5 pages.

Examination Report received in Australian Patent Appln. No. 2022204678; mailed Jul. 7, 2022; 4 pages.

Felicien M. Steichen and Mark M. Ravitch, Stapling in Surgery, Figure 1-11C, Year Book Medical Publishers, Inc. 1984; 3 pages.

Geoffrey Parker, A New Stomach Clamp, 26 Postgrad Med. J. 550; 1 page.

Harrah, J. D.; A Lung Clamp for Use with Mechanical Staplers; 28 The Annals of Thoracic Surgery 489; Nov. 1979; 2 pages.

International Preliminary Report on Patentability and Written Opinion of the International Searching Authority received in Application No. PCT/US2018/046743; dated Feb. 18, 2020; 17 pages.

International Preliminary Report on Patentability and Written Opinion of the International Searching Authority received in International Patent App. No. PCT/US2015/048740; dated Mar. 7, 2017; 8 pages.

International Search Report and Written Opinion of the International Searching Authority for PCT/US2014/070869 dated as mailed on Apr. 21, 2015; 17 pages.

International Search Report and Written Opinion of the International Searching Authority received in International Patent App. No. PCT/US2015/022904; mailed Jun. 25, 2015; 6 pages.

International Search Report and Written Opinion of the International Searching Authority received in International Patent App. No. PCT/US2015/022990; mailed Sep. 30, 2015; 10 pages.

International Search Report and Written Opinion of the International Searching Authority received in International Patent App. No. PCT/US2015/048740; mailed Feb. 17, 2016; 12 pages.

International Search Report and Written Opinion of the International Searching Authority received in International Patent App. No. PCT/US2018/046743; mailed Dec. 4, 2018; 20 pages.

International Search Report and Written Opinion of the International Searching Authority received in International Patent Appln. No. PCT/US2022/021250; mailed Jun. 10, 2022; 12 pages.

Jacobs, M. et al.; Laparoscopic sleeve gastrectomy: a retrospective review of 1- and 2-year results; Surg Endosc. Apr. 2010; 24(4):781-5; doi: 10.1007/s00464-009-0619-8; Epub Aug. 19, 2009; abstract only; 2 pages.

LAAx, Inc.; 510(k) Summary for TigerPaw(R) System; published Oct. 29, 2010; 6 pages.

Notice of Acceptance received in Australian Application No. 2019284071 received on May 3, 2021; 4 pages.

(56) References Cited

OTHER PUBLICATIONS

Parikh, M. et al.; Surgical Strategies That May Decrease Leak After Laparoscopic Sleeve Gastrectomy; 257 Annals of Surgery 231; Feb. 2013; 7 pages.

Pfiedler Enterprises; Science of Stapling: Urban Legend and Fact; Jun. 4, 2012; 38 pages.

Regan, J. P. et al.; Early Experience with Two-Stage Laparoscopic Roux-en-Y Gastric Bypass as an Alternative in the Super-Super Obese Patient; Obes Surg; 13(6):861-4; Dec. 1, 2003; abstract only; 2 pages.

Search Report received in Chinese Application No. 201480075706. 2; dated Nov. 28, 2018; 3 pages.

Supplementary European Search Report of the European Patent Office, Issued in European Application No. 15772561.5-1664; dated Mar. 15, 2017; 8 pages.

Supplementary European Search Report received in European Application No. 14872137; dated Mar. 28, 2017; 15 pages.

Supplementary Partial European Search Report received in European Application No. 14872137; dated Dec. 12, 2016; 5 pages.

Zuckerman, B. D., Food and Drug Administration; Letter to AtriCure, Inc. Addressing Indication for Use of AtriClip LAA Exclusion System w/Pre-loaded Gillnov-Cosgrove Clip; Jun. 10, 2010; 3 pages.

* cited by examiner

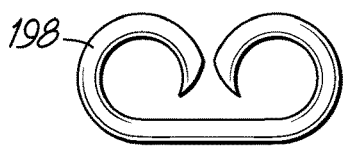
FIG. 37A
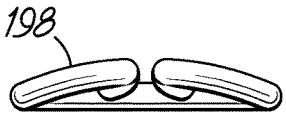
FIG. 37B
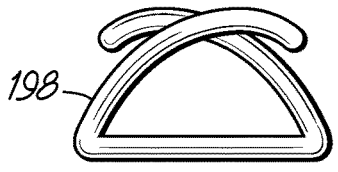
FIG. 38A
FIG. 38B
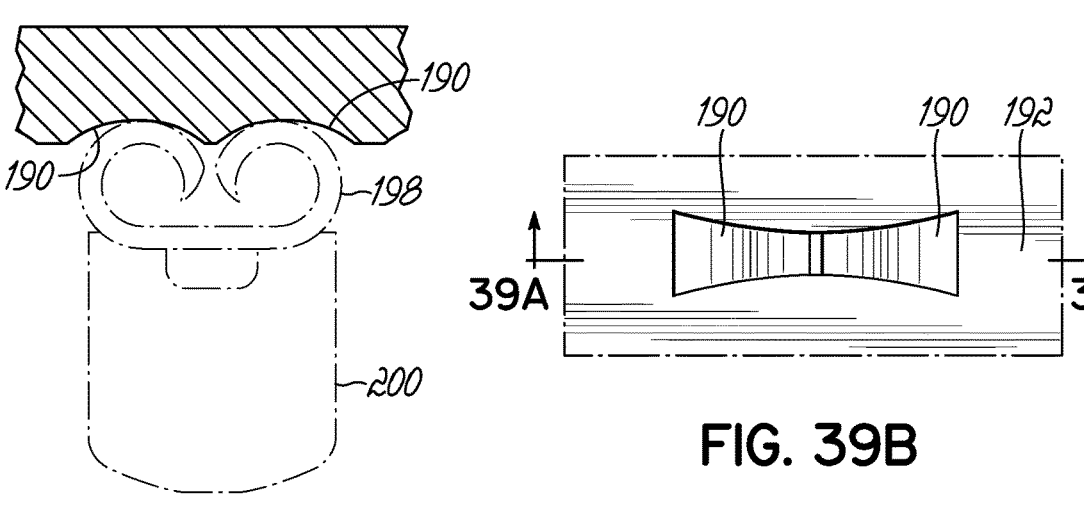
FIG. 39A
FIG. 39B
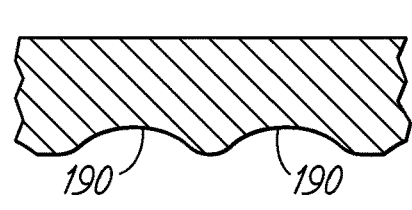
FIG. 40A
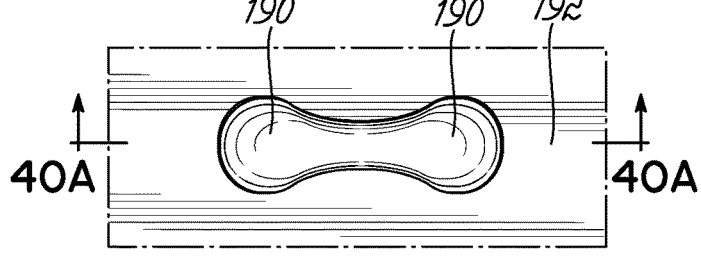
FIG. 40B

END EFFECTORS, SURGICAL STAPLING DEVICES, AND METHODS OF USING SAME

REFERENCE TO RELATED APPLICATIONS

This application is a continuation of U.S. Non-Provisional application Ser. No. 17/005,050, filed Aug. 27, 2020, which is a continuation of Ser. No. 16/818,252, filed Mar. 13, 2020, which is a continuation of U.S. Non-Provisional application Ser. No. 16/538,480, filed Aug. 12, 2019, which is a continuation of U.S. Non-Provisional application Ser. No. 15/633,399, filed Jun. 26, 2017, which is a continuation of U.S. Non-Provisional application Ser. No. 15/129,366, filed Sep. 26, 2016, now U.S. Pat. No. 9,724,096, which was a National Stage Application under 35 U.S.C. § 371 of PCT International Application No. PCT/US2015/022990, filed Mar. 27, 2015, which claims the priority benefit of U.S. Provisional Patent App. No. 61/972,274 filed Mar. 29, 2014, and U.S. Provisional Patent App. No. 62/046,726 filed Sep. 5, 2014, each of which is incorporated herein by reference in its entirety.

TECHNICAL FIELD

The invention relates to surgical staplers, and more particularly to end effectors and stapling devices and methods of using those devices in medical procedures.

BACKGROUND

Obesity, as a disease, affects a significant portion of the world's population. Obesity often leads to multiple chronic medical conditions and premature death from cardiovascular events and cancer. The U.S. Centers for Disease Control and Prevention ("CDC") reports that over 33% of the U.S. population is obese, with a body mass index ("BMI") of over 30, and another 35-40% of the population is overweight, with a BMI of 25¬30. The CDC reports that the percent of the population being either overweight or obese by 2018 will be 75%. The CDC also reports that obesity directly costs the U.S. economy $147 billion currently, and projects that the costs will approach $315 billion by 2020. The increase in obesity and the financial impact on the local economy is not limited to the United States but impacts many countries throughout the world.

Obesity has environmental, genetic, and behavioral origins but is intractable to most medical and behavioral interventions. Weight loss, or bariatric, surgery seems to be the only effective long-term treatment option for patients with a BMI greater than 35. Despite the 20 million patients who are eligible for weight loss surgery in the United States, the number of procedures per year has plateaued at about 200,000, essentially eliminating any meaningful public health effect of the surgery.

In recent years, laparoscopic vertical sleeve gastrectomy has emerged as a procedure that is safe and effective for patients who are eligible for weight loss surgery. Laparoscopic surgery is a form of minimally invasive surgery inside of the abdominal cavity performed at a distance by the surgeon. Laparoscopic surgery instrumentation is designed to fit through small incisions in the abdominal wall, typically 5 mm to 15 mm in diameter. The abdominal access sites are maintained by cannulae, or trocars, that are designed to maintain pressure in the abdominal cavity with valves that seal around an instrument shaft. Videoscopic guidance may be used throughout the surgery. Since its introduction in 2003 as a stand-alone surgery, vertical sleeve gastrectomy has been studied extensively. It is now widely accepted as the surgery that should be offered to most morbidly obese patients over laparoscopic adjustable gastric banding and laparoscopic Roux-en-Y gastric bypass. The surgery has been adopted by most bariatric surgeons and is now one of the most commonly used procedures to achieve effective weight loss.

During a vertical sleeve gastrectomy, approximately 80% of the stomach is removed and the remaining pouch is based on the less distensible lesser curve of the stomach. The fundus of the stomach, which is formed by the upper curvature of the organ, is the most crucial portion of the stomach that is removed. The resultant gastric pouch generally should be about 80 mL to about 820 mL in volume, should not be narrowed at the incisura angularis, should be as straight as possible to avoid obstruction from spiraling or zigzagging, should be about 0.5 cm to about 2 cm away from the gastro esophageal junction, and should be about 2 cm to about 10 cm away from the pylorus.

A vertical sleeve gastrectomy is typically performed using standard laparoscopic equipment. The greater curvature of the stomach is mobilized by using vessel-sealing devices to seal the gastric branches of the gastro epiploic vessels and the short gastric vessels. The posterior adhesions of the stomach are also divided so the stomach is fully mobilized while the blood supply to the lesser curvature remains intact. The left crus of the diaphragm is an important landmark to ensure the fundus has been fully mobilized.

Following mobilization of the stomach and repair of any hiatal hernia that may be present, a calibration tube or bougie is typically introduced into the stomach through the mouth. The bougie is inserted through the mouth, down the esophagus, and into the stomach, where it is used as a point of reference in order to help align the initial staple fire. The bougie acts as a left-hand landmark, which the surgeon uses to visualize the path of the staple line. A surgeon creating a sleeve gastrectomy staple line will estimate 2.0 cm away from the lesser curvature of the stomach and visually orient the stapler. As constant diameter bougies cannot be used to facilitate orienting the stapler, only surgeon experience and estimation is used. At the top of the staple line, it is important to not divide part of the esophagus or the 'sling fibers' of the cardia, which participate in the physiologic anti-reflux action of the lower esophageal sphincter. Surgeons must use visual cues to ensure that the staple line is a safe distance away from the gastro esophageal junction.

Resection is accomplished by a series of applications of a laparoscopic linear surgical stapler, which are also referred to as endocutter surgical staplers. The staplers that are most commonly used for sleeve gastrectomy are no more than 60 mm in length and include an integrated cutting blade, an anvil, and a cartridge, where the anvil and cartridge are parallel in the longitudinal direction. Conventional endocutter staplers have double or triple staggered rows of staples on either side of the cutting blade. Each staple application places two or three staggered rows of staples into the tissue on either side of the cutting blade. For sleeve gastrectomy, the average number of staple fires per procedure is 3 to 7 in order to create a continuous resection line. This results in a resection line that is about 15 cm to about 37 cm on average.

Proper alignment between the anvil and cartridge is very important during staple formation. Surgical staplers must have alignment in the x, y, and z axes to be able to form B-shaped staples. The alignment of the anvil and cartridge must be maintained along the length of the stapler. The anvil may be deflected during staple formation due at least in part to the forces of tissue and staple formation on the anvil. This deflection has limited the lengths of staplers. More specifically, the longer the stapler is, the more the tip of the stapler tends to deflect. This often results in a gap that is too wide to form staples appropriate for the thickness of the tissue to be stapled.

Currently, surgeon training, experience, and trial and error are the only tools used to aid the surgeon in determining the path of the resection line in a vertical sleeve gastrectomy. Only after applying the stapler to begin creating the resection line is the resultant stomach anatomy demonstrated. Before beginning stapling, the surgeon must attempt to envision the resultant anatomy of the stomach. Further, the surgeon must actively and accurately control the stapler during the resection to produce the desired resection line. Because the thickness of the stomach tissue varies at the antrum, the body, and the fundus, different staple leg lengths are typically used. This requires the stapler to be removed from the patient between firings to load the stapler with a new cartridge having staples with an appropriate leg length. Generally, one or more applications of cartridges including staples with a longer closed leg length are followed by one or more applications of cartridges including staples with a shorter closed leg length. This serial cartridge application can lead to a less than optimal anatomic appearance of the segmented staple line, such as a "zig-zagging" or spiraling line.

There is wide variability in the size and type of calibration tube, or bougie, used by surgeons to size the remaining gastric sleeve. Some surgeons use an endoscope (30 French or 1 cm in diameter) while others use a large mercury-weighted bougie (60 French or 2 cm in diameter). In a large meta-analysis, there was no difference in weight loss when bougie sizes of less than 40 and greater than 40 were used. The resection line is important in sleeve gastrectomy because the amount of weight loss and subsequent medical complications may be a direct result of the quality of the resultant anatomy. The resultant anatomy is determined by the staple line created by the surgeon during the gastrectomy. Negative consequences related to the quality of the staple line may include, for example, gastro esophageal reflux, weight loss failure, weight regain, food intolerance, resection line bleed, and leak.

Leaks are the most concerning complication of a vertical sleeve gastrectomy. In large pooled databases, the leak rate is approximately 0.3 to 2%. Leak is thought to be prevented by making a straight staple line that avoids crossing cartridge applications, has no narrow segments (particularly at the incisura angularis), is about 1 cm from the gastro esophageal junction, and has a squared-off final application. Generally speaking, leak is not prevented by sewing over the staple line or using staple line buttress material in the resection line. Leak is thought to be more a result of poor resultant stomach anatomy. Poor anatomy is a direct result of the shortcomings of the calibration equipment and technique used to create the staple line. Conventional calibration tubes specifically designed for use in a sleeve gastrectomy may provide some user benefits, but fail to reliably produce the proper geometry of the resultant anatomy from the vertical sleeve gastrectomy.

Accordingly, new apparatuses and methods are needed to address the shortcomings of existing apparatuses and methods. More particularly, improved apparatuses and methods are needed that improve the consistency and quality of the staple line created during a medical procedure, such as a vertical sleeve gastrectomy.

SUMMARY

An end effector for use by a surgeon to staple an anatomical structure of a patient during a surgical procedure addresses these and other shortcomings and, in one embodiment, the anatomical structure has a first side and a second side and the end effector includes an anvil that includes a first end, a second end, and a face that is positionable on the first side of the anatomical structure. The end effector further includes a cartridge that is configured to house a plurality of staples and that includes a first end, a second end, and a face that is positionable on the second side of the anatomical structure. The first end of the cartridge is movably coupled to the first end of the anvil, and the second end of the cartridge is movably coupled to the second end of the anvil. The anvil is movable relative to the cartridge to define a first gap between the faces at the first ends that is less than a second gap between the faces at the second ends.

In one embodiment, the decrease from the first gap to the second gap is determined by an angle of from about 0.1° to about 1°.

In one embodiment, the first gap is from about 1.5 mm to about 3.3 mm.

In one embodiment, the second gap is from about 2.0 mm to about 5.0 mm.

In one embodiment, the first ends define a distal end of the end effector and the second ends define a proximal end of the end effector.

In one embodiment, the end effector further includes a shim having a wedge-shape coupled to the face of at least one of the anvil and the cartridge and defining at least one of the first gap and the second gap.

In one embodiment, each face defines a width and the shim extends the width of at least one of the faces.

In one embodiment, a thickness of the shim varies across a width of the shim.

In one embodiment, the end effector further includes a shim having a wedge-shape coupled to the face of at least one of the anvil and the cartridge and defining each of the first gap and the second gap.

In one embodiment, the end effector further includes a shim that is coupled to the face of at least one of the anvil and the cartridge, the shim having a first end, a second end, and a thickness, the thickness of the shim at the first end being different than the thickness of the shim at the second end.

In one embodiment, at least one of the faces of the anvil and the cartridge has a stepped configuration including at least two segments that are offset from one another. One segment defines the first gap and the other segment defines the second gap.

In one embodiment, the cartridge includes a plurality of staples and an open leg length of each of the staples in each segment is the same.

In one embodiment, the cartridge includes staples each having an open leg length and the open leg length of one staple in one segment is different from the open leg length of one staple in the other segment.

In one embodiment, the cartridge includes a plurality of staple drivers each having a height and the height of at least two staple drivers are different in a direction from the first end to the second end of the cartridge.

In one embodiment, the cartridge includes staples, each staple having an open leg length, the open leg length of at least one staple is different from the open leg length of another staple along a length of the cartridge from the first end to the second end.

In one embodiment, the open leg lengths of the staples are randomly distributed.

In one embodiment, a distribution of the open leg lengths of the staples is based on a probable tissue thickness along the anatomical structure from the first end to the second end.

In one embodiment, the staples are divided into at least two zones of staples. The staples are arranged in at least one row and at least one column in each zone. The open leg length of one staple in one zone differs from the open leg length of another staple in the other zone.

In one embodiment, the cartridge has a first edge and a second edge and one staple in the zone adjacent the first edge has a greater open leg length than another staple in the zone adjacent the second edge.

In one embodiment, the cartridge includes a plurality of staples divided into at least two zones, and a crown length of one staple in one zone differs from a crown length of another staple in the other zone.

In one embodiment, the cartridge includes a plurality of staples divided into at least two zones of staples, and a gauge of one staple in one zone differs from a gauge of another staple in the other zone.

In one embodiment, the cartridge includes a plurality of magazines configured to be selectively inserted and removed from the cartridge, each magazine including a plurality of staples arranged in one or more rows and one or more columns.

In one embodiment, a length of at least one magazine is from about 5 mm to about 250 mm.

In one embodiment, at least one magazine includes a channel for a cutting blade with at least one column of staples on each side of the channel.

In one embodiment, the magazines include an interlock feature.

In one embodiment, the interlock feature includes a projection on one of the magazines and a recess on another of the magazines, the projection being configured to be received in the recess when the magazines are adjacent to each other in the cartridge.

In one embodiment, the cartridge includes a plurality of staples arranged in rows and columns, each staple having an open leg length, the staples in each column having about the same open leg length. Each of the anvil and the cartridge has a first edge and a second edge, the anvil being movable relative to the cartridge to define a first edge gap between the faces at the first edges that is less than a second edge gap between the faces at the second edges.

In one embodiment, the end effector further includes an alignment mechanism configured to facilitate alignment between the anvil and the cartridge as the anvil is moved toward the cartridge.

In one embodiment, the alignment mechanism includes a knife that is partially housed in the cartridge and that has a first flange, a second flange, and a web connecting the first and second flanges and including a cutting edge. The alignment mechanism further includes a recess in the anvil face that is configured to receive the first flange. The alignment mechanism further includes a first slot in the anvil that is open to the anvil face and to the recess and that is configured to slidably receive the web during cutting of the anatomical structure with the cutting edge and a second slot in the cartridge that is open to the cartridge face and that is configured to slidably receive the web during cutting of the anatomical structure.

In one embodiment, the anvil has a first guide channel open to the first slot, the cartridge has a guide channel open to the second slot, and the first and second guide channels are parallel.

In one embodiment, the anvil face and the cartridge face are not parallel.

In one embodiment, at least one of the anvil face and the cartridge face has a stepped configuration including at least two segments that are offset from one another, one segment defines the first gap and the other segment defines the second gap.

In one embodiment, one of the first and second flanges has a V-shaped cross-section.

In one embodiment, the staples have two legs and a crown having a midline and the staple pockets are configured to bend the two legs past the midline of the crown when the end effector is actuated.

In one embodiment, each of the anvil and the cartridge has a first edge and the end effector further includes a spacer coupled to the first edge of at least one of the anvil and the cartridge and being configured to abut an anatomical feature to space the end effector apart from the anatomical feature by a known distance.

In one embodiment, the end effector is insertable through a trocar.

In one embodiment, the end effector further includes a flexible member that movably couples the first end of the anvil to the first end of the cartridge.

In one embodiment, at least one of the anvil and the cartridge slidably receives the flexible member when the end effector is clamped on to the anatomical structure.

In one embodiment, the flexible member is anchored to the anvil.

In one embodiment, the flexible member is anchored to the cartridge.

In one embodiment, the end effector further includes a tensioning device operable by the surgeon for selectively tensioning the flexible member to provide at least a portion of the clamping force on the anatomical structure.

In one embodiment, each of the anvil and the cartridge is insertable through a trocar and the end effector is remotely operable from outside the patient to clamp the end effector to the anatomical structure according to the first gap and the second gap A stapling device for use by a surgeon to staple an anatomical structure of a patient during a surgical procedure, in one embodiment, the anatomical structure has a first side and a second side and the endocutter stapling device includes an end effector and a manipulator that is configured to be accessible to the surgeon outside of the patient and that includes a shaft coupled to the end effector and a clamping mechanism for selectively moving the anvil and the cartridge toward one another to clamp the anatomical structure. The device further includes a flexible member that extends through the shaft to the end effector and is operably coupled to at least one of the anvil and the cartridge and to the clamping mechanism such that operating the clamping mechanism withdraws the flexible member from the end effector and clamps the anatomical structure between the anvil and the cartridge.

In one embodiment, the clamping mechanism is capable of selectively tensioning the flexible member to clamp the anvil and the cartridge to the anatomical structure with a first stage clamping force that permits the end effector to be repositioned relative to the anatomical structure.

In one embodiment, the first stage clamping force is between about 0.1 g/mm2 and about 4 g/mm2.

In one embodiment, the clamping mechanism is capable of selectively tensioning the flexible member to clamp the anvil and the cartridge to the anatomical structure with a second stage clamping force that substantially prevents the end effector from moving relative to the anatomical structure during the medical procedure.

In one embodiment, the second stage clamping force is between about 4 g/mm2 and about 70 g/mm2.

In one embodiment, the manipulator includes a handpiece that at least partially houses the clamping mechanism, the clamping mechanism further includes a lever that is pivotable relative to the handpiece and is operable to activate the clamping mechanism.

In one embodiment, the clamping mechanism includes a first push bar that is pivotably coupled to the lever, a second push bar that is pivotably coupled to the first push bar, and a pin that is coupled to the second push bar, the flexible member extending around the pin. Rotation of the lever relative to the handpiece moves the pin and withdraws the flexible member from the end effector In one embodiment, the manipulator includes a stapling mechanism that has an actuator coupled to an actuator plate that is slidable relative to the end effector and at least one wedge coupled to the actuator plate. Activating the actuator slides the actuator plate and the at least one wedge in the direction of the end effector to force the wedge into engagement with staples.

In one embodiment, the actuator is a thumb plate.

In one embodiment, the manipulator includes a cutting mechanism that is configured to cut the anatomical structure and is coupled to the actuator plate and, when the actuator is engaged, the stapling mechanism begins stapling the anatomical structure prior the cutting mechanism cutting the anatomical structure.

An end effector for use by a surgeon to staple an anatomical structure of a patient during a surgical procedure, in one embodiment, the anatomical structure has a first side and a second side and the end effector includes an anvil that includes a first end, a second end, a face that is positionable on the first side of the anatomical structure, and a first edge. The end effector further includes a cartridge that is configured to house a plurality of staples and that includes a first end, a second end, a face that is positionable on the second side of the anatomical structure, and a first edge. The first end of the cartridge is movably coupled to the first end of the anvil. The end effector further includes a spacer configured to be coupled to the first edge of at least one of the anvil and the cartridge.

An end effector for use by a surgeon to staple an anatomical structure of a patient during a surgical procedure, in one embodiment, the anatomical structure having a first side and a second side and the end effector includes an anvil that includes a first end, a second end, a face that is positionable on the first side of the anatomical structure, the face defining a width, a first edge, and a second edge. The end effector further includes a cartridge that includes a plurality of staples arranged in rows and columns, each staple having an open leg length, the staples in each column having about the same open leg length, a first end, a second end, and a face that is positionable on the second side of the anatomical structure, the face defining a first edge, a second edge, and a width between the first edge and the second edge. The first end of the cartridge is movably coupled to the first end of the anvil, the anvil being movable relative to the cartridge to define a first edge gap between the faces at the first edges that is less than a second edge gap between the faces at the second edges. When the end effector is positioned on the anatomical structure, the first edge gap linearly increases to the second edge gap.

An end effector for use by a surgeon to staple an anatomical structure of a patient during a surgical procedure, in one embodiment, the anatomical structure having a first side and a second side and the end effector includes an anvil that includes a first end, a second end, a face that is positionable on the first side of the anatomical structure, the face defining a width, and a first edge. The end effector further includes a cartridge that is configured to house a plurality of staples and that includes a first end, a second end, a face that is positionable on the second side of the anatomical structure, the face defining a width, and a first edge. The first end of the cartridge is movably coupled to the first end of the anvil. The end effector further includes a shim that is coupled to the face of at least one of the anvil and the cartridge, the shim having a first edge, a second edge, and a thickness, the thickness of the shim at the first edge being different than the thickness of the shim at the second edge.

In one embodiment, the shim extends the width of at least one of the faces.

In one embodiment, a thickness of the shim varies across the width of the shim.

An end effector for use by a surgeon to staple an anatomical structure of a patient during a surgical procedure, in one embodiment, the anatomical structure has a first side and a second side and the end effector includes an anvil that includes a first end, a second end, a face that is positionable on the first side of the anatomical structure. The end effector further includes a cartridge that includes a plurality of staple channels arranged in one or more rows and one or more columns, is configured to house a plurality of staples individually in the staple channels, and that includes a first end, a second end, and a face that is positionable on the second side of the anatomical structure, the rows extending from the first end toward the second end. The first end of the cartridge is movably coupled to the first end of the anvil. The end effector further includes a shim that is coupled to the face of at least one of the anvil and the cartridge, the shim covering less than all of the rows of the staple channels.

A cartridge for use in an end effector having an anvil, the end effector being for use by a surgeon to staple an anatomical structure of a patient during a surgical procedure, in one embodiment, the anatomical structure has a first side and a second side and the cartridge includes a cartridge body defining a plurality of staple channels. The cartridge further includes a plurality of staples arranged in rows and columns, each staple having an open leg length and a crown and being housed in one of the staple channels. The open leg length of one of the staples differs from the open leg length of another of the staples in a longitudinal direction along the rows. The open leg length of the staples is selected based on a probable tissue thickness along the anatomical structure from the first end to the second end.

In one embodiment, the cartridge body is divided into at least two zones, each zone having a plurality of staples arranged in at least one row and at least one column, each staple having an open leg length. The open leg length of one staple in one zone differs from the open leg length of one staple in the other zone.

In one embodiment, the cartridge includes a plurality of magazines configured to be selectively inserted and removed from the cartridge, each magazine including a plurality of staples arranged in one or more rows and one or more columns.

In one embodiment, a length of at least one magazine is from about 5 mm to about 250 mm.

In one embodiment, at least one magazine includes a channel for a cutting blade with at least one column of staples on each side of the channel.

In one embodiment, the magazines include an interlock feature.

In one embodiment, the interlock feature includes a projection on one of the magazines and a recess on another of the magazines, the projection being configured to be received in the recess when the magazines are adjacent to each other in the cartridge.

A method of stapling an anatomical structure during a surgical medical procedure, in one embodiment, includes In one embodiment, inserting the end effector of claim 1 through a trocar into a patient adjacent the anatomical structure, the cartridge including a plurality of staples, positioning the anvil and the cartridge on opposing sides of the anatomical structure, clamping the end effector to the anatomical structure at the first ends of the anvil and the cartridge and the second ends of the anvil and the cartridge to secure the position of the end effector relative to the anatomical structure, and actuating the end effector to staple the anatomical structure.

In one embodiment, the method further includes positioning a clamp adjacent to the anatomical structure, and wherein positioning the anvil and the cartridge includes positioning at least one of the anvil and cartridge adjacent the clamp.

In one embodiment, the staples having an open leg length are arranged in rows and columns and the open leg length of each of the staples is the same in each column, and actuating the end effector includes forming a first row of staples and a second row of staples, the staples in the first row having a greater closed leg length than the staples in the second row.

In one embodiment, each of the anvil and the cartridge have a first edge and a second edge and clamping the end effector to the anatomical structure includes compressing the anatomical structure more at the first edges than at the second edges.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

FIGS. 37A and 37B are an elevation view and a plan view, respectively, of a staple according to one embodiment of the present invention.

FIGS. 38A and 38B are an elevation view and a plan view, respectively, of a staple according to one embodiment of the present invention.

FIGS. 39A and 39B are a cross-sectional view and a plan view, respectively, of a staple pocket according to one embodiment of the present invention.

FIGS. 40A and 40B are a cross-sectional view and a plan view, respectively, of a staple pocket according to one embodiment of the present invention.

DETAILED DESCRIPTION

In its broadest aspects, embodiments of the present invention are directed to a stapler for creating a staple line during a surgical procedure involving the resection of at least a part of an anatomical structure. For example, the stapler may be used in a vertical sleeve gastrectomy procedure. The stapler may be a supplement to current practices of a sleeve gastrectomy, including the laparoscopic access and mobilization of the greater curvature of the stomach. As is described in detail below, embodiments of the stapler account for variations in thickness of the tissue and, in doing so, are believed to provide a staple line of improved integrity.

While embodiments discussed below involve the use of a stapler to create a staple line during a medical procedure, it should be recognized that the stapler may act as a surgical clamp independent of its use as stapler. Further, while embodiments discussed below involve the use of the stapler in a vertical sleeve gastrectomy procedure, the stapler may also be adapted for use in other procedures involving anatomical structures, such as organs other than the stomach or soft tissue. For example, the stapler may be used in a parenchymal resection, lung volume reduction surgery, or other procedures involving the lung. Further, the stapler may be useful in an anatomic resection such as a lobectomy, a non-anatomic parenchymal resection, or other procedures involving the liver. Moreover, a surgeon or other medical professional may benefit from using the stapler in a partial nephrectomy, total nephrectomy, or other procedures involving the kidney. During procedures involving an anatomical structure, the tissue of the anatomical structure may be sealed. Thus, while aspects of the present invention may be illustrated in the context of a vertical sleeve gastrectomy, it should be appreciated that aspects of the invention may provide a benefit in a host of medical procedures on anatomical structures and be adapted for use in such medical procedures.

Figure 1:
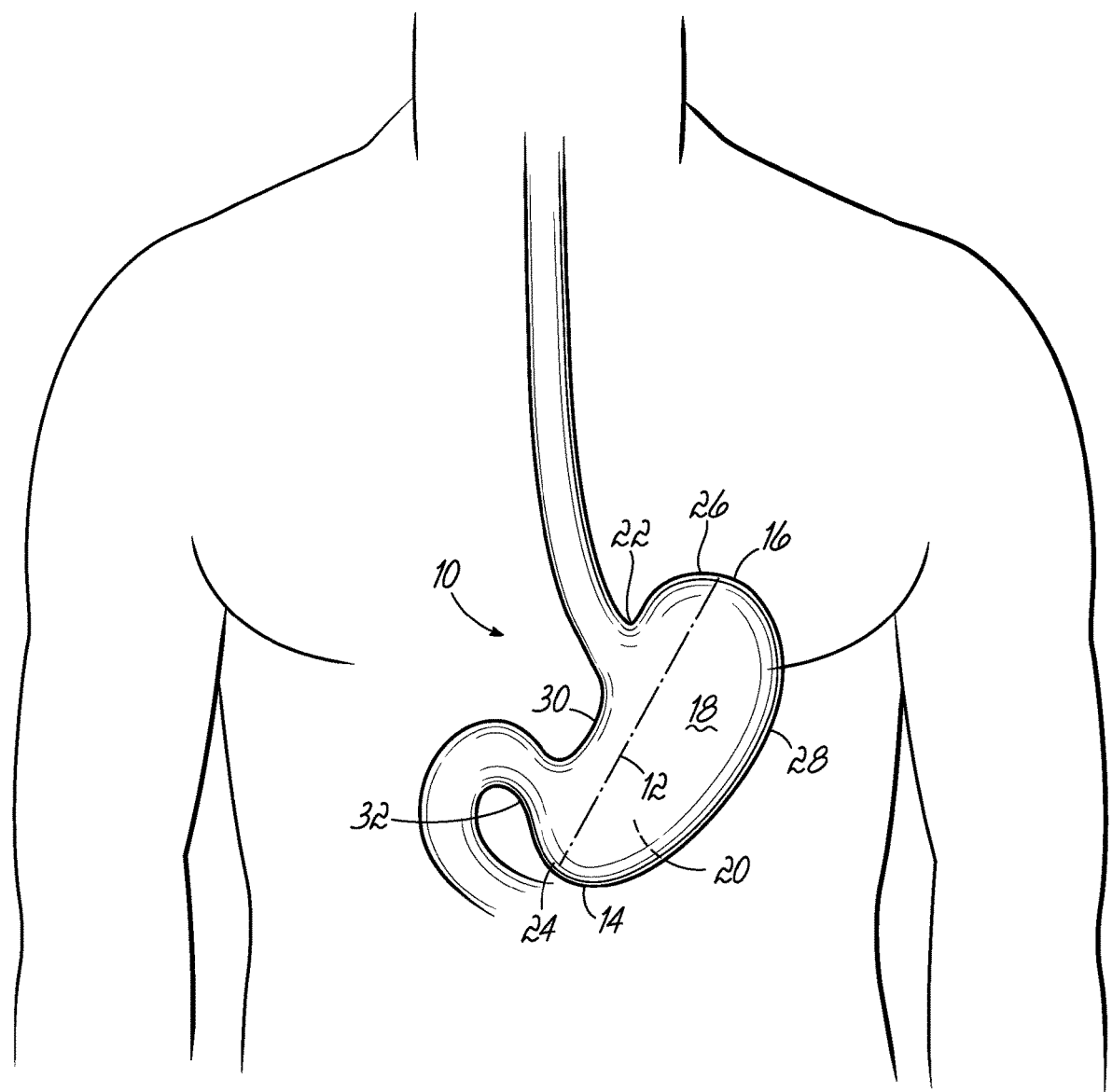
FIG. 1 depicts the anatomy of a stomach.

Now referring to the figures, FIG. 1 illustrates the anatomy of a stomach 10 and a staple line 12, where the staple line 12 represents a resection line for a vertical sleeve gastrectomy. The stomach 10 generally includes a proximal end 14, a distal end 16, an anterior side 18, and a posterior side 20. As used herein, the proximal and distal ends 14, 16 of the stomach 10 are described from the perspective of the operative surgeon. A gastro esophageal junction 22 opens into the stomach 10 and is a common landmark in bariatric surgeries. An antrum 24 and a fundus 26 are located adjacent the proximal and distal ends 14, 16 of the stomach 10, respectively. The thickness of the stomach 10 generally increases from the fundus 26 to the antrum 24. The thickness of the stomach may also vary based on other factors. For example, male stomachs tend to have a greater thickness than female stomachs. Further, patients with a higher body mass index ("BMI") tend to have stomachs with a greater thickness than stomachs of patients with a lower BMI. The staple line 12 therefore traverses the stomach 10 over a portion in which the thickness of the tissue changes. The fundus 26 and the section of the stomach 10 defined by the greater curvature 28 are generally the parts of the stomach 10 removed during a vertical sleeve gastrectomy. The desired location of the staple line 12 is about 0.5 cm to about 2 cm away from the gastro esophageal junction 22 and about 2 cm to about 10 cm away from the pylorus 32.

Following the gastrectomy, the remaining pouch is generally defined by a lesser curvature 30 and the staple line 12 and presents a stomach with a significantly reduced volume. In accordance with aspects of the invention, staplers as described herein aid in forming high quality, consistent staple lines during a medical procedure, such as a vertical sleeve gastrectomy. In this regard, the staplers provide an accurate visual indication of the staple line before the stapler has been actuated. The visualization aspect of the disclosed staplers is believed to result in high quality and consistent staple lines that are significantly improved over staple lines produced by current methodologies. Furthermore, unlike the prior art, embodiments of the stapler account for tissue thickness variation, such as, thickness variations associated with the staple line 12, during clamping and/or stapling which is also believed to result in high quality and consistent staple lines.

Figure 2A:
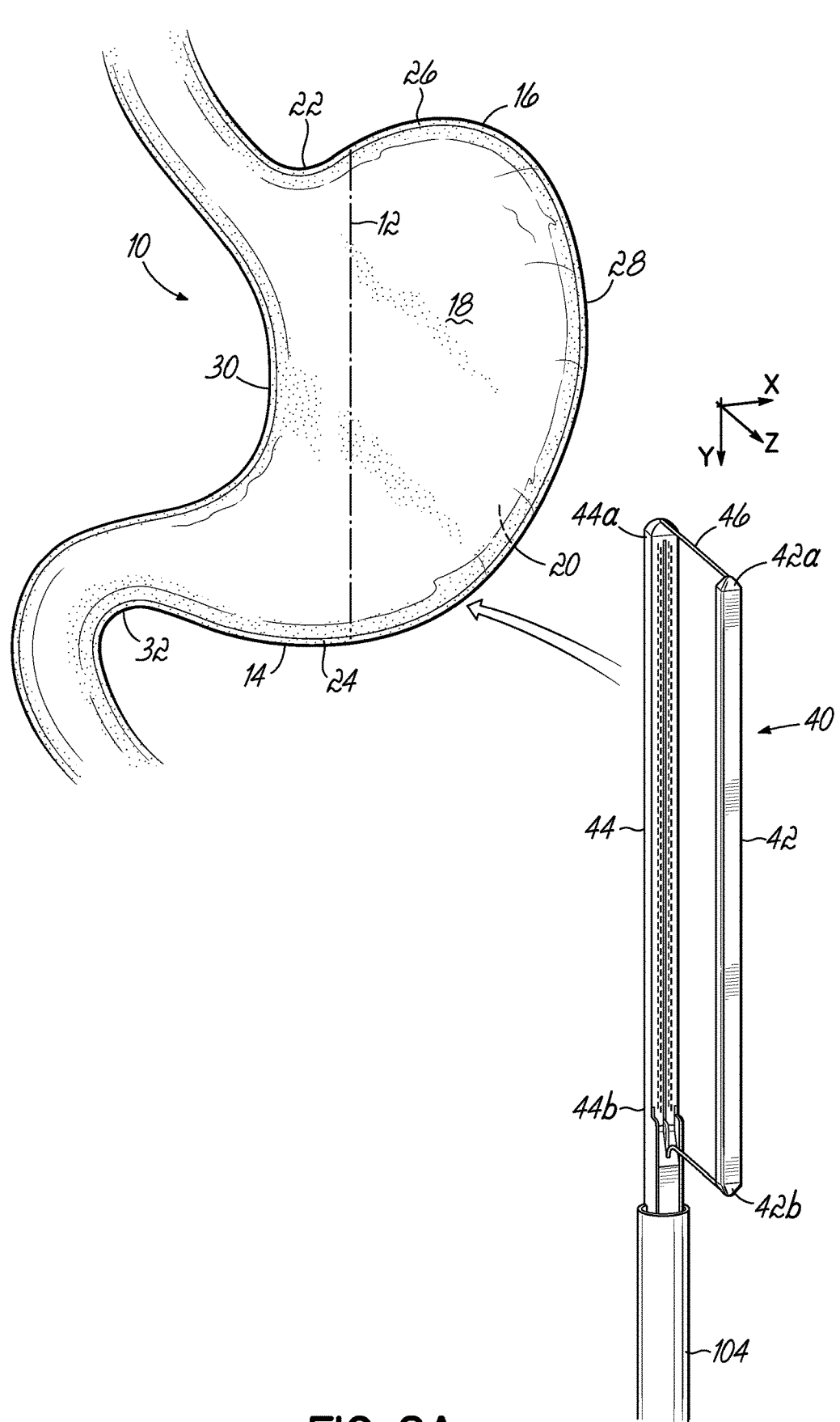
FIG. 2A is an elevation view of an end effector of an endocutter stapling device according to one embodiment of the invention.

To these and other ends, and with reference to FIG. 2A, embodiments of the present invention may include an end effector 40 having an anvil 42 and a cartridge 44 coupled to one another. As is described below in reference to FIGS. 2B-2E, the surgeon may forcibly drive the anvil 42 and the cartridge 44 toward one another to clamp the stomach 10 between the anvil 42 and the cartridge 44. The surgeon may close the anvil 42 and the cartridge 44 remotely from the end effector 40. That is, no direct manual access to the end effector 40 is required. For this reason, the end effectors, as disclosed herein, may be designed specifically for use in surgical procedures in which the organ is accessed through a trocar.

According to one aspect, clamping onto the stomach 10 permits the surgeon to be able to accurately position the end effector 40 and ensures creation of a straight sleeve gastrectomy pouch. In the exemplary embodiment, and with reference to FIG. 2B, the anvil 42 may be generally positionable on the anterior side 18 of the stomach 10, and the cartridge 44 may be generally positionable on the posterior side 20 of the stomach 10. The cartridge 44 may house a plurality of surgical staples and a knife, each described below, for forming the staple line 12. The anvil 42 and the cartridge 44 may be coupled together via a flexible member 46 and collectively operate as clamping members for purposes described below. The present invention is not limited to the illustrated arrangement. For example, the arrangement of the anvil 42 and the cartridge 44 may be reversed such that the anvil 42 is coupled to a shaft and is positioned adjacent the posterior side 20 of the stomach 10 and the cartridge 44 is coupled to the anvil 42 via the flexible member 46 and is positioned on the anterior side 18 of the stomach 10 (not shown). Other alternative arrangements may also be possible depending on the surgical procedure and the surgeon's preference, among other factors. There are many ways to couple the anvil 42 and the cartridge 44 and the invention is not limited to the flexible member shown. By way of example, many of the connection methods described in PCT Application No. PCT/US2014/070869, which is incorporated by reference herein in its entirety, may be utilized to connect the anvil and the cartridge described herein.

Figure 2B:
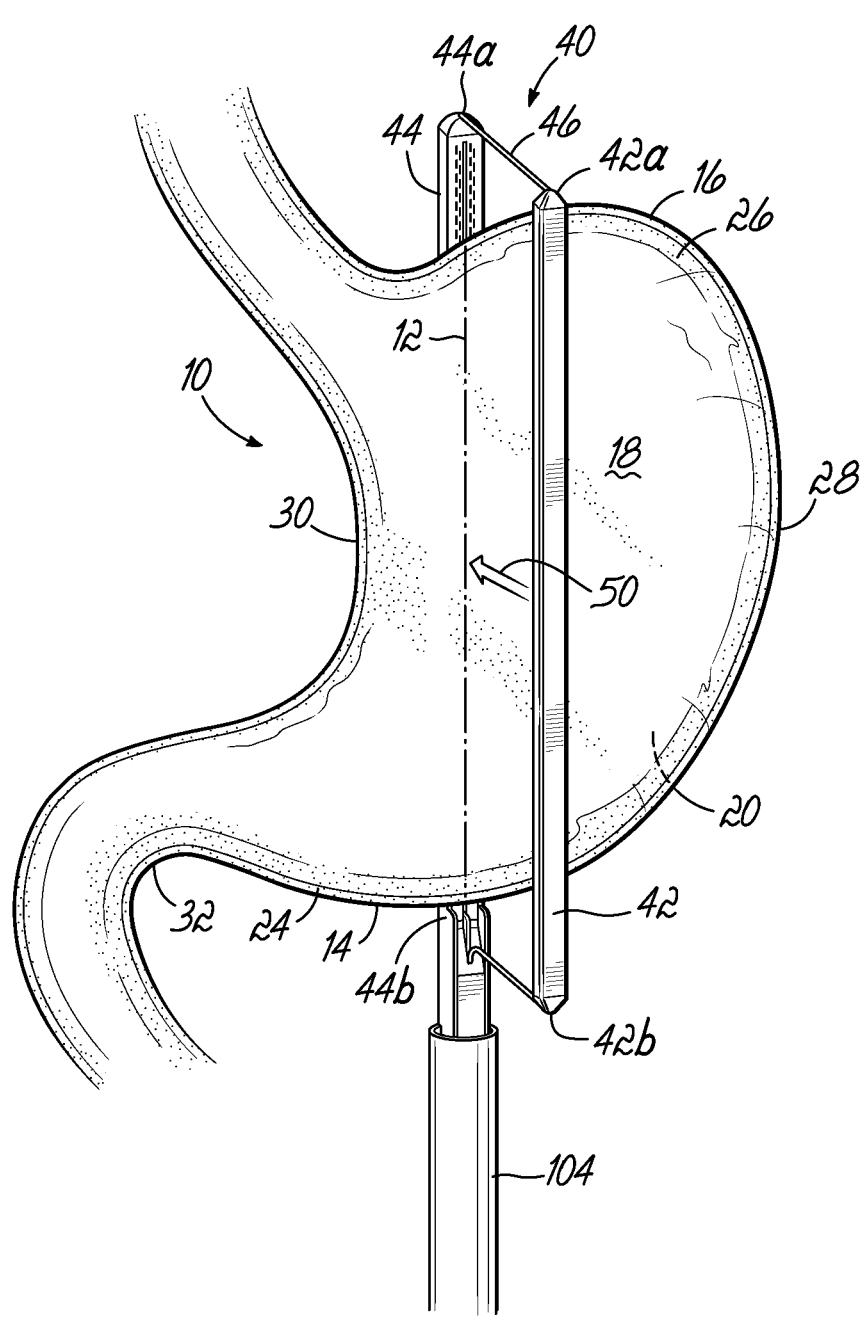
FIG. 2B is an elevation view of the end effector of FIG. 2A positioned on the stomach.

In one embodiment, the surgeon, using standard laparoscopic instruments and graspers, may position the end effector 40 proximate the stomach 10 as is shown in FIG. 2B. In this regard, FIG. 2B illustrates the end effector 40 placed around the stomach 10 with the anvil 42 and the cartridge 44 coupled together with the flexible member 46 at both the proximal end 14 and the distal end 16 of the stomach 10. The length of the anvil 42 and the cartridge 44 may be sufficient for the anvil 42, the cartridge 44, and the flexible member 46 to encircle the stomach 10, as shown. The length of the anvil and/or the cartridge as described herein is not particularly limited. By way of example and not limitation, the length of each may measure from about 35 mm to about 350 mm. The end effector 40 may be put in place and used with or without having to mobilize the greater curvature 28. For example, a surgeon may prefer to leave the greater curvature 28 attached to the omentum (not shown), which could improve stability of the stomach 10 during stapling.

As is described below, the flexible member 46 may be coupled to a tensioning mechanism by which the anvil 42 and the cartridge 44 may be moved toward one another and to provide a sufficient clamping force on the stomach 10. Once the end effector 40 is properly positioned, as is shown in FIG. 2B, the surgeon may then engage the tensioning mechanism, described below, to compress the anvil 42 and the cartridge 44 on the stomach 10, as is shown by the arrow 50 in FIG. 2B. In this regard, the end effector 40 may be coupled to a device that houses the tensing mechanism for tensioning the flexible member 46. As the anvil 42 and the cartridge 44 are brought together, the flexible member 46 may align the anvil 42 with the cartridge 44. In this regard, the end effectors disclosed herein may be self-aligning due, in part, to coupling of the anvil 42 to the cartridge 44 at each end. Tensioning the flexible member 46 may also compress the tissue. For instance, as the flexible member 46 is tensioned, the distance between the anvil 42 and the cartridge 44 decreases, and ultimately compresses the stomach 10. In accordance with embodiments of the invention, a gap between the anvil 42 and the cartridge 44 may vary when the surgeon clamps the stomach 10. As is described in detail below, the variation in the gap may reflect variation in the thickness of the tissue clamped between the anvil 42 and the cartridge 44.

In one aspect of the invention, the end effector 40 may be positioned relative to the stomach 10 using a two-stage clamping process in which the surgeon operates the tensioning mechanism to clamp the anvil 42 and the cartridge 44 onto the stomach 10. In the first clamping stage, the anvil 42 and the cartridge 44 may be clamped onto the stomach 10 to provide a threshold amount of resistance to unintentional movement of the end effector 40 relative to the stomach 10. For example, the range of clamping pressure in the first stage may be about 0.1 g/mm2 to about 4 g/mm2. While preventing undesirable or unintentional movements of the end effector 40, the surgeon may move the end effector 40 to a desired position relative to the stomach 10 without significant difficulty.

In the second clamping stage, and with the end effector 40 in the desired location relative to the stomach 10, the clamping force of the end effector 40 may be increased to effectively prevent or minimize the end effector 40 from moving relative to the stomach 10. For example, the clamping pressure in the second stage may be about 4 g/mm2 to about 70 g/mm2. In an exemplary embodiment, the clamping pressure in the second stage may be about 8 g/mm2. The upper limit to which the end effector 40 may be clamped is selected so as to avoid any damage to the underlying tissue being clamped but also allow for adequate tissue compression for staple formation. This upper limit may be, for example, about 70 g/mm2. Additionally, the lower limit in the disclosed range of about 4 g/mm2 represents a threshold clamping force below which constitutes the first stage clamping and above which constitutes the second stage clamping. It will be recognized that these values are merely exemplary and the particular values may depend on several factors, including the anatomical structure being clamped. Thus, embodiments of the invention are not limited to the range of values provided herein. In accordance with embodiments of the invention, the gap between the anvil 42 and the cartridge 44 may vary across the longitudinal length of the end effector 40 when the surgeon clamps the stomach 10 in the first and/or second stage.

In an advantageous aspect of the invention, when the end effector 40 is placed on the stomach 10 (e.g., in the first clamping stage as described above), the surgeon has a clear visualization of the intended results of the vertical sleeve gastrectomy prior to actually performing the resection of the stomach 10 at the staple line 12. Hence, the surgeon has an indication of what the resultant stomach shape and volume defined by the lesser curvature 30 and the staple line 12 will likely be prior to stapling and/or cutting the stomach tissue. If the surgeon is not satisfied with the indication of the expected stomach shape and volume, the surgeon may adjust and manipulate the location and the alignment of the end effector 40 prior to stapling and cutting the stomach 10. This is in contrast to current procedures, where the resection line is generally not well visualized prior to activating the stapler. Thus, according to current procedures, the ultimate outcome is less certain. It will be appreciated that the end effector 40 should be positioned such that it does not provide lateral stretching or tension of the stomach 10, which may create an undesirable environment for stapling and cutting. Using the end effector 40 ensures proper alignment of the staple line 12 so that removing the fundus 26 occurs at a safe distance away from both the lesser curvature 30 and the gastro esophageal junction 22. The result is a staple line that is squared off at the fundus 26 of the stomach to prevent or reduce the likelihood of necrotic tissue development.

Figure 2C:
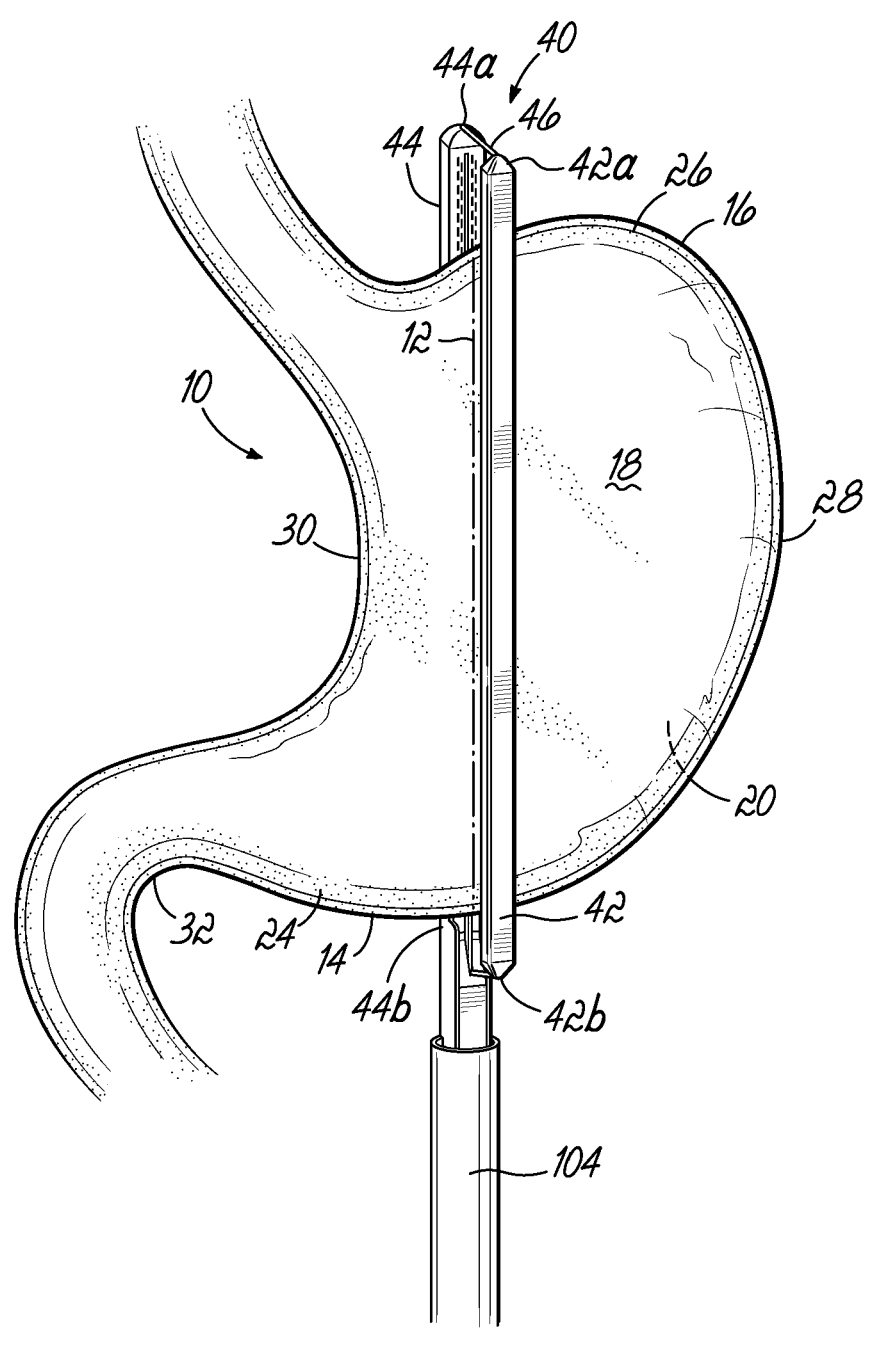
FIG. 2C is an elevation view of the end effector of FIG. 2A during resection of a portion of the stomach.
Figure 2D:
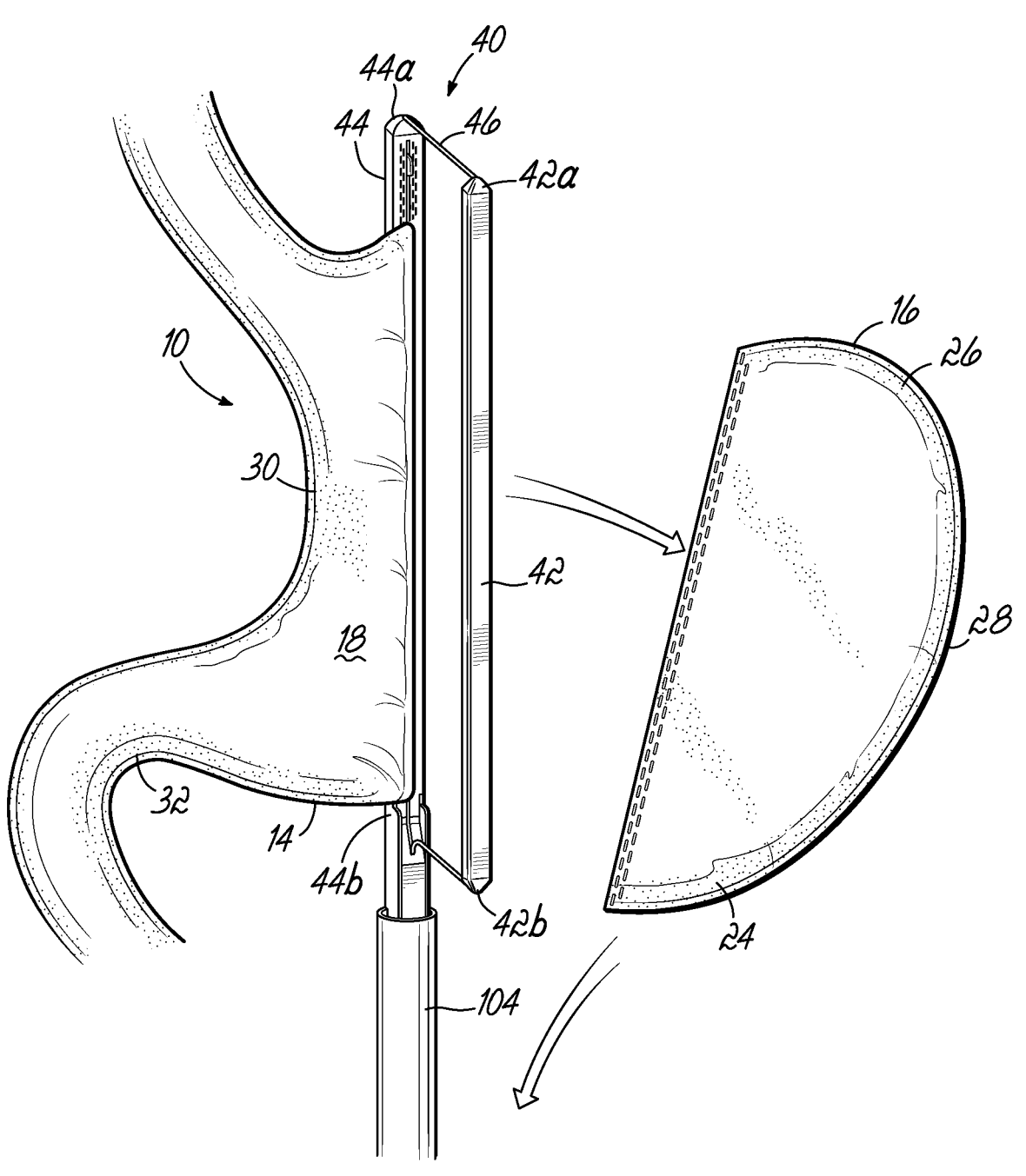
FIG. 2D is an elevation view of the end effector of FIG. 2A following resection of a portion of the stomach.
Figure 2E:
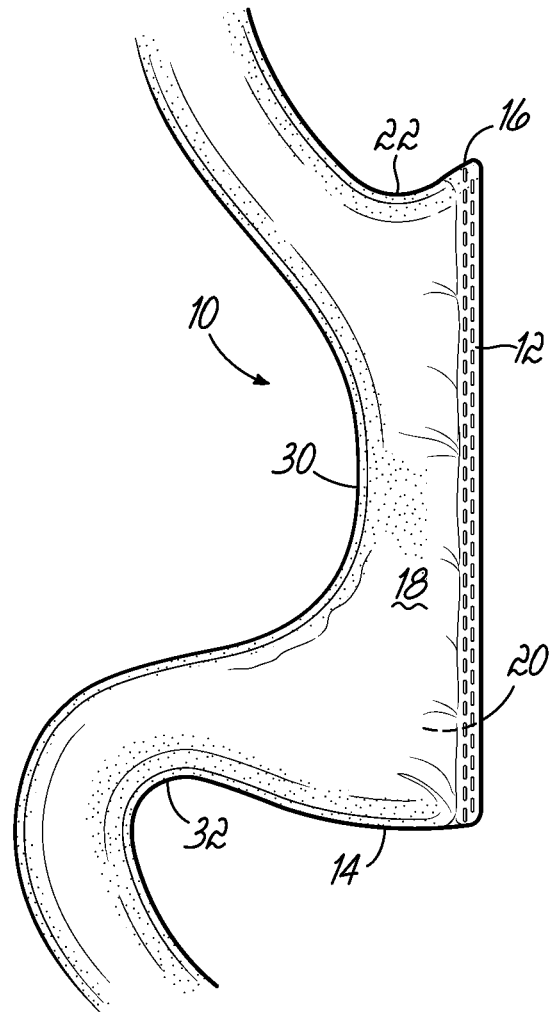
FIG. 2E depicts the stomach anatomy resulting from a vertical sleeve gastrectomy.

Once the end effector 40 is positioned and the anvil 42 and the cartridge 44 are compressed, the surgeon may activate a cutting and stapling mechanism, described below, to cut and staple the tissue using the end effector 40 until complete resection of the stomach 10 occurs, as is illustrated in the sequence of FIGS. 2C, 2D, and 2E. In one embodiment, the surgeon may engage a release mechanism after completing the resection of the stomach 10. This allows slack to be introduced in the flexible member 46 such that the anvil 42 may be separated from the cartridge 44. Consequently, once the anvil 42 and the cartridge 44 are separated, the end effector 40 may be removed from the abdominal cavity.

With reference to FIGS. 3-10D, the surgeon may operate the end effector 40 above, including one or both of the anvil 42 and the cartridge 44, during a vertical sleeve gastrectomy procedure with a mechanical device that is operably coupled to the one or both of the anvil 42 and the cartridge 44. With specific reference to FIG. 3, in one embodiment, an endocutter stapling device 100 includes the end effector 40 operatively coupled to a manipulator 102. With the endocutter stapling device 100, the surgeon may remotely operate the end effectors disclosed herein. While specific reference is made to the endocutter stapling device 100, other stapling devices may be utilized in accordance with the present invention including, for example, the endocutter stapling devices described in commonly owned U.S. Application, which is incorporated by reference herein in its entirety.

Figure 3:
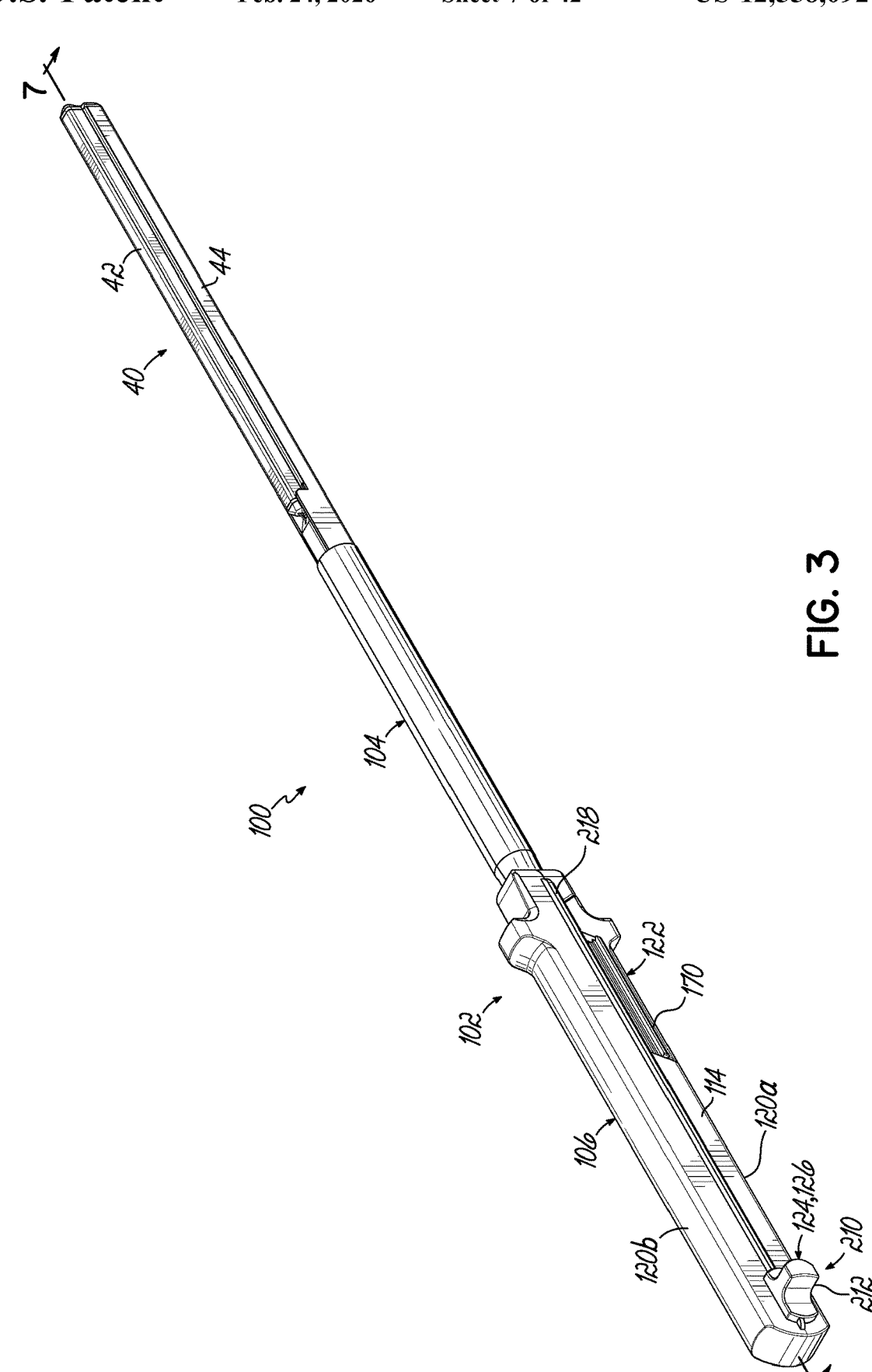
FIG. 3 is a perspective view of an endocutter stapling device according to one embodiment of the invention.

As shown in FIG. 3, the manipulator 102 includes an elongate member or shaft 104 coupled to a handpiece 106 at one end and the end effector 40 at the other end thereof. During a surgical procedure, the end effector 40 and a portion of the shaft 104 may be inserted into the patient, such as via a trocar. The surgeon may then manipulate the end effector 40 and/or articulate the end effector 40 relative to the manipulator 102 to perform a procedure. Thus, embodiments of the present invention may include mechanisms for effectuating a surgical procedure with the end effector 40 (including clamping, stapling, and cutting tissue) and for allowing the end effector 40 to articulate relative to the shaft 104, each described below.

Figure 4:
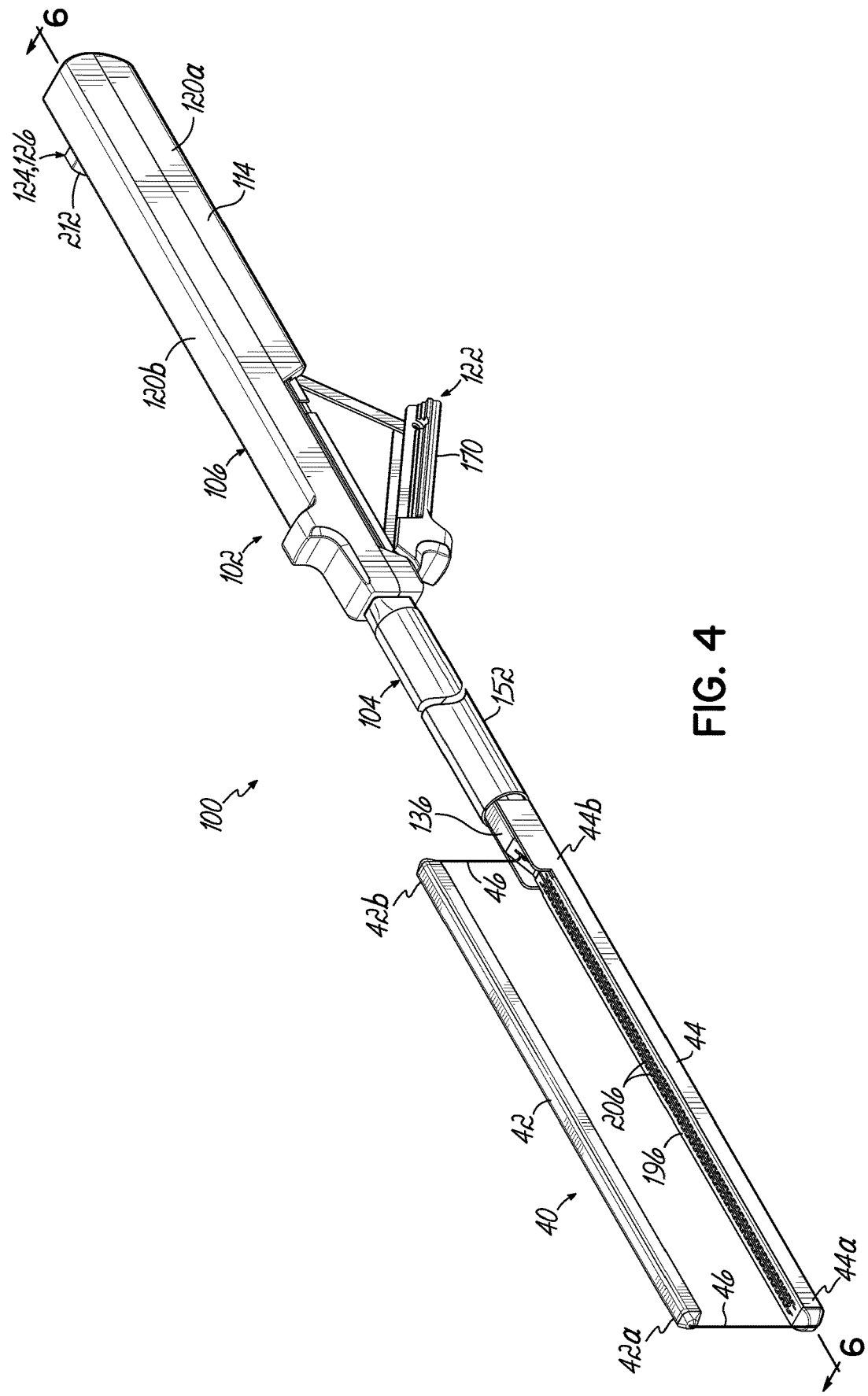
FIG. 4 is a perspective view of the endocutter stapling device of FIG. 3 with an end effector shown in an opened position.
Figure 4A:
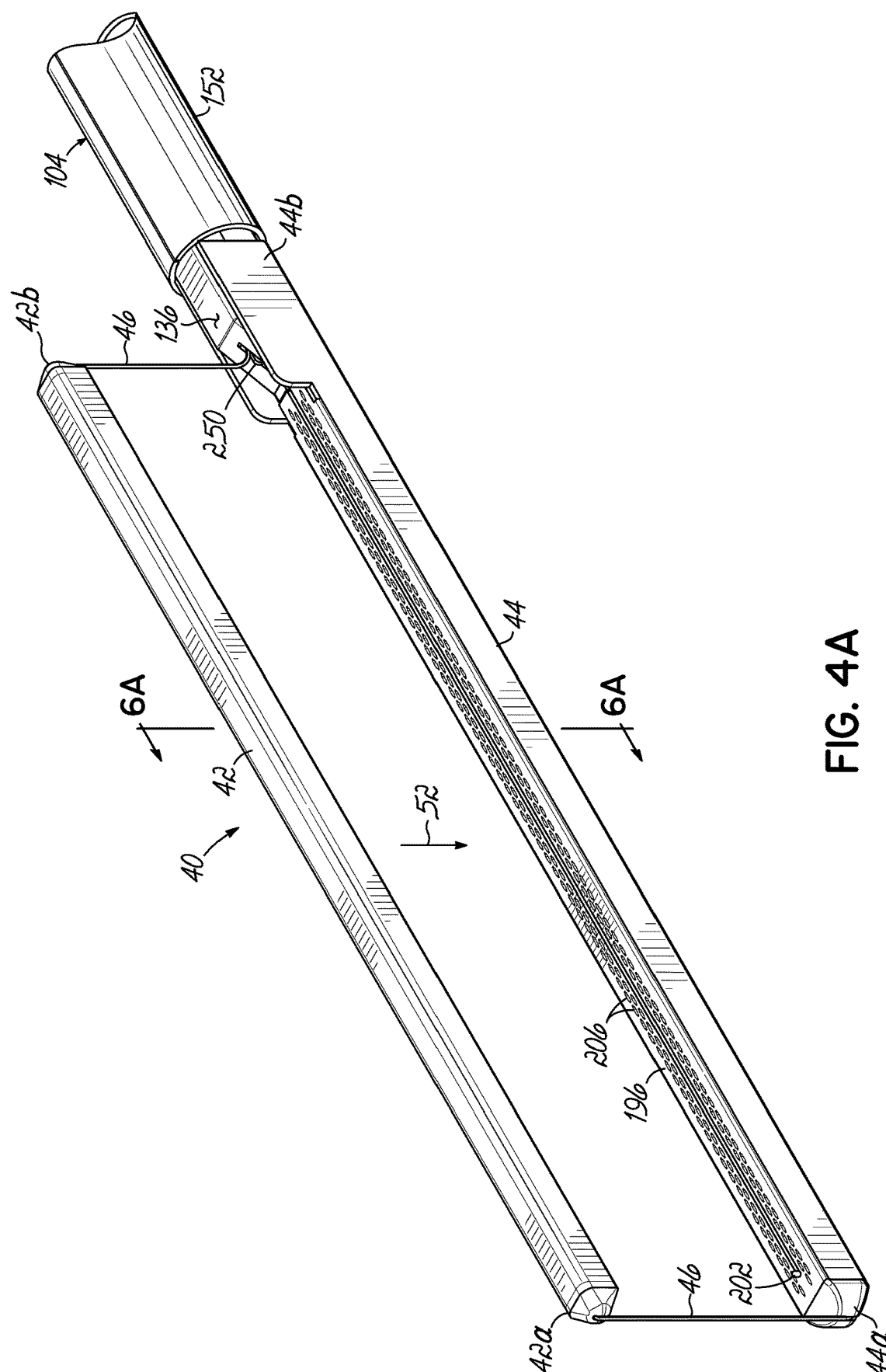
FIG. 4A is an enlarged perspective view of the end effector shown in FIG. 4.

With reference to FIGS. 3, 4, and 4A, the anvil 42 and the cartridge 44 are movably coupled together via the flexible member 46 as is described above. The flexible member 46 passes through hollow portions of the anvil 42 and the cartridge 44 and is movable relative to one or both of the anvil 42 and the cartridge 44. The flexible member 46 may be anchored to one of the anvil 42 or the cartridge 44, as is described below. In the exemplary embodiment shown, the anvil 42 may be separated from or brought closer to the cartridge 44 by extending or retracting the flexible member 46. Retraction of the flexible member 46 moves the anvil 42 toward the cartridge 44 as is shown generally by arrow 52 in FIG. 4A.

Figure 5:
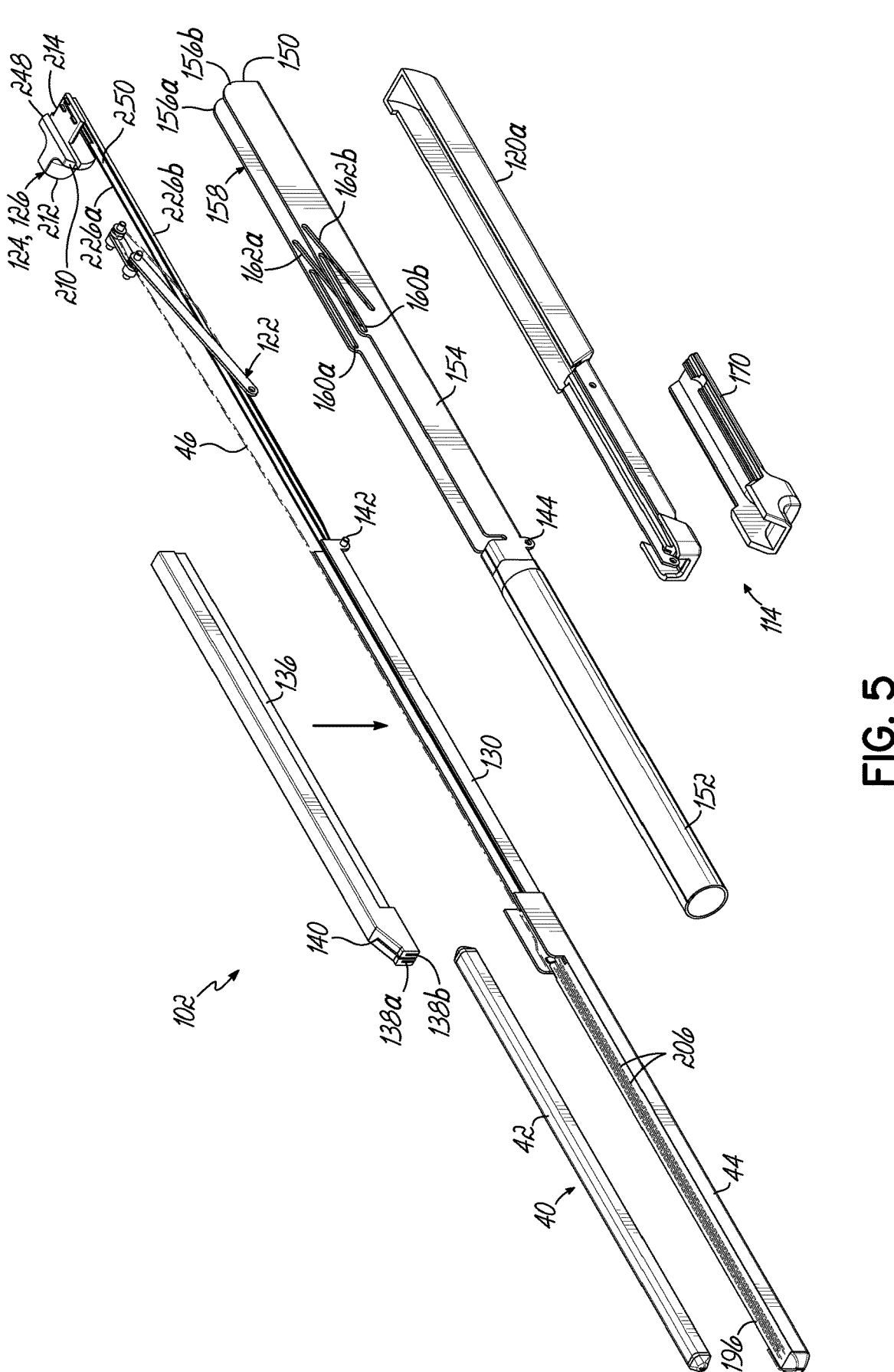
FIG. 5 is a disassembled perspective view of the endocutter stapling device of FIG. 3.
Figure 6:
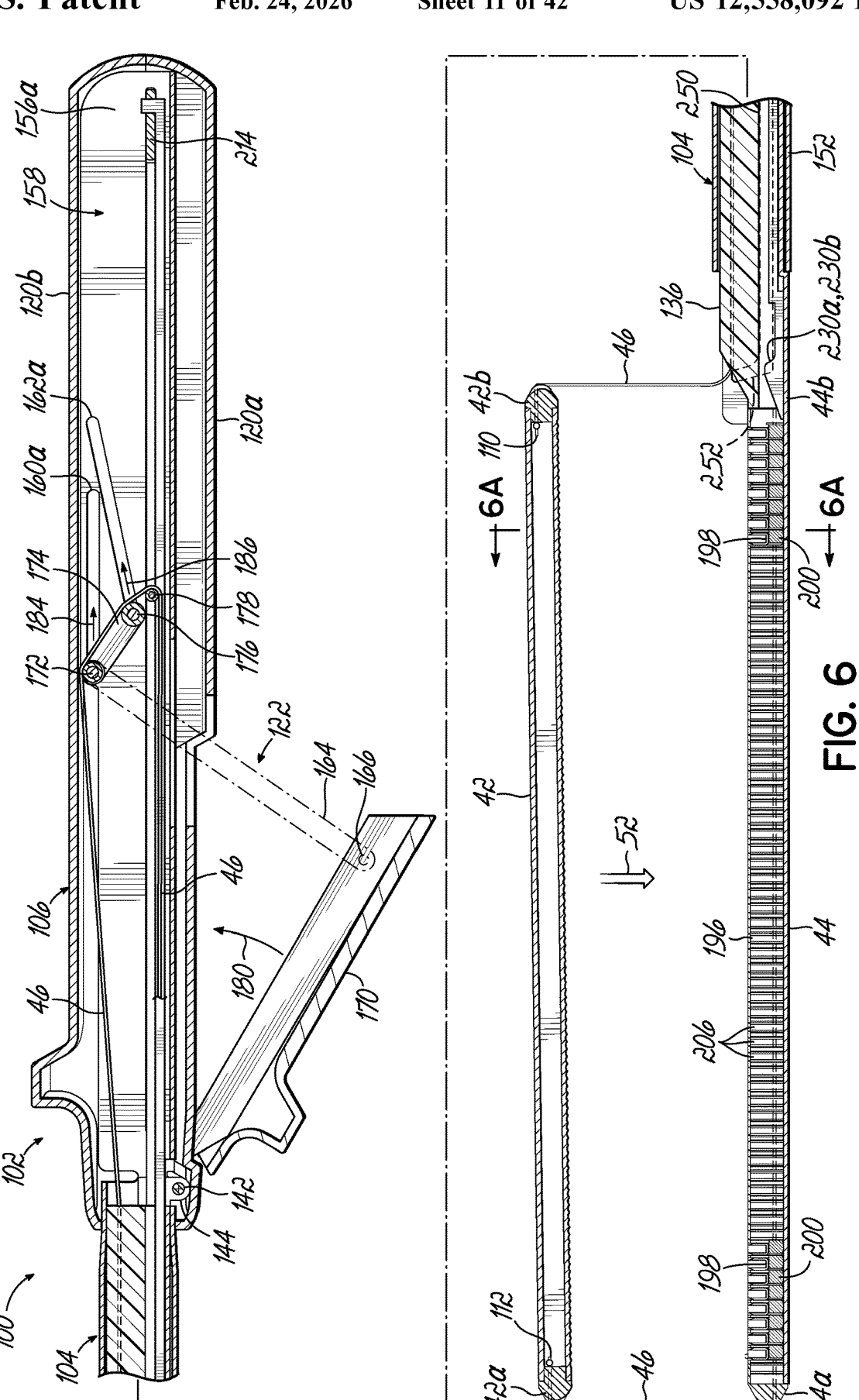
FIG. 6 is a cross-sectional view of the endocutter stapling device taken along section line 6-6 of FIG. 4.

In this regard, in the exemplary embodiment shown in FIGS. 4-6, the flexible member 46 extends from the shaft 104 into the cartridge 44 at a proximal end 44b and ultimately couples the anvil 42 to the cartridge 44. While numerous pathways for the flexible member are possible, in the exemplary embodiment, the flexible member 46 passes from the cartridge 44 and is coupled to the anvil 42 adjacent each of a distal end 42a and a proximal end 42b thereof and may be anchored within the anvil 42 by anchors 110 and 112 (shown in FIG. 6).

Retraction of the flexible member 46 from the end effector 40 (and into the manipulator 102 described below) therefore moves at least one of the anvil 42 and/or the cartridge 44 as is shown generally by the arrow 52 in FIG. 6. It will be appreciated that because the flexible member 46 is anchored to the anvil 42 (e.g., proximate each of the distal end 42a and the proximal end 42b), retraction of the flexible member 46 produces a substantially symmetrical closing force on tissue situated between the anvil 42 and the cartridge 44. This configuration, that is, with connectivity between the anvil 42 and the cartridge 44 at each end of the end effector 40, is advantageous.

In this regard, in embodiments in which the anvil 42 and/or the cartridge 44 are sufficiently rigid at pressures encountered during a surgical procedure, the clamping force may be more symmetrical and uniformly distributed along the length of the anvil 42 and the cartridge 44. Thus, the tissue situated between the anvil 42 and the cartridge 44 may be more uniformly compressed. It will be appreciated that even though there may be more uniform compression on the tissue, the anvil 42 and the cartridge 44 may not be parallel to one another in the clamped position because the tissue may not be uniformly thick. Nevertheless, there may be uniformity in applied pressure. Alternatively, the anvil 42 and the cartridge 44 may be generally parallel yet a gap between the opposing faces of each varies in dimension between a distal end and a proximal end of the end effector 40. The variation in gap may be according to a predetermined relationship to accommodate for the change in thickness of the compressed stomach during clamping. Even though the gap may vary in dimension from one end to the other, the end effector 40 may uniformly apply pressure to the clamped tissue. In each instance, this may be unlike prior art devices in which clamping members are attached together at a single, hinge-like location and have a jaw-like motion, rather than a vice-like motion. With a single connection, the end of the clamp member most distant from the connection may deflect. As a result of the deflection, the clamp member may not apply uniform, symmetrical compression to the tissue along its length. Furthermore, deflection becomes more exaggerated as the clamp members lengthen. Thus, deflection limits the practical upper limit on length for hinge-like devices. It was recognized that producing a substantially uniformly applied clamping pressure may enhance the formation of the staple line following stapling and cutting.

With reference to FIGS. 3, 4, 5, and 6, in one embodiment, the manipulator 102 includes a main body 114 with housing halves 120a, 120b. When assembled, the housing halves 120a, 120b enclose control features by which the surgeon may operate clamping of the anvil 42 and the cartridge 44 on the stomach 10 and then stapling and cutting of the stomach 10. In that regard, the manipulator 102 includes a clamping mechanism 122 for applying tension to the flexible member 46, a stapling mechanism 124 for stapling the tissue captured between the anvil 42 and the cartridge 44, and a cutting mechanism 126 for cutting the tissue. Each of these mechanisms is described below. Thus, in one aspect, the surgeon may operate the clamping mechanism 122 to control the extension and retraction of the flexible member 46 from the end effector 40. In another aspect, the surgeon may actuate the stapling mechanism 124 to fire staples and actuate the cutting mechanism 126 to cut tissue. It will be appreciated that while the endocutter stapling device 100 is described herein as including each of these mechanism, that is, a clamping mechanism, a stapling mechanism, and a cutting mechanism, the invention is not limited to having a cutting mechanism. Specifically, the endocutter stapling device 100 may include a stapling mechanism and not include a cutting mechanism. The surgeon may therefore use the endocutter stapling device 100 to clamp and staple the tissue without cutting it.

To these and other ends, with continued reference to FIG. 5, the manipulator 102 includes a support 130 having a U-shaped cross-section coupled to the end effector 40 at a proximal end. A guide beam 136 of about the same length as the support 130 and reinforces the support 130. The guide beam 136 may include three channels 138a, 138b, and 140 that may receive portions of each of the stapling mechanism 124, the cutting mechanism 126, and the clamping mechanism 122, described below.

In the embodiment shown, the manipulator 102 further includes a frame 150 having a shaft portion 152 and a handpiece portion 154. The shaft portion 152 may have a tubular configuration, for example, a right circular tubular configuration and may enclose the support 130 and the guide beam 136 when the manipulator 102 is assembled. The support 130 may be configured to receive a pin 142 that cooperates with a corresponding bore 144 in the shaft portion 152 to secure the support to the frame 150.

The handpiece portion 154 of the frame 150 is enclosed in the handpiece 106 and includes opposing flanges 156a, 156b defining a channel 158. Each of the flanges 156a, 156b includes one or more slots that guide a portion of the clamping mechanism 122, described below. In the embodiment shown, each flange 156a, 156b includes two pairs of slots 160a, 160b, 162a, 162b. The pair of slots 160a, 162a on the flange 156a is a mirror image of the pair of slots 160b,

162b on the flange 156b. As shown, each of the slots 160a, 160b is elongated in a direction generally parallel with the longitudinal axis of the manipulator 102. The slots 162a, 162b are also elongated but are angled with respect to the longitudinal axis of manipulator 102 and angled relative to the slots 160a, 160b.

The clamping mechanism 122 includes a lever 170 pivotably coupled relative to the housing halves 120a, 120b by the pin 142 in the bore 144. The surgeon operates the lever 170 to tension the flexible member 46. In particular, with reference to FIGS. 6 and 7, the surgeon may squeeze the lever 170 by which motion the flexible member 46 is withdrawn from the end effector 40. As is described above, withdrawing or pulling the flexible member 46 from the end effector 40 draws the anvil 42 toward the cartridge 44 and may tension the flexible member 46 when the anvil 42 and the cartridge 44 meet resistance to movement. By applying a force to the flexible member 46, the anvil 42 and the cartridge 44 may be moved toward one another (as is indicated by arrow 52) and may also apply a clamping force to tissue situated between the anvil 42 and the cartridge 44. It will be appreciated that the surgeon may operate the lever 170 with one or more fingers during operation of the endocutter stapling device 100 between a disengaged position (e.g., FIGS. 3 and 6) in which the clamping mechanism 122 does not restrict movement of the flexible member 46 and an engaged position (e.g., FIGS. 4 and 7) in which the clamping mechanism 122 contacts the flexible member 46.

To that end, the clamping mechanism 122 further includes a push bar 164 pivotably coupled to the lever 170 by a pin 166 at one end thereof. The push bar 164 extends from outside the housing half 120a, where it is pivotally attached to the lever 170 by the pin 166, into the channel 158 of the frame 150 through a slot (unlabeled) in the handpiece portion 154 of the frame 150. The push bar 164 is pivotally coupled to a push bar 174 by a pin 172 in the handpiece 106. The pin 172 extends through the push bar 164 at one end thereof across the channel 158 and is slidably received in each of the slots 160a, 160b (FIG. 5) of the frame 150. The push bar 174 is coupled to a second pin 176 at the opposing end of the bar 174 from the pin 172. The pin 176 is slidably received in each of the slots 162a, 162b (FIG. 5) of the frame 150. The pins 172 and 176 interact with the flexible member 46 when the surgeon squeezes the lever 170. By way of example only, and not limitation, one or both of the pins 172 and 176 may be coupled to a sheave (not shown), which slidably receives the flexible member 46, to guide the flexible member 46 during operation of the clamping mechanism 122.

With continued reference to FIG. 6, the flexible member 46 extends from the shaft 104, between the flanges 156a, 156b, and is looped over the pin 172 and the pin 176 (e.g., in sheaves on each pin 172, 176). In the exemplary embodiment, an additional pin 178 may extend across the channel 158 in fixed relation to the frame 150. The pin 178 may be positioned at a location that maintains the flexible member 46 in alignment with the shaft 104. In other words, the pin 178 may be configured to align the flexible member 46 with the shaft 104 independent of the position of the pins 172, 176 as the pins 172, 176 slide in relation to the slots 160a, 160b, 162a, 162b. Thus, while the flexible member 46 may move in response to actuation of the clamping mechanism 122 along each of the pins 172, 176, the additional pin 178 may maintain alignment of the flexible member 46 with the longitudinal axis of the manipulator 102.

Figure 6A:
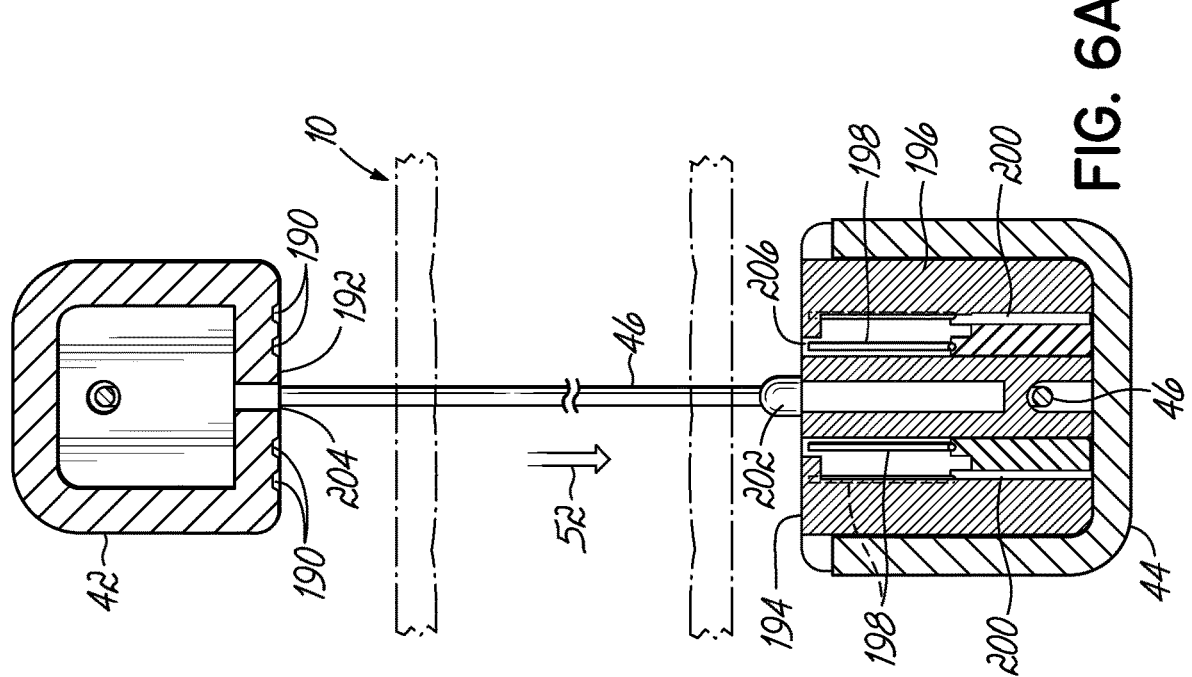
FIG. 6A is a cross-sectional view of the end effector shown in FIG. 4A taken along section line 6A-6A.

With reference to FIGS. 6 and 6A, depression of the clamping lever 170 toward the housing half 102a in the direction of the arrow 180 in FIG. 6 may cause movement of each of the push bars 164, 174 generally away from the end effector 40 in the direction of the longitudinal axis of the handpiece 106. Specifically, as is shown in FIG. 6, the push bars 164, 174 initially have a generally L-shaped arrangement when the lever 170 is extended from the handpiece 106. In this disengaged position of the lever 170, the anvil 42 is spaced apart from the cartridge 44, as is shown in FIGS. 6 and 6A. As the lever 170 is compressed towards the handpiece 106 (according to the arrow 180), the push bar 164 pushes the pin 172 along the slots 160a, 160b (according to the arrow 184). This movement also simultaneously forces the push bar 174 along the longitudinal axis of the manipulator 102 as guided by the pin 172 in the slots 162a, 162b (according to the arrow 186). The pins 172, 176 carry the flexible member 46 in the same direction away from the end effector 40. Overall, the flexible member 46 is withdrawn from the end effector 40 resulting in movement of the anvil 42 toward the cartridge 44. In accordance with embodiments of the invention, a gap between the anvil 42 and the cartridge 44 may vary when the surgeon clamps the stomach 10. In this regard, the clamping mechanism may be configured to create a gap at the distal end 42a, 44a of the end effector 40 that is less than the gap at the proximal end 42b, 44b of the end effector when the clamping mechanism is engaged. In one embodiment of the invention, the clamping mechanism may be configured to withdraw the flexible member 46 from the end effector 40 such that the length of flexible member between the distal ends 42a, 42b of the anvil 42 and the cartridge 44 is less than the length of flexible member 46 between the proximal ends 42b, 44b of the anvil 42 and the cartridge 44. As is described below, the anvil 42 may therefore be intentionally tilted relative to the cartridge 44 such that the gap is not uniformly formed between the anvil 42 and the cartridge 44. This gap configuration may then be imposed on the stomach 10 though it may produce more uniform pressure distribution on the stomach 10. Those of ordinary skill in the art will recognize that there may be other configurations resulting in a varying gap between the anvil and the cartridge that are useful in embodiments of the present invention.

Figure 7A:
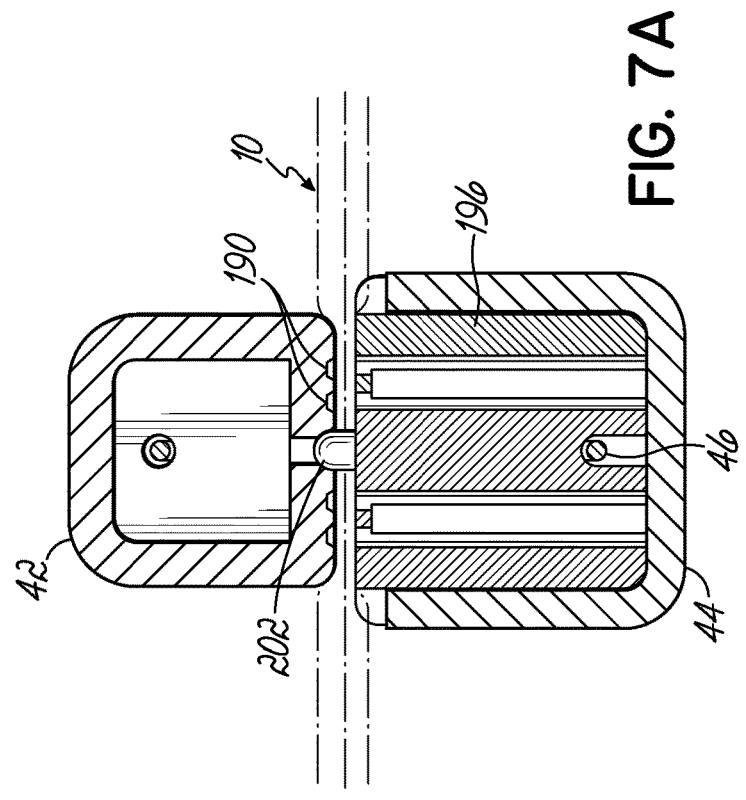
FIG. 7A is a cross-sectional view of the endocutter stapling device taken along section line 7A-7A in FIG. 7.
Figure 7:
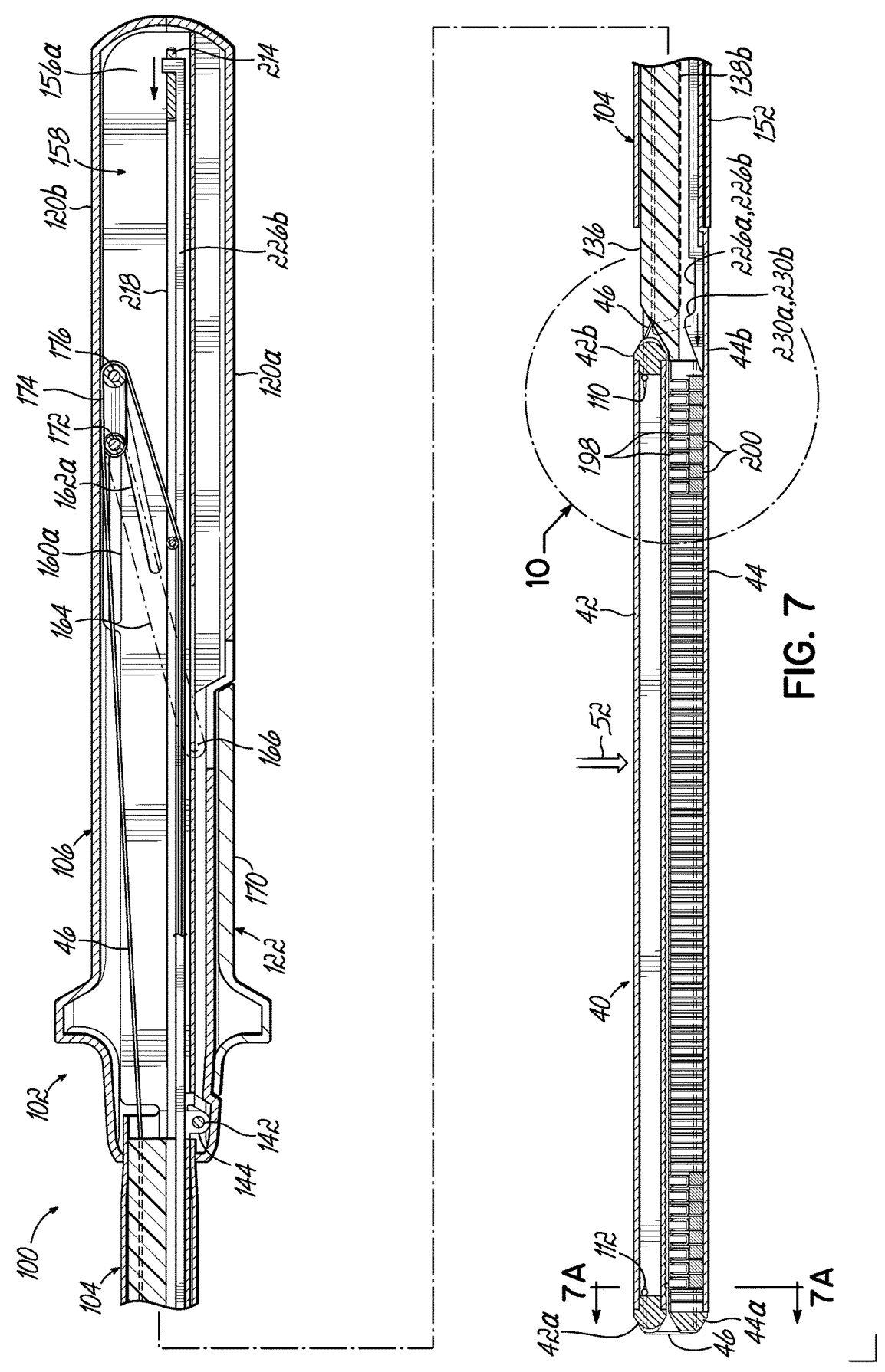
FIG. 7 is a cross-sectional view of the endocutter stapling device taken along section line 7-7 of FIG. 3.

Compression of the lever 170 into the engaged position results in the configuration of the endocutter stapling device 100 shown in FIGS. 7 and 7A, in which the push bars 164, 174 are generally aligned with respect to one another and the anvil 42 and cartridge 44 are compressed onto the stomach 10. In the generally aligned configuration between the push bars 164, 174, the path around which the flexible member 46 extends is lengthened relative to the L-shaped arrangement shown in FIG. 6. By lengthening the path, the flexible member 46 is carried rearwardly within the handpiece 106 during actuation of lever 170. This results in a corresponding withdrawal of the flexible member 46 from the end effector 40. Accordingly, the compression of the lever 170 toward the housing half 120a pulls the anvil 42 towards the cartridge 44 as is indicated by arrow 52 in FIG. 7. This motion may result in compression of the stomach 10 between the anvil 42 and the cartridge 44, as is shown in FIG. 7A. By way of example and not limitation, the clamping mechanism 122 may be capable of tensioning the flexible member 46 to about 200 lbs. at each end of the anvil 42. This may provide a clamping pressure of over 100 psi. Specifically, in an exemplary embodiment, the anvil 42 and the cartridge 44 may have a length of about 250 mm and a width of about 10 mm providing a surface area of about 25 cm2. With 400 lbs. of total tension on the flexible member 46 (i.e., 200 lbs. on each side), the total compression pressure may be about 103 psi.

With reference now to FIG. 6A, in one embodiment, the anvil 42 includes a plurality of staple pockets 190 along a face 192 of the anvil 42. The cartridge 44 includes a face 194 that opposes the face 192 of the anvil 42. Each of the faces 192, 194 is configured to compress the stomach 10 there between. The staple pockets 190 in the face 192 generally align and correspond to a plurality of staples 198 and a plurality of staple drivers 200 that are housed in a plurality of staple channels 206 defined by the cartridge 44. The cartridge 44 includes a cartridge body 196 that may support the staples 198 and the staple drivers 200. The staples 198 are configured to be forced through the stomach 10 and be deformed by the staple pockets 190. It will be appreciated that deforming the staples 198 into a B-shaped configuration secures opposing sides of the stomach 10 together.

In one embodiment, to facilitate alignment between the anvil 42 and the cartridge 44, and in particular, alignment between the staples 198 and the staple pockets 190, an alignment pin 202 may extend beyond the face 192 at the distal end 42a of the anvil 42 or the face 194 at the distal end 44a of the cartridge 44. The other face 192, 194 of the anvil 42 or the cartridge 44 includes a mating recess 204. Once the lever 170 is compressed, the flexible member 46 is pulled into the handpiece 106 by the clamping mechanism 122 as described above. This motion pulls the anvil 42 toward the cartridge 44 and the alignment pin 202 in conjunction with the mating recess 204 to facilitate proper alignment between the anvil 42 and the cartridge 44 to align the staples 198 with a corresponding pocket 190. With reference to FIG. 7A, the anvil 42 and the cartridge 44 are shown to compress the stomach 10 between the face 192 of the anvil 42 and the face 194 of the cartridge 44 with the alignment pin 202 being received in the mating recess 204. In another aspect of the present invention, once the lever 170 is compressed, as is shown in FIG. 7, with the anvil 42 and the cartridge 44 compressing the stomach 10 there between, the surgeon may staple and cut the stomach 10 along the staple line 12 (FIG. 1). To staple the stomach 10, the surgeon activates the stapling mechanism 124.

Figures 8, 9:
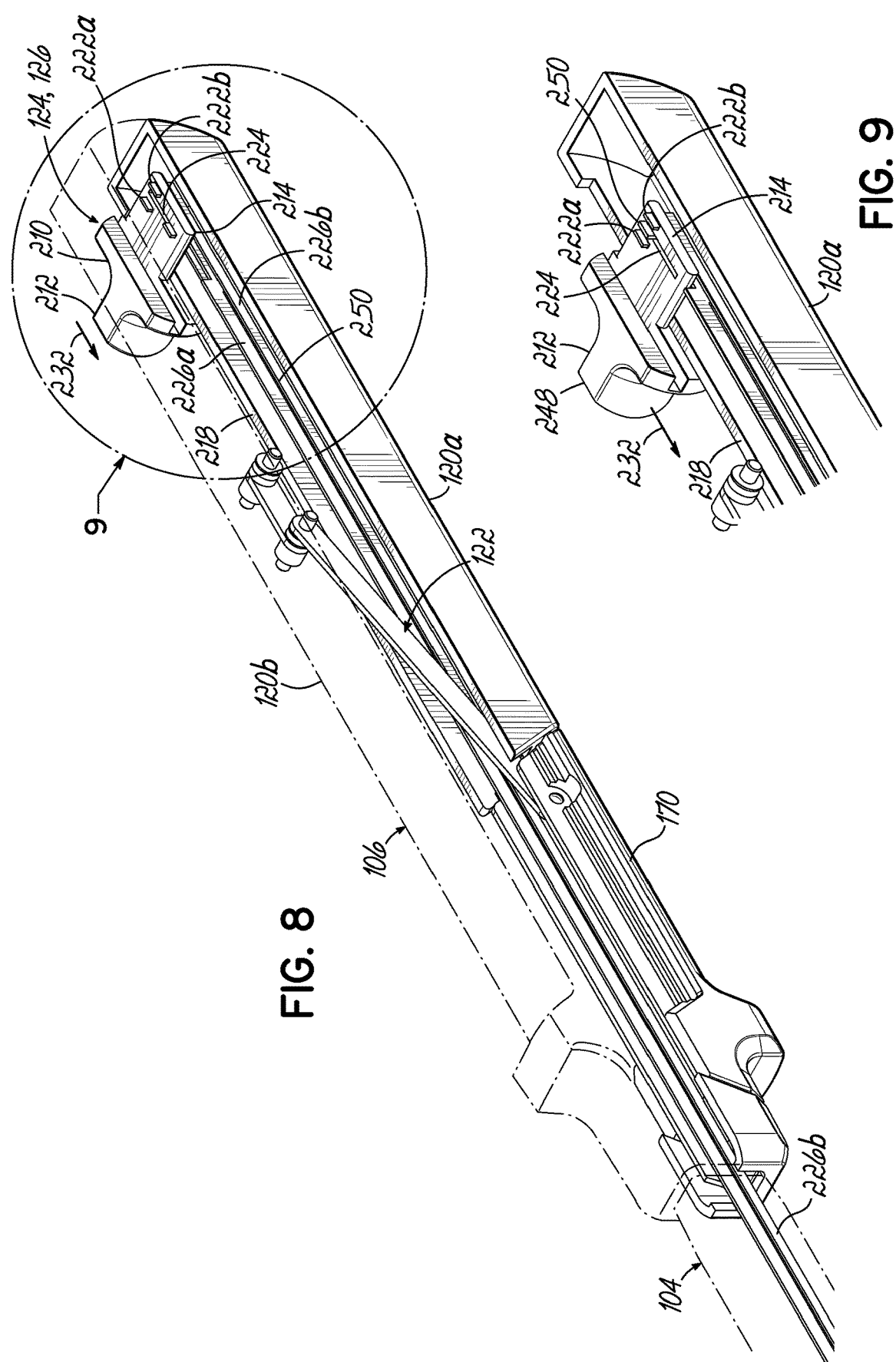
FIG. 8 is an enlarged perspective view of a handpiece of the endocutter stapling device of FIG. 3.
FIG. 9 is an enlarged view of the encircled area 9 shown in FIG. 8.
Figures 10, 10B:
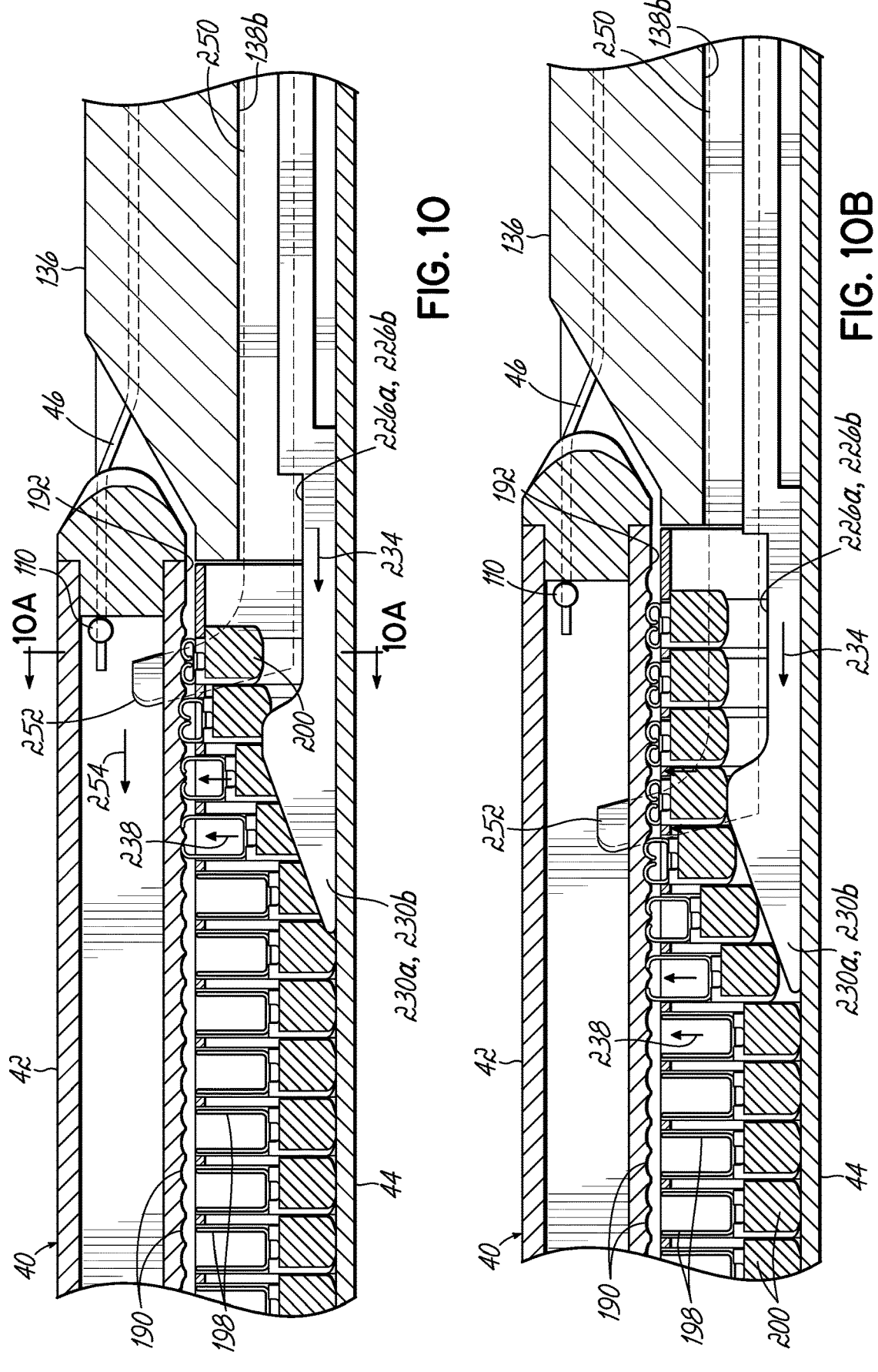
FIG. 10 is an enlarged view of the encircled area of the endocutter stapling device of FIG. 7.
FIG. 10B is an enlarged view of the endocutter stapling device similar to FIG. 10 during use of the endocutter stapling device.

In that regard and with reference to FIGS. 3, 8, and 9, the stapling mechanism 124 includes a staple actuator 210 having a thumb tab 212. The staple actuator 210 further includes an actuator plate 214 that is coupled to the thumb tab 212. The actuator plate 214 is slidably received in a slot 218 (FIG. 3) formed between the housing halves 120a, 120b and is movable relative to the handpiece 106 as is indicated by the arrow 232 in FIGS. 8 and 9. The actuator plate 214 includes slots 222a, 222b spaced apart from an elongated slot 224. In the embodiment shown, the slots 222a, 222b each receive a wedge push bar 226a, 226b, respectively. As is shown in FIGS. 5 and 10, the wedge push bars 226a, 226b are elongated members that extend generally along the length of the handpiece 106 and through the shaft 104 and terminate proximate the end effector 40. The wedge push bars 226a, 226b are slidably received in corresponding channels 138a, 138b of the guide beam 136 and are positioned to slide into engagement with the staples 198 and the staple drivers 200 in the cartridge 44.

In one embodiment, shown in FIG. 10, each wedge push bar 226a, 226b terminates in a wedge tip 230a, 230b which, prior to activation of the stapling mechanism 124, is positioned to engage respective rows of the staple drivers 200 in the cartridge 44. The wedge tips 230a, 230b have a wedge-shaped configuration and, during a sliding motion through the end effector 40, are configured to force the staple drivers 200 toward the anvil 42 and drive the corresponding staples 198 through the compressed stomach 10 and into contact with the corresponding staple pockets 190 of the anvil 42. As shown best in FIGS. 10 and 10B, the shape of the wedge tips 230a, 230b forces the staples 198 into contact with the staple pockets 190 of the anvil 42 with sufficient force to deform the staples 198 and produce a B-shaped staple.

In one embodiment, the surgeon activates the stapling mechanism 124 by pushing the thumb tab 212 in the direction of the end effector 40 as is indicated by the arrow 232 in FIGS. 8 and 9. Pushing the thumb tab 212 slides each of the wedge push bars 226a, 226b and the corresponding wedge tips 230a, 230b in the direction of the end effector 40. Specifically, and with reference now to FIGS. 10C-10D, pushing the thumb tab 212 (FIG. 8) moves the wedge push bars 226a, 226b in the direction of the arrow 234. The wedge tip 230a engages the staple drivers 200 in sequence and thereby forces the staples 198 into the corresponding staple pockets 190 on the anvil face 192 as is indicated by the arrows 238.

In another aspect of the present invention, the surgeon may cut the stomach 10 along the staple line 12 following stapling, described above. In one embodiment and with reference to FIG. 5, to cut the stomach 10, the surgeon activates the cutting mechanism 126. The cutting mechanism 126 includes a knife actuator 248 including the thumb tab 212 coupled to the actuator plate 214. As described above and with reference to FIGS. 8 and 9, the actuator plate 214 is slidably received in the slot 218 formed between the housing halves 120a, 120b and is movable relative to the handpiece 106 in a direction that is indicated by the arrow 232 in FIGS. 8 and 9.

Figure 10A:
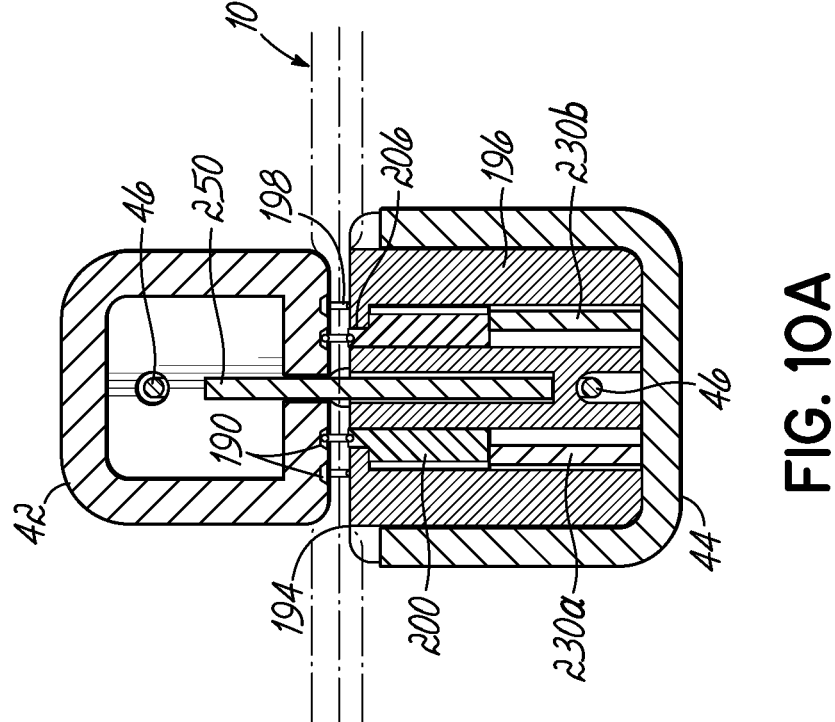
FIG. 10A is a cross-sectional view of the endocutter stapling device taken along section line 10A-10A in FIG. 10.
Figure 10C:
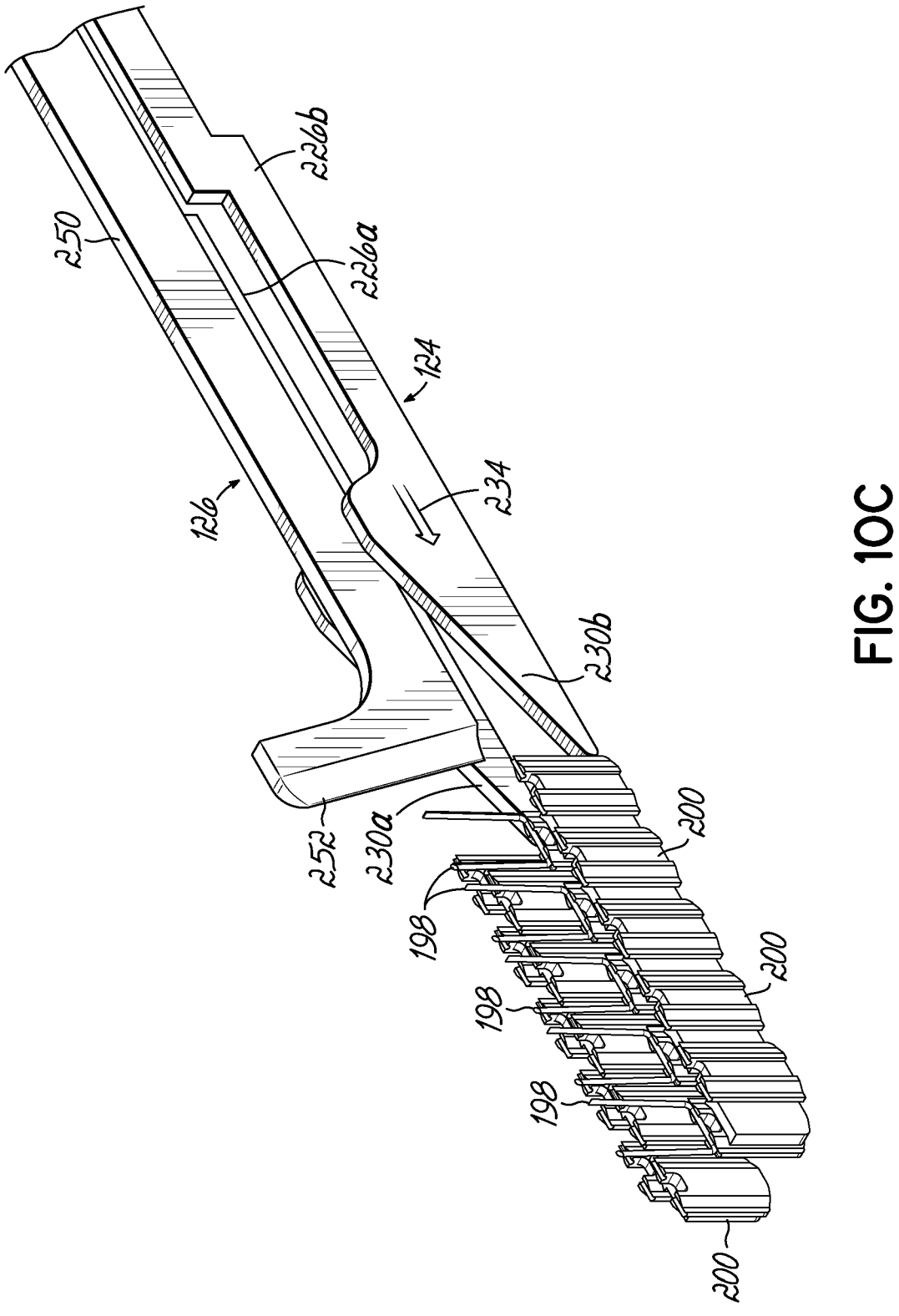
FIG. 10C is a perspective view of a knife and a pair of wedges of the endocutter stapling device of FIG. 3.
Figure 10D:
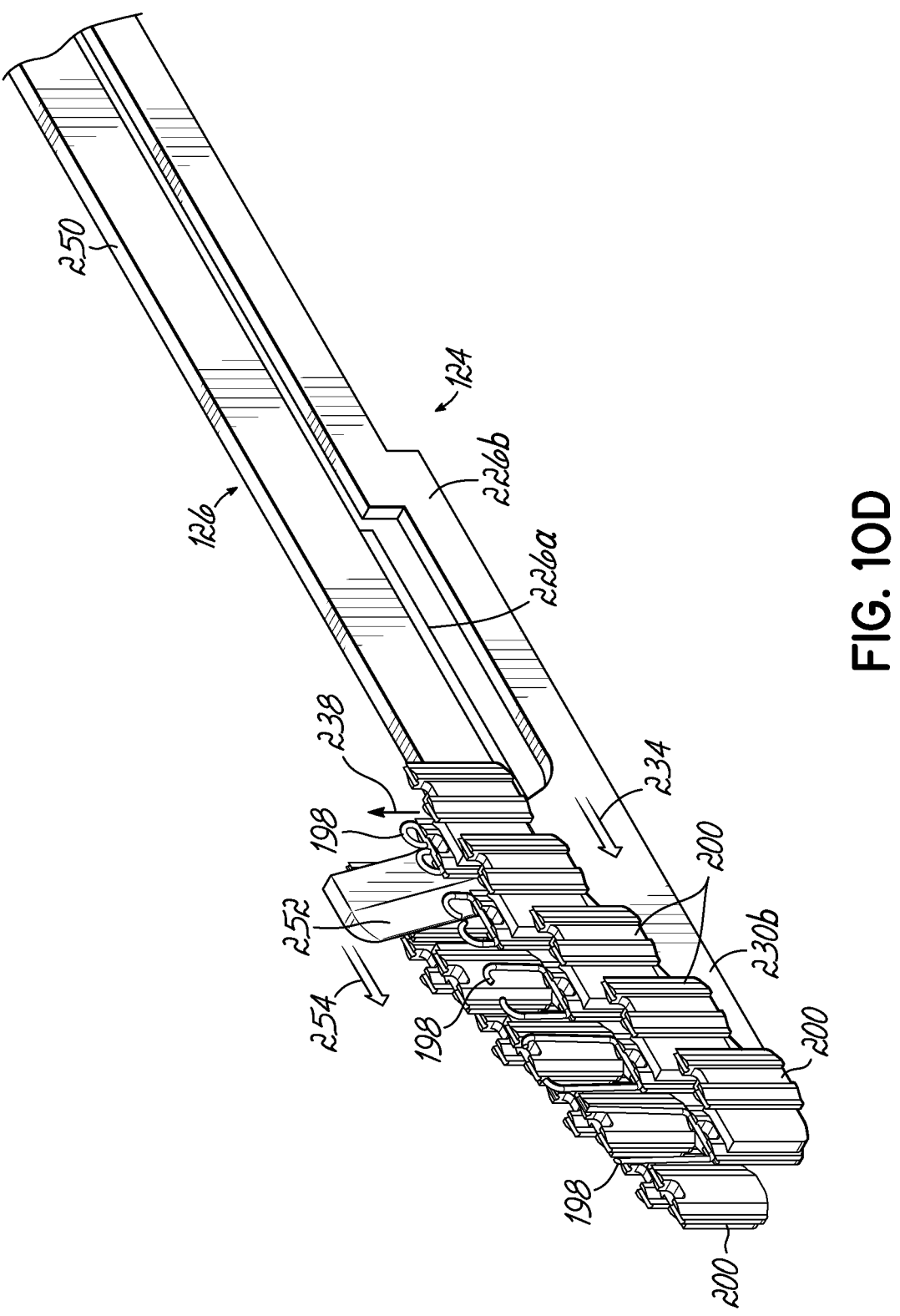
FIG. 10D is a perspective view of the knife and the pair of wedges shown in FIG. 10 during use of the endocutter stapling device.

With reference to FIGS. 10-10A, in one embodiment, the cutting mechanism 126 includes the elongated slot 224 in the actuator plate 214. A knife push bar 250 is slidably engaged in the elongated slot 224 and may be an elongated member extending from the actuator plate 214 through the handpiece 106 and the shaft 104 to a location adjacent the end effector 40. In that regard, the knife push bar 250 is slidably received in the channel 140 of the guide beam 136 and terminates in a cutting edge 252 proximate the end effector 40 (shown best in FIGS. 10-10D). As can be appreciated specifically by FIGS. 5, 10C and 10D, the knife push bar 250 lies in between the wedge push bars 226a, 226b. In one embodiment, the surgeon activates the cutting mechanism 126 by pushing the thumb tab 212 in the direction of the end effector 40 as is indicated by the arrow 232 in FIG. 8. Pushing the thumb tab 212 slides the knife push bar 250 via the actuator plate 214 and pushes the corresponding cutting edge 252 in the direction of the end effector 40.

Specifically, and with reference now to FIGS. 10, 10A, and 10B, pushing the thumb tab 212 moves the cutting edge 252 in the direction of the arrow 254 along the longitudinal axis of the endocutter stapling device 100. Although not shown, the cutting edge 252 cuts the stomach that may be clamped between the anvil 42 and the cartridge 44.

In one embodiment, and with reference to FIGS. 8 and 9, the thumb tab 212 may activate each of the stapling mechanism 124 and the cutting mechanism 126. As is described above, the actuator plate 214 captures each of the wedge push bars 226a, 226b and the knife push bar 250 in slots 222a, 222b and elongated slot 224, respectively. In one embodiment, even though the actuator plate 214 is operably coupled to each of the wedge push bars 226a, 226b and the knife push bar 250, engagement of the stapling mechanism 124 occurs prior to actuation of the cutting mechanism 126. In other words, the stapling mechanism 124 engages prior to engagement of the cutting mechanism 126. The elongated slot 224 in the actuator plate 214 is oversized relative to the portion of the knife push bar 250 that is engaged with it. This configuration results in sliding space between the elongated slot 224 and the knife push bar 250. The knife push bar 250 therefore slides relative to the actuator plate 214 during initial movement of the actuator plate 214. The length of the movement of the actuator plate 214 without movement of the knife push bar 250 is predetermined.

The elongated slot 224 is also longer than each of the slots 222a, 222b. Because the knife push bar 250 is slidably received in the elongated slot 224, the initial movement of the actuator plate 214 in the direction of arrow 232 in FIG. 8 causes each of the wedge push bars 226a, 226b to move in direct relation to the movement of the actuator plate 214. The movement of the knife push bar 250 is however delayed relative to the movement of the wedge push bars 226a, 226b. This means that there is a delay between activation of the stapling mechanism 124 and the cutting mechanism 126. This delay is proportional to the free sliding space between the elongated slot 224 and the knife push bar 250.

When the surgeon pushes the thumb tab 212 in the direction of the arrow 232 in FIG. 8, the actuator plate 214 moves in the same direction and carries the wedge push bars 226a and 226b with it. The knife push bar 250 does not initially move. Instead, the actuator plate 214 must move a predetermined distance corresponding to the free sliding space in the direction of the end effector 40 before the actuator plate 214 engages the knife push bar 250. This is shown by way of comparison between FIGS. 8 and 9. In FIG. 8, the actuator plate 214 has not engaged the knife push bar 250. In FIG. 9, the actuator plate 214 has moved a distance at least equivalent to the free sliding space and so the actuator plate 214 engages the knife push bar 250. This delay in movement between the wedge push bars 226a, 226b and the knife push bar 250 results in a difference in activation time between the stapling mechanism 124 and the cutting mechanism 126. In this manner, in one embodiment, activation of the stapling mechanism 124 precedes activation of the cutting mechanism 126.

Once the surgeon activates each of the stapling mechanism 124 and the cutting mechanism 126 by pushing on the thumb tab 212, stapling and cutting may occur substantially simultaneously. By way of example only, the stapling of the stomach 10 may precede the cutting of the stomach 10. That is, after an initial delay between stapling and cutting, during which the stapling mechanism 124 is activated, both of the stapling mechanism 124 and the cutting mechanism 126 are active. The surgeon may continue stapling and cutting the stomach 10 by continuing to push on the thumb tab 212 until the thumb tab 212 reaches the end of its stroke. It will be appreciated that the stroke of the thumb tab 212 may be greater than the overall length of the stomach 10. Further, the stroke of the thumb tab 212 may be approximately equal to the length of the end effector 40. At this point, the wedge tip 230a, 230b may be proximate the distal end 42a, 44a of the end effector 40. The end effector 40 and the shaft 104 may then be removed from the abdominal cavity with the stomach 10 having the configuration shown in, for example, FIG. 2E. Tensioning, stapling, and cutting mechanisms are further described in the commonly-owned U.S. Application No. II, which is filed concurrently with the present application and is being incorporated by reference herein in its entirety.

With reference again to FIG. 1, as described above, the stomach 10 may vary in thickness from the antrum 24 to the fundus 26. Stomach specimens removed from patients have been analyzed for tissue thickness at three points along a resection line—the antrum 24, the fundus 26, and a mid-way point between the antrum 24 and the fundus 26 called the body. These values were used to estimate closed staple leg heights at these three locations. A closed staple leg height may be estimated based on a known tissue thickness along the staple line. Closed staple leg height refers to the height dimension of a deformed staple. Open staple leg height may be calculated from a closed staple leg height. Open staple leg height refers to the height dimension of a new staple. Thus, prior to stapling, each staple has an open staple leg height. During stapling, the staple may be forcibly deformed. Ideally, each leg of a staple is deformed to produce a B-shaped staple in which a tooth, sometimes referred to as a point, of each leg points in the direction of the crown. Following stapling, each deformed staple has a closed staple leg height. The average closed staple leg heights were estimated to be about 1.8 mm, about 2.4 mm, and about 3.0 mm for the fundus, the body, and the antrum, respectively. The average open staple leg heights were calculated to be about 3.8 mm, about 4.4 mm, and about 5.0 mm for the fundus, the body, and the antrum, respectively. Not being bound by theory, it is believed that the tissue thickness provides information regarding the closed staple leg height at a particular location. When all of the specimens and the estimated closed staple leg heights are considered, according to an embodiment of the invention, a relationship between the closed staple leg height and the variation in thickness of the human stomach along a targeted resection line was determined.

In this regard, an increase in average thickness from the fundus 26 to the antrum 24 was calculated. The increase was determined to be approximately linear with a degree of the increase in the average thickness of the stomach along the resection lines of these stomach specimens of about 0.382 degrees. As shown in FIG. 2B, the end effector 40 extends across the length of the stomach 10. When compressed, a gap between the anvil 42 and the cartridge 44 varies in a predetermined relationship relative to this change in tissue thickness. Accordingly, aspects of the present invention may utilize predetermined changes in gap dimensions at defined locations between the anvil 42 and the cartridge 44 along a longitudinal axis of the end effector 40.

Figure 11:
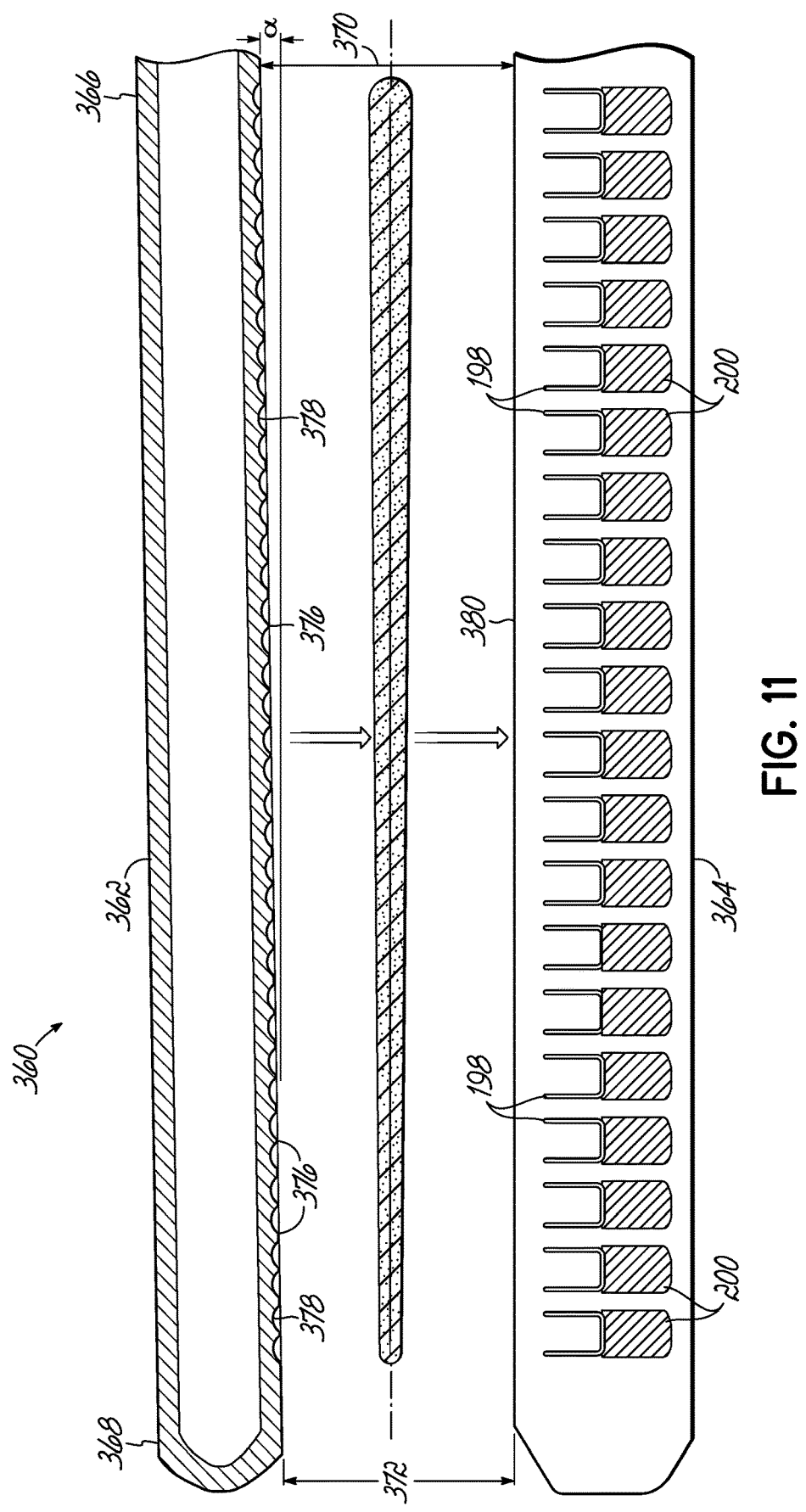
FIG. 11 is a schematic elevation view of an end effector according to one embodiment of the present invention.

To that end, in one embodiment and with reference to FIG. 11, an end effector 360 includes a gap 370 between the anvil 362 and the cartridge 364 at a proximal end 366 of the end effector 360 ("proximal gap 370") and a gap 372 at a distal end 368 of the end effector 360 ("distal gap 372"). The proximal gap 370 is different from the distal gap 372. Specifically, the anvil 362 has a face 376 that includes a plurality of staple pockets 378, and the cartridge 364 has a face 380 that opposes the face 376 of the anvil 362. The proximal gap 370 and the distal gap 372 are measured between the faces 376 and 380. The orientation between the face 376 and the face 380 may therefore determine the gaps 370 and 372. In one embodiment, the proximal gap 370 is larger than the distal gap 372 when the stomach 10 is compressed between the anvil 362 and the cartridge 364. The difference between the gap 370 and the gap 372 may be determined based on the anatomy of the stomach 10 described above. By way of example, and not limitation, the distal gap 372 may range from, for example, about 1.5 mm to about 3.3 mm, and the proximal gap 370 may be in the range of about 2.0 mm to about 5.0 mm. Further, and without limitation, the angle of increase in the gap from the distal gap 372 to the proximal gap 370 may be from about 0.1° to about 1°.

Furthermore, the orientation between the anvil 362 and the cartridge 364 may determine all of the distances between the two faces 376, 380 from the proximal end 366 to the distal end 368. For example, with continued reference to FIG. 11, the face 376 of the anvil 362 may not be parallel with the face 380 of the cartridge 364. As shown, the face 376 may be uniformly sloped at an angle a relative to the face 380 of the cartridge 364. The distances between the face 376 and the face 380 may linearly decrease from the proximal gap 370 to the distal gap 372 according to the angle a. The angle a may be proportional to a corresponding change in the average closed staple leg heights according to a corresponding location along the staple line 12 on the stomach 10. That is, in one embodiment, the angle a may be directly related to a measured angle across the average closed staple leg heights by location on the stomach. By way of example only, and not limitation, the distal gap 372 may be about 1.7 mm, the proximal gap 374 may be about 3.3 mm, and the angle a may be about 0.367 degrees.

As is shown in FIG. 11 and is described in more detail below, the cartridge 364 houses staples 198 and staple drivers 200. Further, the cartridge 364 may be divided into zones in which the staples 198 differ in open leg length. The open leg length of the staples 198 may vary in accordance with the thickness of the stomach 10 when compressed. It should be recognized that these values are merely exemplary and the particular values for the distal and proximal gaps may depend on several factors, including the anatomical structure being clamped as well as other factors. Thus, the invention is not limited to the range of values provided herein. Various aspects of the present invention address the varying gap between the anvil and the cartridge to improve the quality and consistency of the staple line.

It will be recognized that the varying gap between the anvil and the cartridge along the length of the end effector may affect a delta gap of the formed staples. The delta gap is the difference in the gap between the leading leg and the staple crown and the gap between the lagging leg and the staple crown. In this regard, an end effector with a gap having an angle of about 0.382 degrees and including staples with a crown length of 2.65 mm, may produce a delta gap of about 0.0177 mm. This does not exceed known exemplary delta gaps in staples formed using open linear staplers such as 0.21 mm and 0.29 mm.

Figures 12A, 12B, 12C:
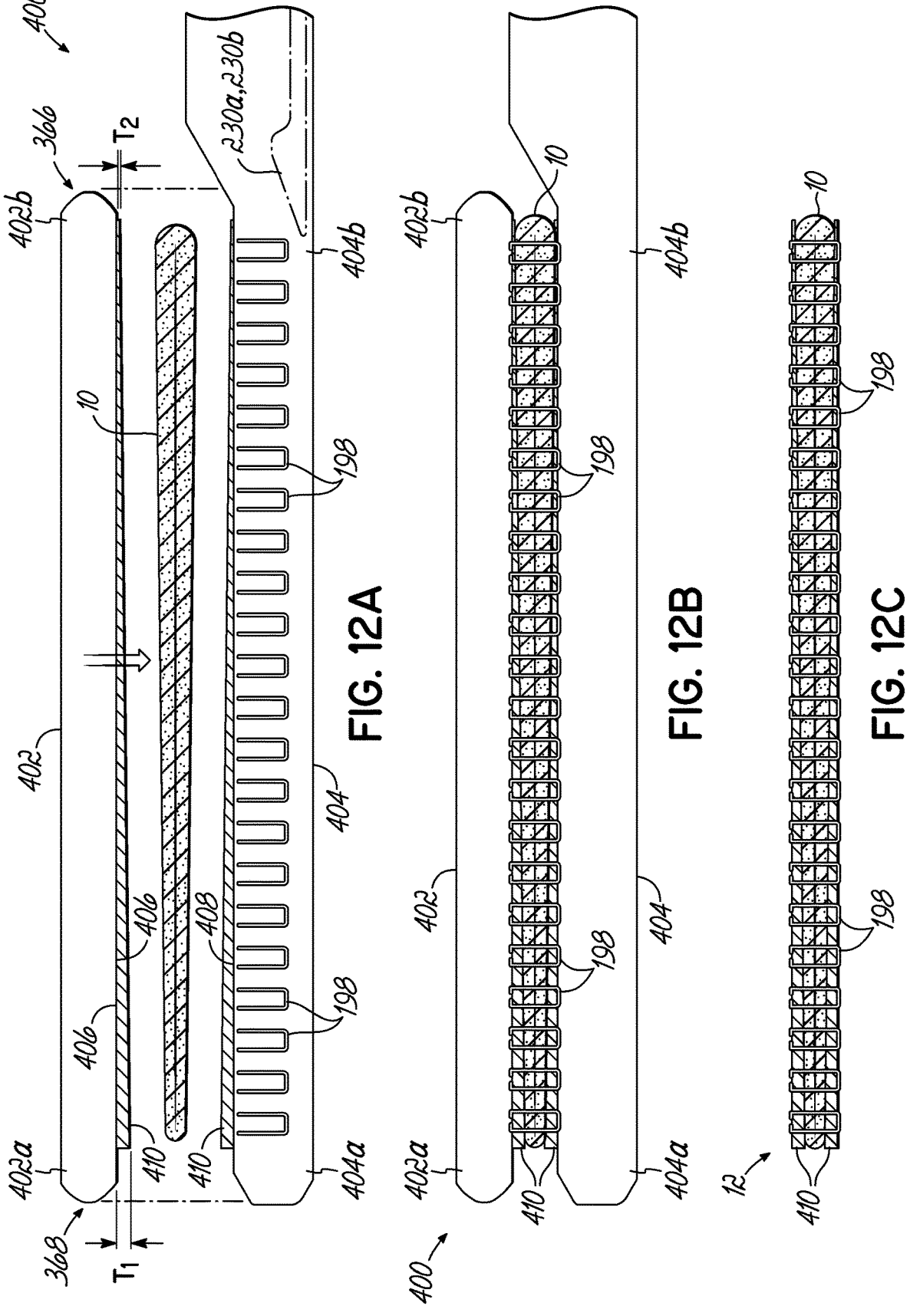
FIG. 12A is a schematic elevation view of an end effector according to one embodiment of the present invention.
FIG. 12B is a schematic elevation view of the end effector of FIG. 12A positioned on a stomach after actuation of an endocutter stapling device according to one embodiment of the invention to complete a staple line.
FIG. 12C is a schematic elevation view of stomach anatomy resulting from the use of an endocutter stapling device according to one embodiment of the invention.
Figures 13, 14A, 14B:
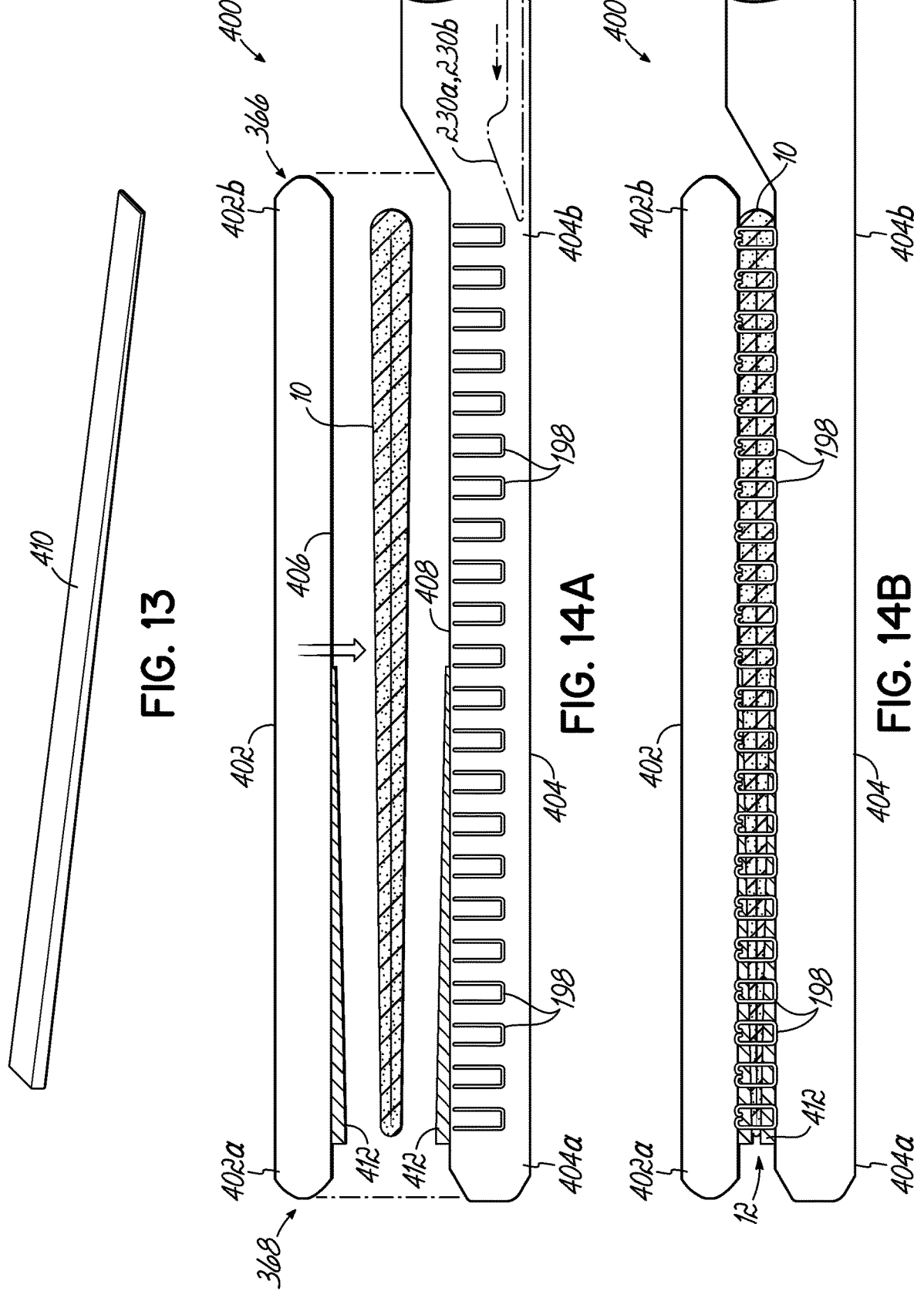
FIG. 13 is a perspective view of a shim according to one embodiment of the present invention.
FIG. 14A is a schematic elevation view of an end effector according to one embodiment of the present invention.
FIG. 14B is a schematic elevation view of the end effector of FIG. 14A positioned on a stomach after actuation of an endocutter stapling device according to one embodiment of the invention to complete a staple line.

In an alternative configuration in which like reference numerals refer to like features throughout the figures, and with reference to FIGS. 12A-12C, in one embodiment, an end effector 400 includes an anvil 402 and a cartridge 404. The anvil 402 has a face 406, and the cartridge 404 has a face 408. As shown, a shim 410 is coupled to each of the anvil 402 and the cartridge 404. Each shim 410 increases in thickness from the proximal end 366 to the distal end 368 of the anvil 402. An exemplary shim is shown in FIG. 13. A shim 410 maybe formed from material that is bio-absorbable. The material may also be flexible, and, if it is a polymer, the material may be such that it will not cross link further to become a rigid structure. By way of example, and not limitation, the shim material may include dilactones, bioresorbable elastomer made from poly (glycerol sebacate), polylactide (PLA), polyglycolide (PGA), a copolymer of E-caprolactone and glycolide, or a non-absorbable polymer such as polytetrafluoroethylene (PTFE). The shim material may also include biologic materials such as bovine pericardium, small intestinal submucosa laminate, or acellular dermal matrix.

The change in thickness of each shim 410 may be determined based on the change in thickness of the stomach 10, described above. By way of example, the thickness of each shim 410 at predetermined locations along the length of the shim 410 may be determined at least in part using the estimated thickness of the stomach 10 and the gap between the face 406 of the anvil 402 and the face 408 of the cartridge 404 at a given location along the length of the stomach 10 when the faces 406 and 408 are substantially parallel. By way of example, the thickness of each shim 410 may be about one half of the difference in height between the gap and the thickness of the stomach 10 (when compressed) at each location between the faces 406 and 408. With this configuration, the shims 410 compensate for the expected variation in the compressed stomach thickness. When the stomach 10 is compressed between the anvil 402 and the cartridge 404, the change in thickness of the shims 410 and the corresponding change in thickness of the stomach 10 provide a generally overall consistent total gap between the faces 406 and 408 over the length of the end effector 400.

With reference to FIGS. 12B and 12C, during actuation of the end effector 400, as the wedges 230a, 230b push the staple drivers (not shown) toward the anvil 402, the staples 198 pierce through each of the shims 410 at the faces 406, 408 and come into contact with the staple pockets (not shown). As is shown, once the staple line is complete, the staples 198 having the same open leg length (as is shown in FIG. 12A) will also have generally the same closed leg length along the length of the staple line. Advantageously, using the shims 410 may reduce the likelihood of improper staple formation due to the variable thickness of the stomach 10 since the gap between the faces 406 and 408 is substantially uniform from the proximal end 366 to the distal end 368. Additionally, the presence of the shims 410 may act as reinforcement to the staple line 12, as can be appreciated from FIG. 12C in which the shims 410 form part of the staple line 12. Further, because each of the staples 198 has the same open leg length along the entire staple line 12, the surgeon is not required to estimate the stomach thickness to determine what staple open leg length should be placed in the cartridge 404. Aspects of the present invention are not limited to the illustrated arrangement, where both the anvil 402 and the cartridge 404 include a shim 410. In one embodiment, for example, the cartridge 404 may be coupled to a shim, while the anvil 402 is not coupled to a shim. Other alternative arrangements may also be possible.

In one embodiment and with reference to FIG. 14A, a shim 412 may extend along a part of the length of the anvil 402 and/or along a part of the length of the cartridge 404. In FIG. 14A, one shim 412 extends from about the midway point of the anvil 402 to the distal end 402a of the anvil 402 and another shim 412 extends from about the midway point of the cartridge 404 to the distal end 404a the cartridge 404. In this regard, the shims 412 are located adjacent the thinner portion of the stomach 10 and are generally thinner and shorter than the corresponding shims 410 shown in FIG. 12A-12C.

During actuation, some of the staples 198 pass only through the stomach 10 from the cartridge 404 to the anvil 402, while other staples 198 will pass through the shims 412 and the stomach 10 before reaching the staple pockets (not shown). Once the staple line 12 is complete, the staples 198 having the same open leg length will also have generally the same closed leg length along the length of the stomach 10, as is shown in FIG. 14B. In other words, the varying thickness of the shims 412 and the varying thickness of the stomach 10 combine to provide a generally equal thickness along the length of the staple line. Those of ordinary skill in the art will recognize that aspects of the present invention are not limited to the illustrated arrangement, in which the shims 412 extends over generally half of the length of the anvil 402 and cartridge 404.

26

Figures 15A, 15B:
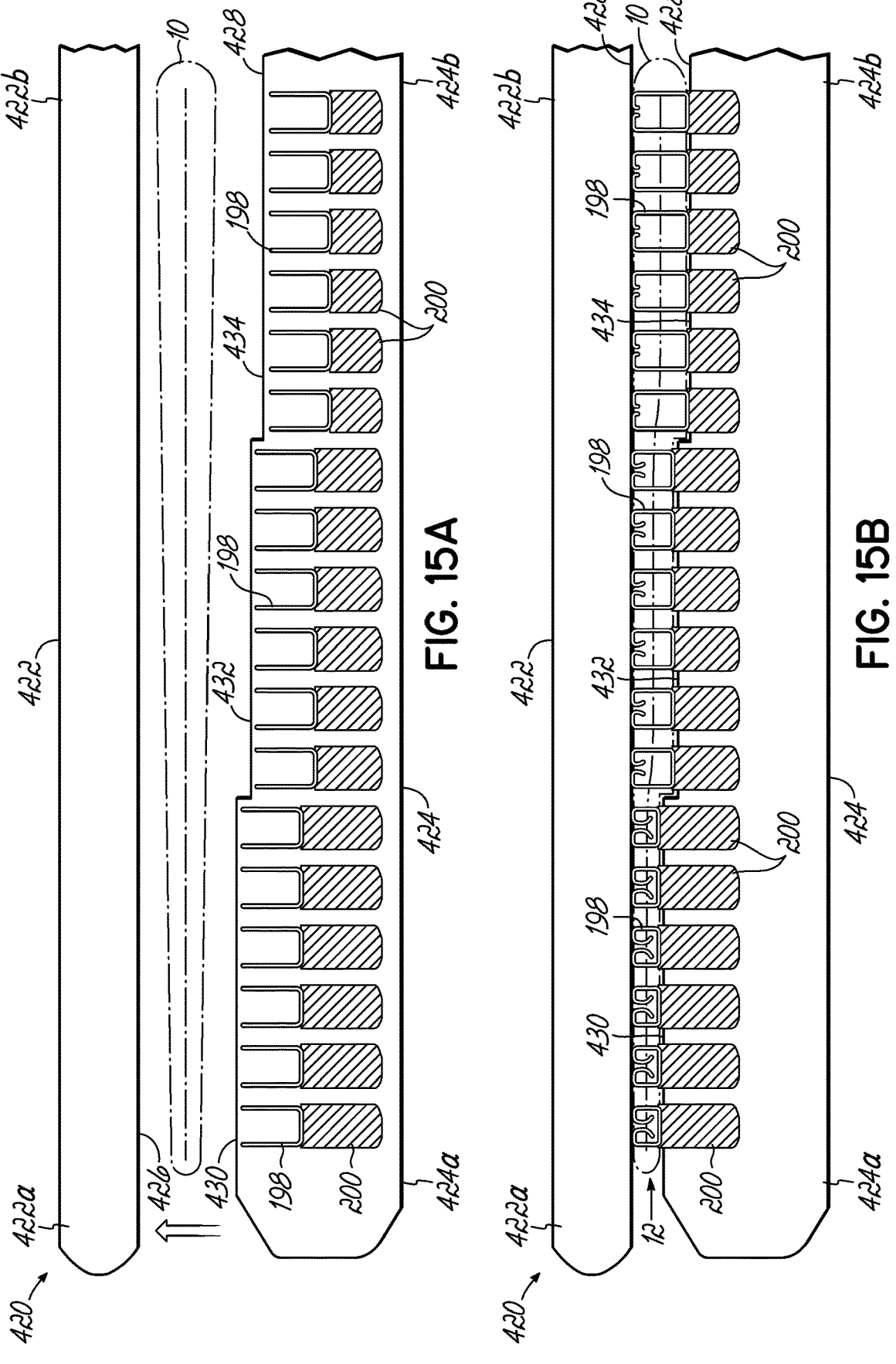
FIG. 15A is a schematic elevation view of an end effector according to one embodiment of the present invention.
FIG. 15B is a schematic elevation view of the end effector of FIG. 15A positioned on a stomach after actuation of an endocutter stapling device according to one embodiment of the invention to complete a staple line.

With reference to FIG. 15A, in one embodiment, an end effector 420 includes an anvil 422 and a cartridge 424 where a gap between the anvil 422 and the cartridge 424 increases in a stepped configuration from distal ends 422a, 424a to proximal ends 422b, 424b. In the exemplary embodiment, the face 428 of the cartridge 424 includes segments 430, 432, and 434. Each segment 430, 432, 434 resides in a plane that differs from planes for each of the other segments 430, 432, 434 to produce three different gap dimensions with the face 426 of the anvil 422. The different gap dimensions may be related to the difference in thickness of the stomach 10 along the staple line 12, as is described above. As shown, the staples 198 in each segment 430, 432, 434 may have the same open leg length. To accommodate for the difference in height in each segment 430, 432, 434, the staple drivers 200 vary in height by segment 430, 432, 434. Thus, as the wedge (not shown) forces the staple drivers 200 toward the anvil 422, the staples 198 will be fully pushed out of the staple channels. While three segments 430, 432, 434 are shown, it will be appreciated that the face 428 of the cartridge 424 may be defined by at least two segments and may be defined by more than three segments. It should be appreciated that there may be other configurations that allow for the staples 198 to pass through the staple channels of varying height.

Once the end effector 420 has been fully actuated, the staples 198 within each individual segment 430, 432, 434 will generally have the same open leg length, as shown in FIG. 15B, but differ in closed leg lengths compared to each of the adjacent segments 430, 432, 434 due to the stepped configuration of the gap between the anvil 422 and the cartridge 424. By way of example only, the staples 198 near the proximal end of the staple line 12 will have a greater closed leg length than the staples 198 near the distal end of the staple line 12. In an advantageous aspect of the present invention, the stepped configuration of the cartridge 424 aids in providing a consistent staple deformation by taking into account the varying thickness of the stomach 10. Further, the surgeon is not required to determine what size staples to use based on the expected thickness of the stomach 10.

It should be realized that aspects of the present invention are not limited to the illustrated arrangements in FIGS. 15A-15B. For instance, the face of the anvil may include a stepped configuration similar to that of the cartridge 424 shown in FIG. 15A and provide a similar tiered difference in gap between opposing faces of the anvil and the cartridge. By way of example, with reference to FIGS. 16A and 16B, in which like reference numerals refer to like features of FIGS. 15A and 15B, an end effector 440 includes an anvil 442 and a cartridge 444 where a gap between the anvil 442 and the cartridge 444 increases in a stepped configuration from the distal ends 442a, 444a to the proximal ends 442b, 444b. In the exemplary embodiment, the face 426 of the anvil 442 includes segments 450, 452, and 454. Each segment 450, 452, 454 resides in a plane that differs from planes for each of the other segments 450, 452, 454 to produce three different gap dimensions with the face 428 of the cartridge 444. The different gap dimensions may be related to the difference in thickness of the stomach 10 along the staple line 12, as is described above. As shown, the staples 198 in each segment 450, 452, 454 may have the same open leg length. Since there is no height difference in the cartridge 444, the staple drivers 200 also have the same height in each segment 450, 452, 454. Thus, as the wedge (not shown) forces the staple drivers 200 toward the anvil 422, the staples 198 will be fully pushed out of the staple channels. While three segments 450, 452, 454 are shown, it will be appreciated that the face 426 of the anvil 442 may be defined by at least two segments or may be defined by more than three segments.

Figures 16A, 16B:
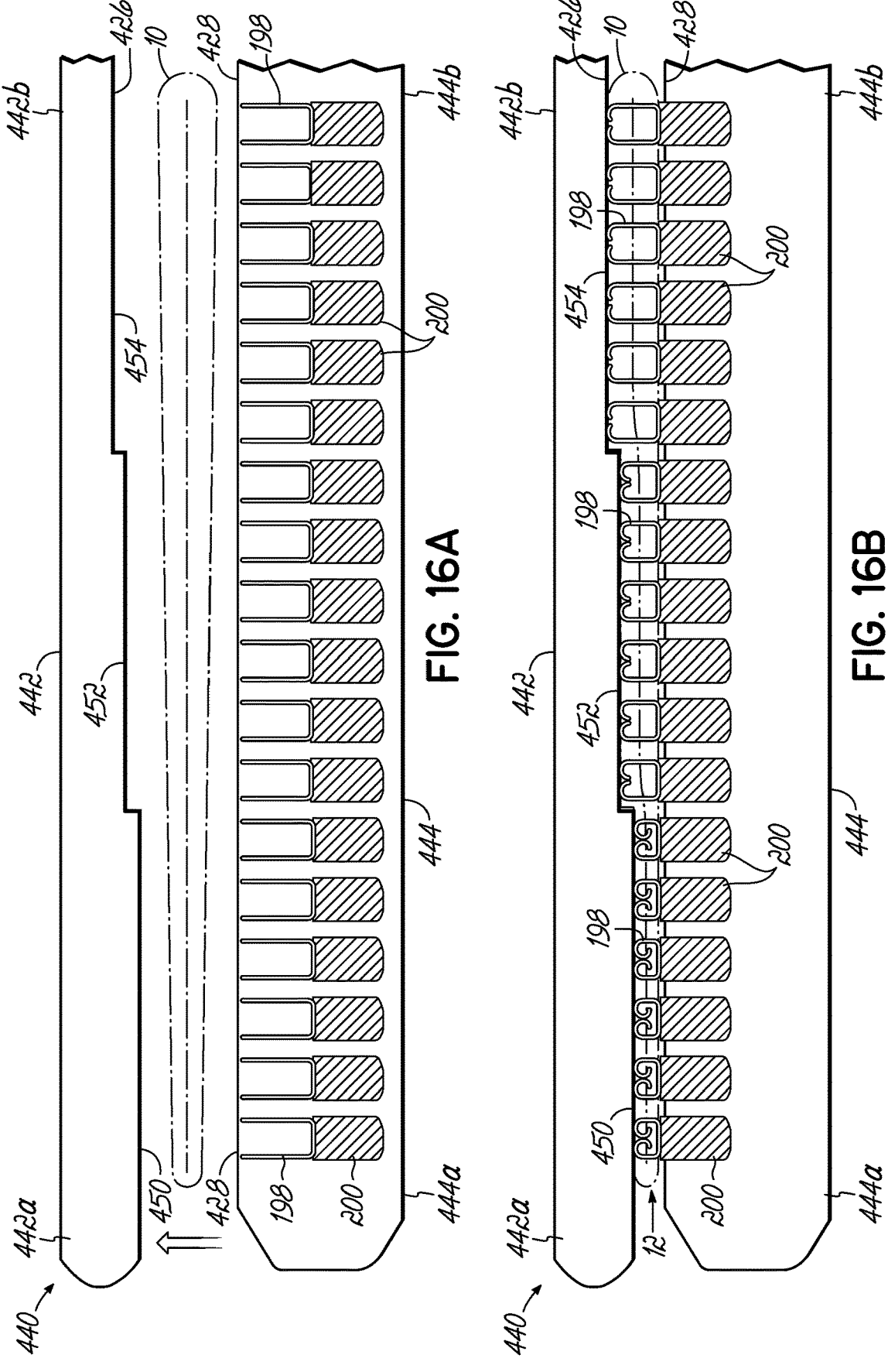
FIG. 16A is a schematic elevation view of an end effector according to one embodiment of the present invention.
FIG. 16B is a schematic elevation view of the end effector of FIG. 16A positioned on a stomach after actuation of an endocutter stapling device according to one embodiment of the invention to complete a staple line.
Figures 17A, 17B:
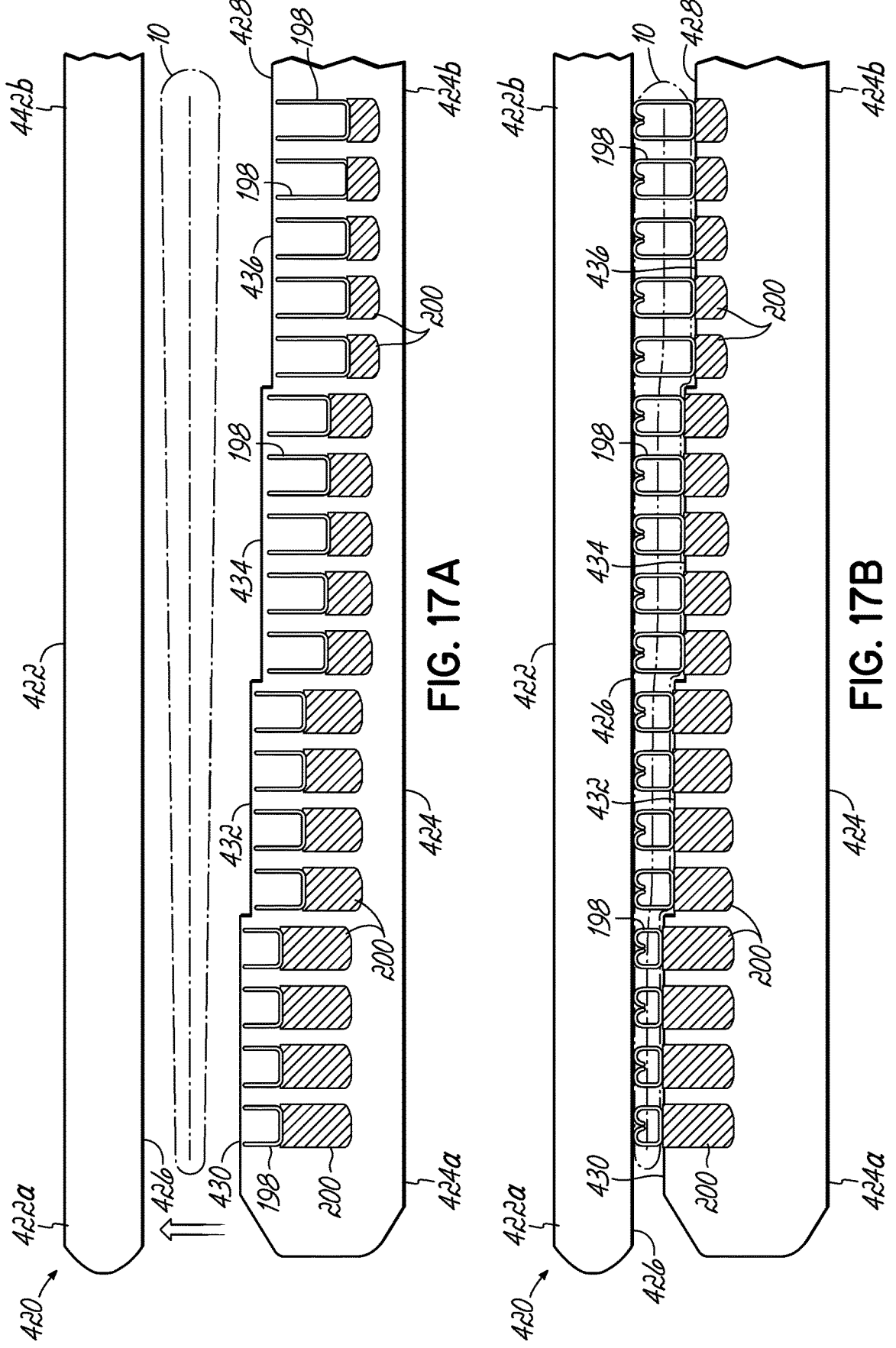
FIG. 17A is a schematic elevation view of an end effector according to one embodiment of the present invention.
FIG. 17B is a schematic elevation view of the end effector of FIG. 17A positioned on a stomach after actuation of an endocutter stapling device according to one embodiment of the invention to complete a staple line.

While each staple 198 within each segment 430, 432, 434 as is shown in FIG. 15A and each staple 198 within each segment 450, 452, 454 as is shown in FIG. 16A, has an equivalent open leg length, embodiments of the present invention are not limited to embodiments in which each staple 198 has an equivalent open leg length. With reference to FIGS. 17A and 17B, in which like reference refer to like features throughout the figures. In an exemplary embodiment, the end effector 420 cartridge 424 includes four segments 430, 432, 434, 436 where the open leg lengths of the staples 198 in each segment differ. The open leg lengths of staples vary among manufacturers. For instance, blue, gold, green, and black colors may be used to indicate staple having open leg lengths of 3.5 mm, 3.8 mm, 4.1 mm, and 4.4 mm, respectively. By way of example only, and not limitation, the segments 430, 432, 434, 436 may include black, green, gold, and blue staples, respectively. While the staples 198 within each segment 430, 432, 434, 436 are shown as having the same open leg length, it will be appreciated that the open leg lengths of the staples 198 within each segment 430, 432, 434, 436 may be different, as is described below. The segments 430, 432, 434, 436 may differ in relative proportion and so embodiments of the present invention are not limited to each segment 430, 432, 434, 436 having the same relative length. As a result, the number of staples 198 in each segment 430, 432, 434, 436 may be different.

Figure 18:
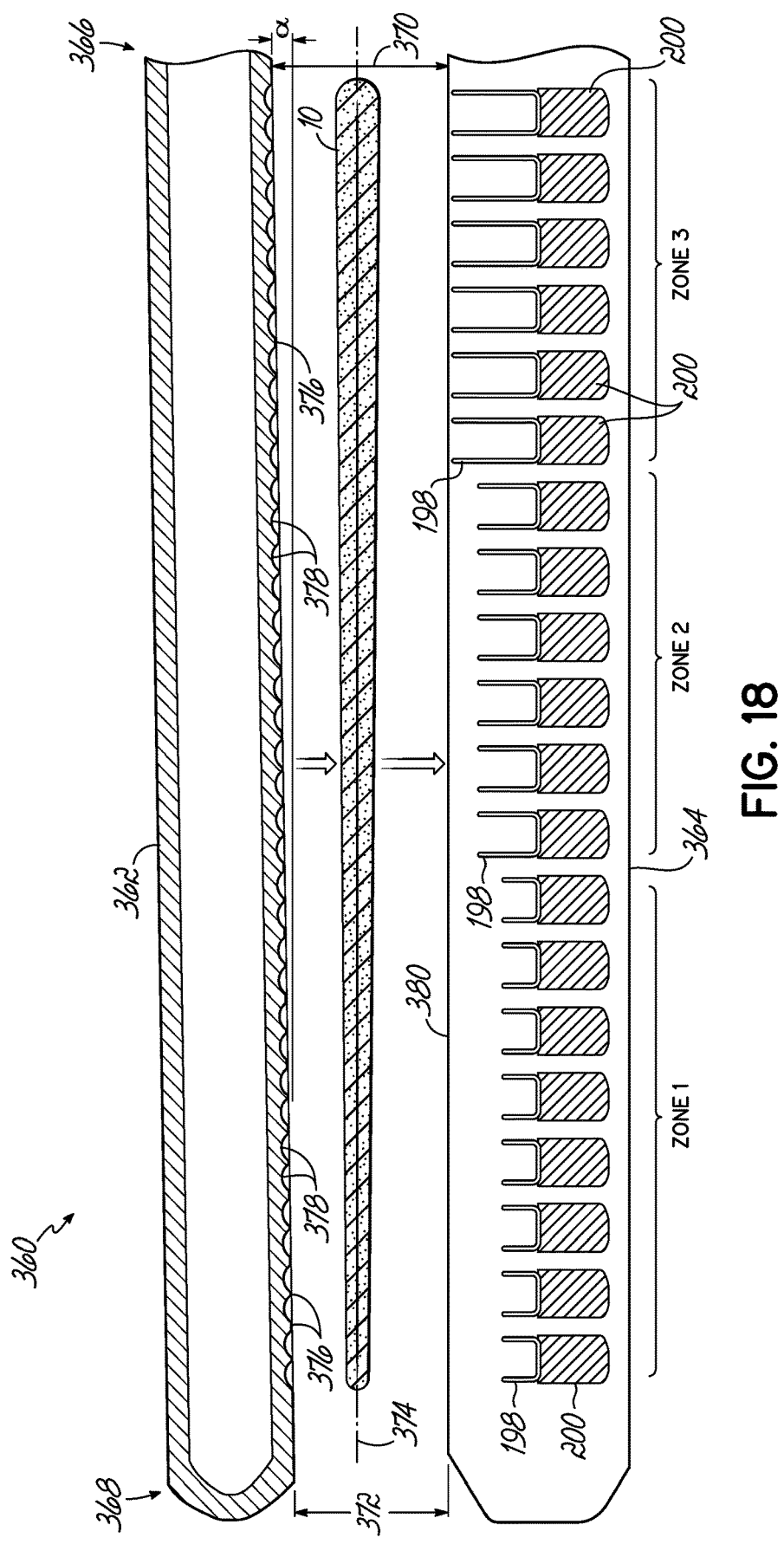
FIG. 18 is a schematic elevation view of an end effector according to one embodiment of the present invention.

As is described above with respect to FIG. 11, in one embodiment, the proximal gap 370 and the distal gap 372 may be different and the face 376 of the anvil 362 may be oriented at an angle a with respect to the face 380 of the anvil 362. Where the gap between the distal end 368 and the proximal end 366 increases linearly, the angle a between the face 376 of the anvil 362 and the face 380 of the cartridge 364 may be determined. In a similar configuration and with reference to FIG. 18, the end effector 360 may include zones of staples 198, with one or more zones having staples 198 of different open leg lengths. The angle a may be used to determine the incremental increase in the gap between the anvil 362 and the cartridge 364 for the purpose of selecting different staples 198 for the zone. Based on this incremental increase, the cartridge 364 may be divided into, for example, zones 1, 2, and 3, as shown. The dimensions of each zone 1, 2, and 3 may be determined according to a minimum closed leg length necessary to adequately staple the tissue in that zone. And, the staples 198 in each zone may have an open leg length that exceeds a minimum open leg length necessary to provide the minimum closed leg length within that zone.

Figures 19, 20A:
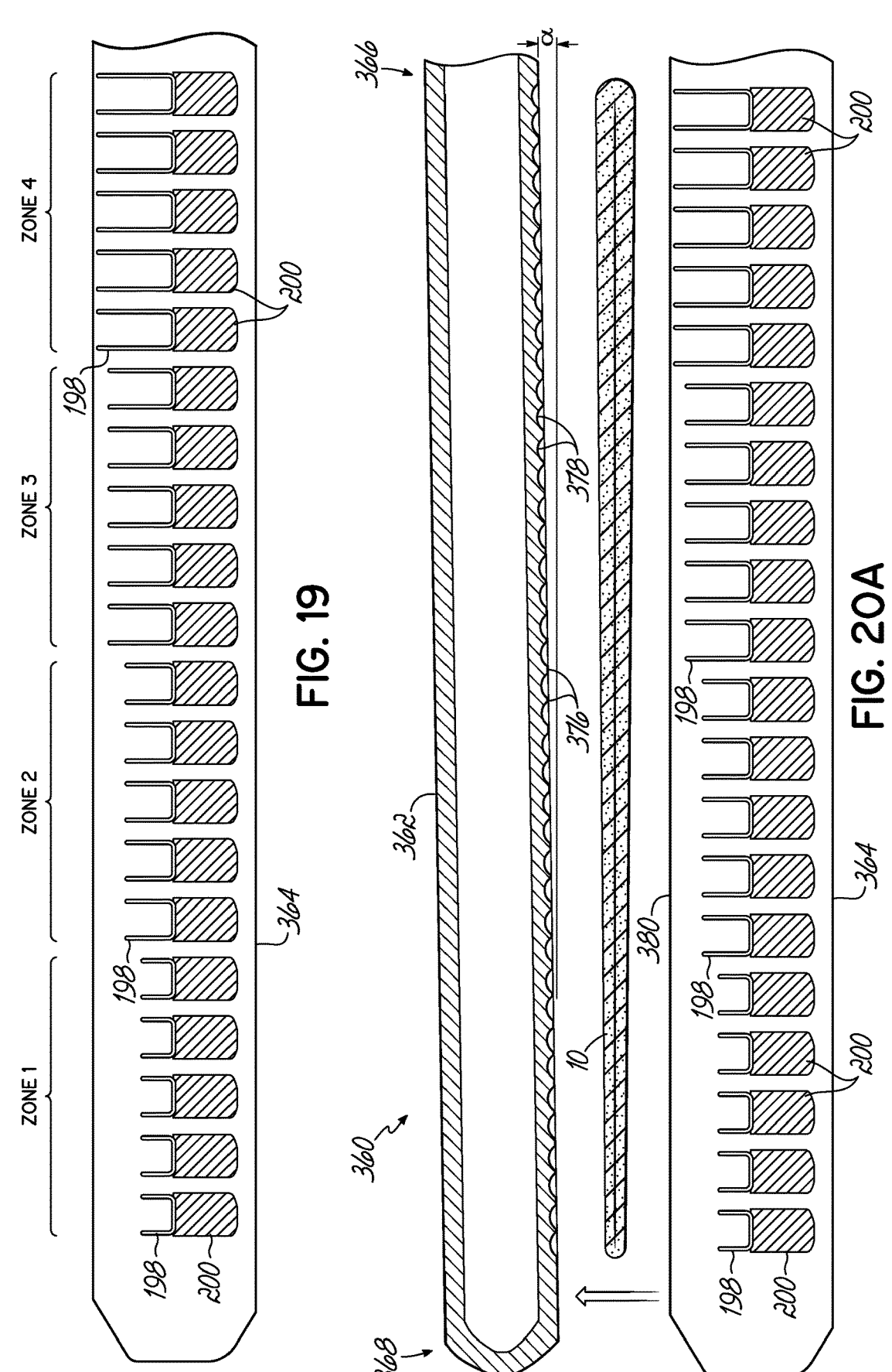
FIG. 19 is a schematic elevation view of a cartridge according to one embodiment of the present invention.
FIG. 20A is a schematic elevation view of an end effector including the cartridge of FIG. 19.

Determining the minimum closed leg length according to zones allows for a determination of the appropriate open leg length for the staples 198 in the respective zone. With reference to FIG. 19, and by way of example, and not limitation, the distal gap may be about 1.7 mm, and the proximal gap may be about 3.3 mm. The angle a may be approximately 0.367 degrees. This information may be used to calculate zones of different open leg lengths. The number and length of each zone may be varied based on the proximal gap and distal gap of the end effector 360. In FIG. 19, the cartridge 364 includes three zones of, for example, blue (3.5 mm), gold (3.8 mm), and green (4.1 mm) open staple leg lengths from the distal end to the proximal end. Embodiments of the present invention are not limited to the illustrated arrangement, where the cartridge 364 includes four zones of staples 198 having different open leg lengths. Other alternative arrangements may also be possible.

Figures 20B, 20C:
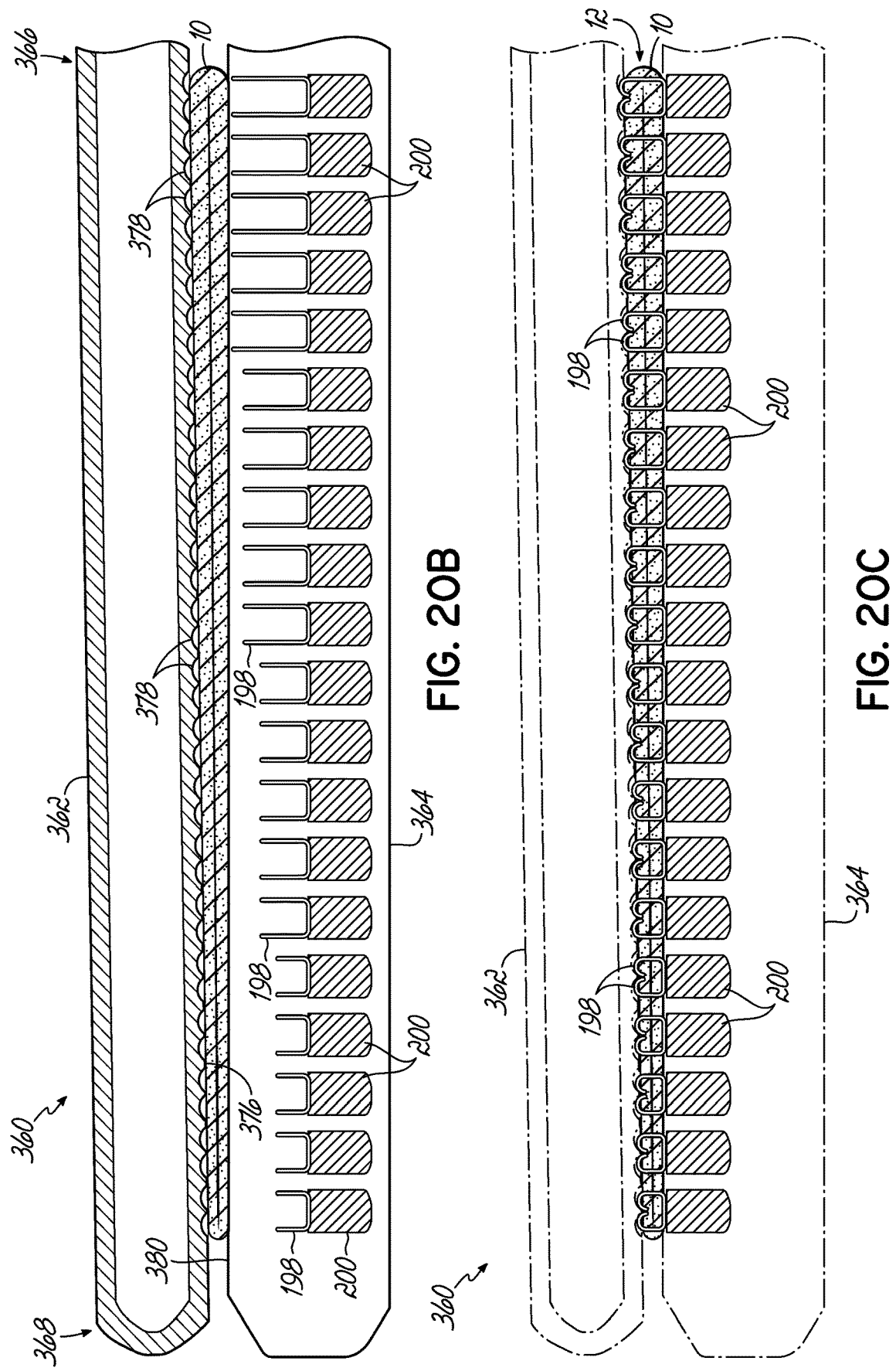
FIG. 20B is a schematic elevation view of the end effector of FIG. 20A during compression of the stomach.
FIG. 20C is a schematic elevation view of the end effector of FIG. 20A following stapling of the stomach.

In one embodiment, and with reference to FIGS. 20A-20C, using the exemplary color-coded open staple leg lengths, the zones 1, 2, 3, and 4 of the cartridge 364 may use blue (3.5 mm), gold (3.8 mm), green (4.1 mm), and black (4.4 mm) staples, respectively. Each color is associated with a specific open leg length. After completion of the staple line, the staples 198 within each zone 1, 2, 3, and 4 may have approximately the same closed leg length, as shown in FIG. 20C.

Figures 21, 22:
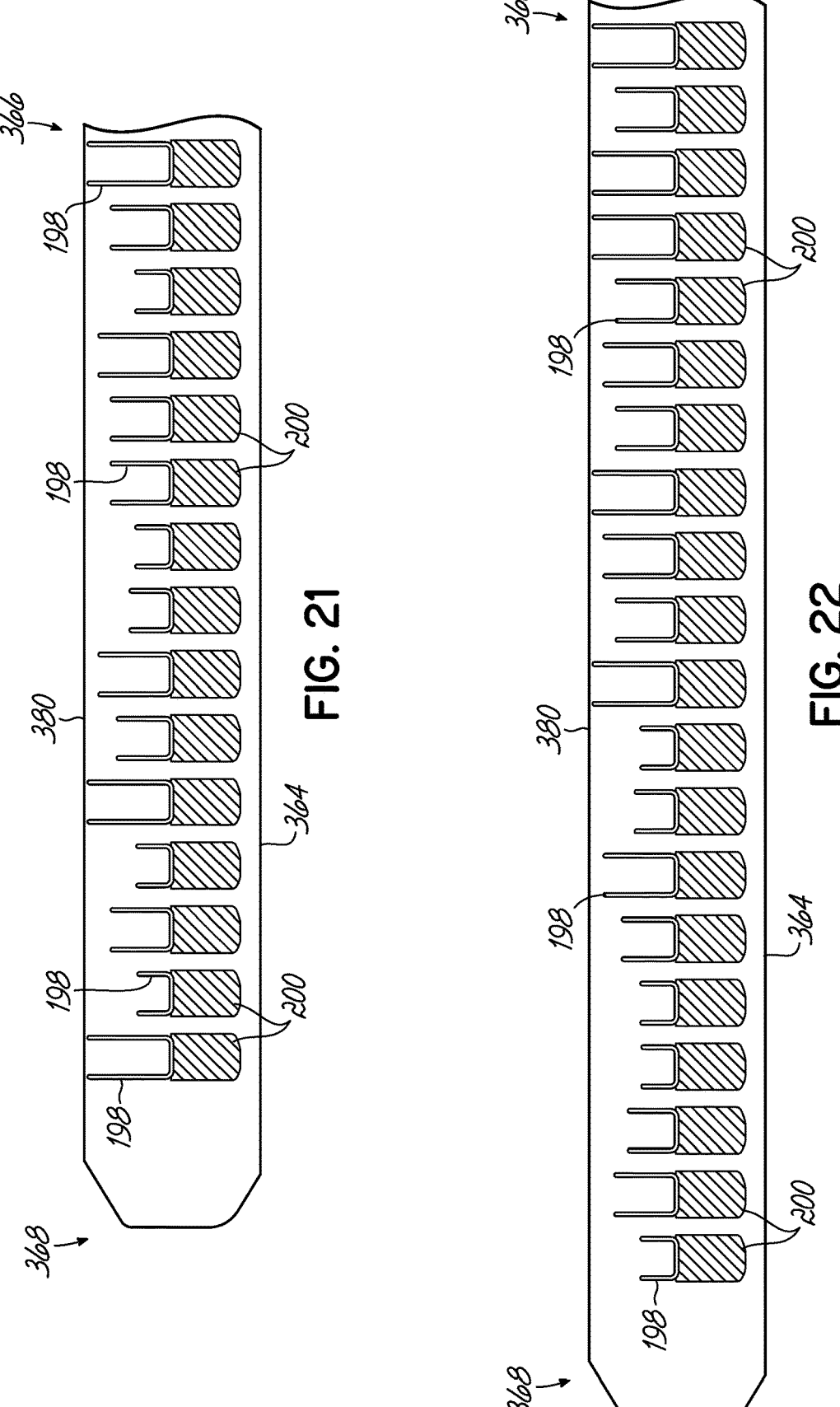
FIG. 21 is a schematic elevation view of a cartridge according to one embodiment of the present invention.
FIG. 22 is a schematic elevation view of a cartridge according to one embodiment of the present invention.

According to one aspect of the present invention and with reference to FIG. 21, in one embodiment, the cartridge 364 may be randomly loaded with staples 198 having different open leg lengths. In this manner, a random fill of the cartridge 364 may be advantageous in that it "automatically" adjusts for the variation in tissue thickness along the length of the staple line 12. That is, within the random staples 198 it is likely that one or more will exceed the minimum open leg length necessary to provide the necessary closed leg length. After the staple line 12 is complete, the closed leg lengths of the staples 198 will vary depending on the open leg length and the gap between the cartridge 364 and the anvil (not shown). Randomly filling the cartridge 364 with staples 198 of different sizes is an improvement over conventional staplers where the surgeon is required to determine what size staples 198 should be used because at least a portion of the staples 198 in the random fill are likely to be the appropriate length.

In one embodiment, the changing thickness of the stomach may be used in part to determine what minimum open leg length to use in each zone of a cartridge. A random selection of different staples may be made with respect to that minimum. That is, a distribution of staples of different open leg lengths may be selected with staples having open leg lengths above and below the minimum open leg length. With reference to FIG. 22, in one embodiment, the staples 198 having different open leg lengths may be placed within the cartridge 364 according to a probability based on the average stomach thickness at that location. This is similar to the zones described above but with staples having different open leg lengths within a particular zone. Within each zone, the staples 198 may be randomly filled. Further in this regard, the change in the gap between the cartridge 364 and the anvil (not shown) may be calculated along the length of the cartridge 364 and may be utilized to further improve the probability determination on a zone by zone basis. As is shown in FIG. 22, staples 198 having a larger open leg length may be used more frequently near the antrum or near the proximal end 366 of the cartridge 364, and staples 198 having a shorter open leg height may be used more frequently near the fundus or near the distal end 368 of the cartridge 364.

In one embodiment using these exemplary staples, staples 198 in one or more zones of the cartridge 364 adjacent the antrum 24 may include about 70% black staples, about 20% green staples, and about 10% blue staples. Staples 198 in one or more zones of the cartridge 364 adjacent the fundus 26 may include about 90% blue staples and about 10% green staples. Finally, staples 198 in one or more zones of the cartridge 364 between the antrum 24 and the fundus 26 may include about 33% black staples, about 33% green staples, and about 33% blue staples. Including staples 198 having varying open leg lengths based on a determined probability of the tissue thickness advantageously provides an improved likelihood that one or more staples 198 are appropriately sized within any given zone based on the varying tissue thickness of the stomach 10.

Figures 23, 23A, 23B:
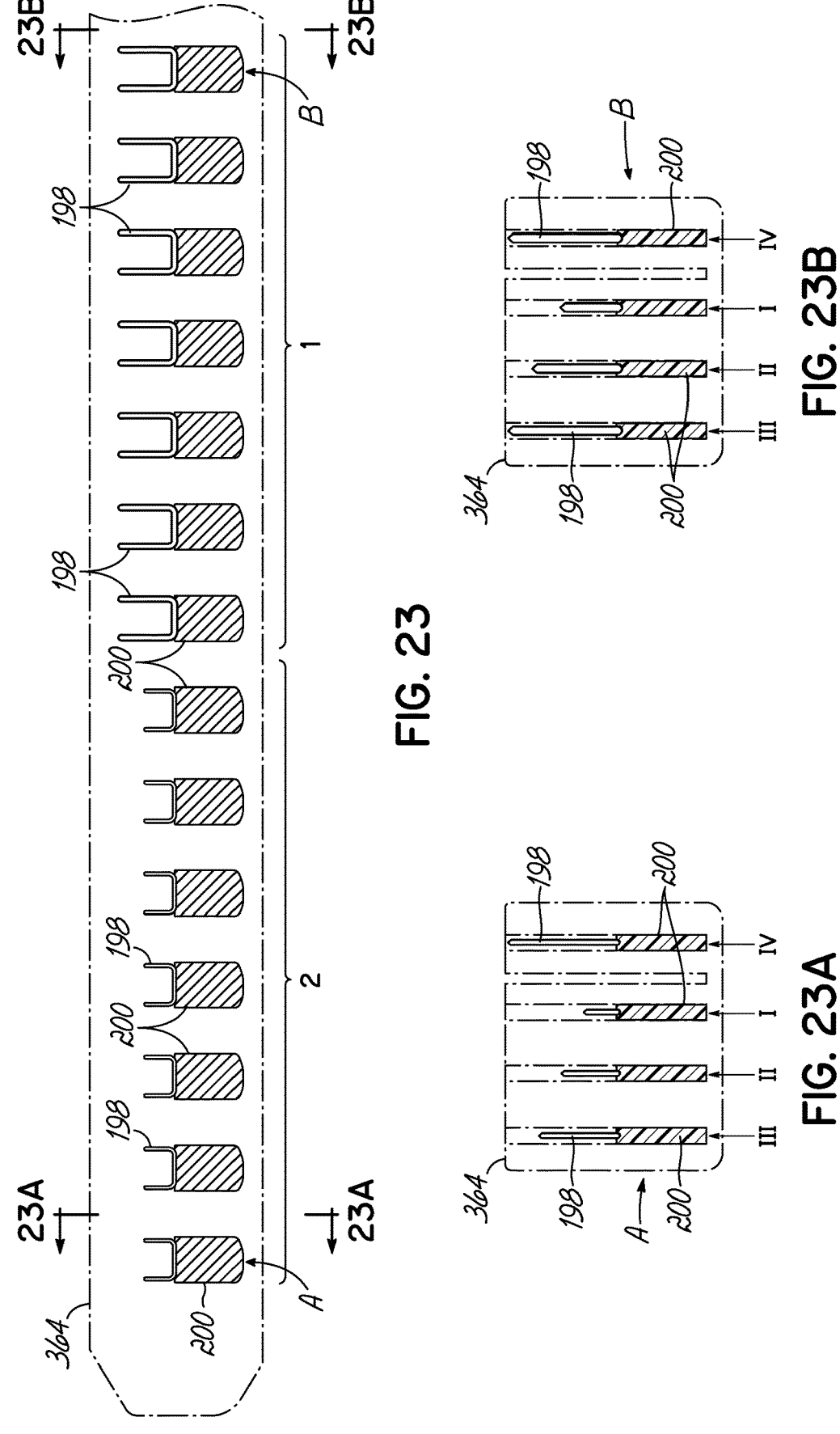
FIG. 23 is a schematic elevation view of a cartridge according to one embodiment of the present invention.
FIGS. 23A and 23B are cross-sectional views of the cartridge of FIG. 23 taken along section line 23A-23A and 23B-23B, respectively.
Figure 23C:
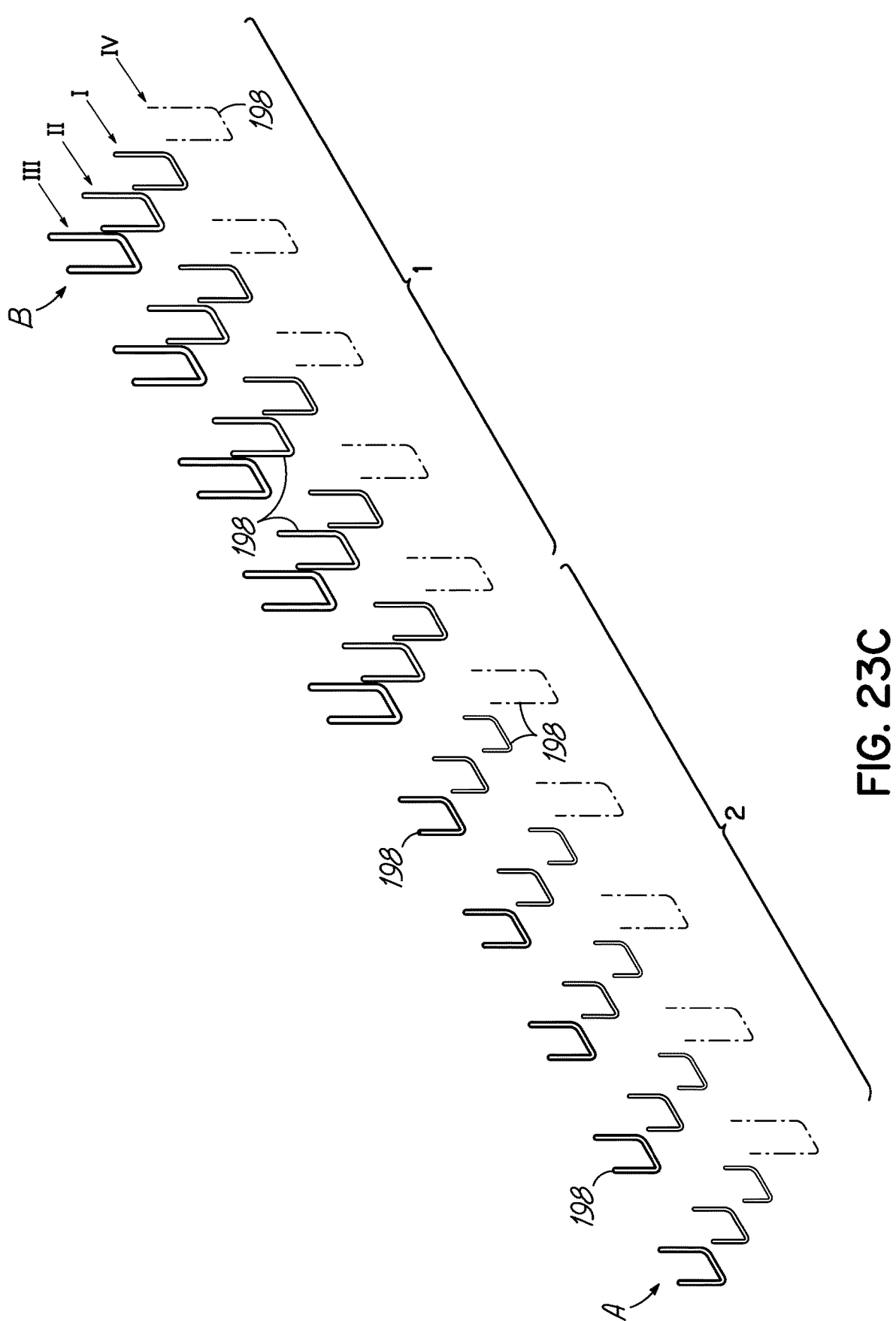
FIG. 23C is a perspective view of an arrangement of staples in a cartridge according to one embodiment of the invention.

With reference to FIGS. 23 and 23A-23C, in one embodiment, in which like reference numerals refer to like features throughout the figures, the cartridge 364 includes one or more zones of staples 198 in which the open leg lengths of the staples 198 change according to a particular pattern in one or more directions. That is, the staples 198 are not randomly distributed, as described above. Rather, the staples 198 are arranged in a predetermined, organized pattern. By way of example, the staples 198 may be arranged to change size in a direction perpendicular to the longitudinal axis of the cartridge 364, referred to as columns, and/or in a direction parallel to the longitudinal axis of the cartridge 364, referred to as rows. FIG. 23 depicts a single row of staples 198 that may be divided into zones 1 and 2 of staples 198. Each zone 1 and 2 may have a single predetermined open leg length of staple 198, as shown. The predetermined pattern of the staples 198 having different open leg lengths along the rows and/or columns of the cartridge 364 may be determined based upon the expected closed leg length in each zone, as is described above.

With reference to FIGS. 23A and 23B, the cartridge 364 may include four rows I, II, III, and IV of staples 198. Each row of staples 198 within each zone may be of different open leg length and/or gauge. For example, column A, shown in FIG. 23A, may include staples 198 of a different gauge than the staples 198 in column B, shown in FIG. 23B, though the open leg length of the staples 198 in the corresponding rows of each column may be the same. Taking each of the rows and columns shown in FIGS. 23-23B into account, each zone with the corresponding rows and columns may be shown in FIG. 23C. Zones 1 and 2 include staples 198 of different open leg lengths. Zones 1 and 2 also differ in the wire diameter, or gauge, of the staples 198. By way of example, and with continued reference to FIG. 23C, zone 1 may include rows I, II, and III of staples 198 having open leg lengths of 4 mm, 4.5 mm, and 5 mm, respectively, in each column. Zone 2 may include rows I, II, and III of staples 198 having open leg lengths of 3 mm, 3.5 mm, and 4 mm, respectively. The staples 198 of row IV is on the to-be-excised portion of stomach 10 and is shown in phantom. The number and length of the zones will vary based on the proximal and distal gaps of the end effector as is described above. Thus, it should be realized that aspects of the present invention are not limited to the illustrated arrangement, where the cartridge 364 includes two zones of rows and columns having staples 198 of different open leg lengths and/or different gauges. Other alternative arrangements may also be possible.

Figures 24A, 24B:
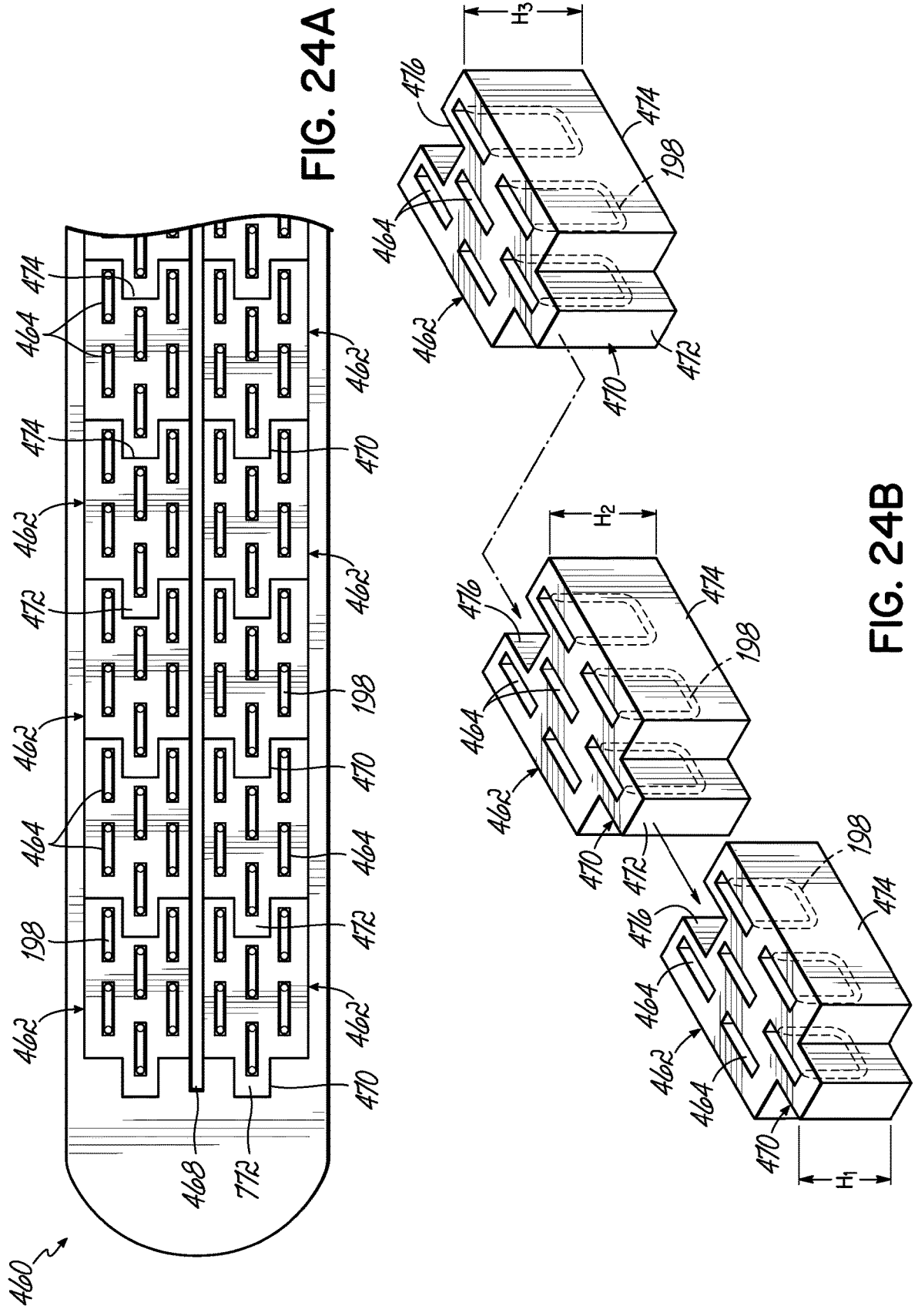
FIG. 24A is a plan view of a cartridge according to one embodiment of the present invention.
FIG. 24B is an enlarged perspective view of a magazine of FIG. 24A illustrating the assembly of the cartridge.

With reference to FIG. 24A, in one embodiment, a cartridge 460 may be configured to include a plurality of magazines 462 that may be separated and reassembled. Each magazine 462 may include three rows 464 of staples 198 and be assembled to define a channel 468 for a cutting knife (not shown). The stomach 10 is often stapled on both sides of the cutting blade to prevent the release of undesirable contents of the excised portion of the stomach into the abdominal cavity. While the rows 464 on each side of the channel 468 are specifically shown to mirror one another, it would be readily appreciated that, in alternate embodiments, the rows 464 of staples 198 on the side of the stomach that will be excised (anatomical left) need not mirror the rows of staples on the side of the resultant stomach pouch (anatomical right).

Figure 24C:
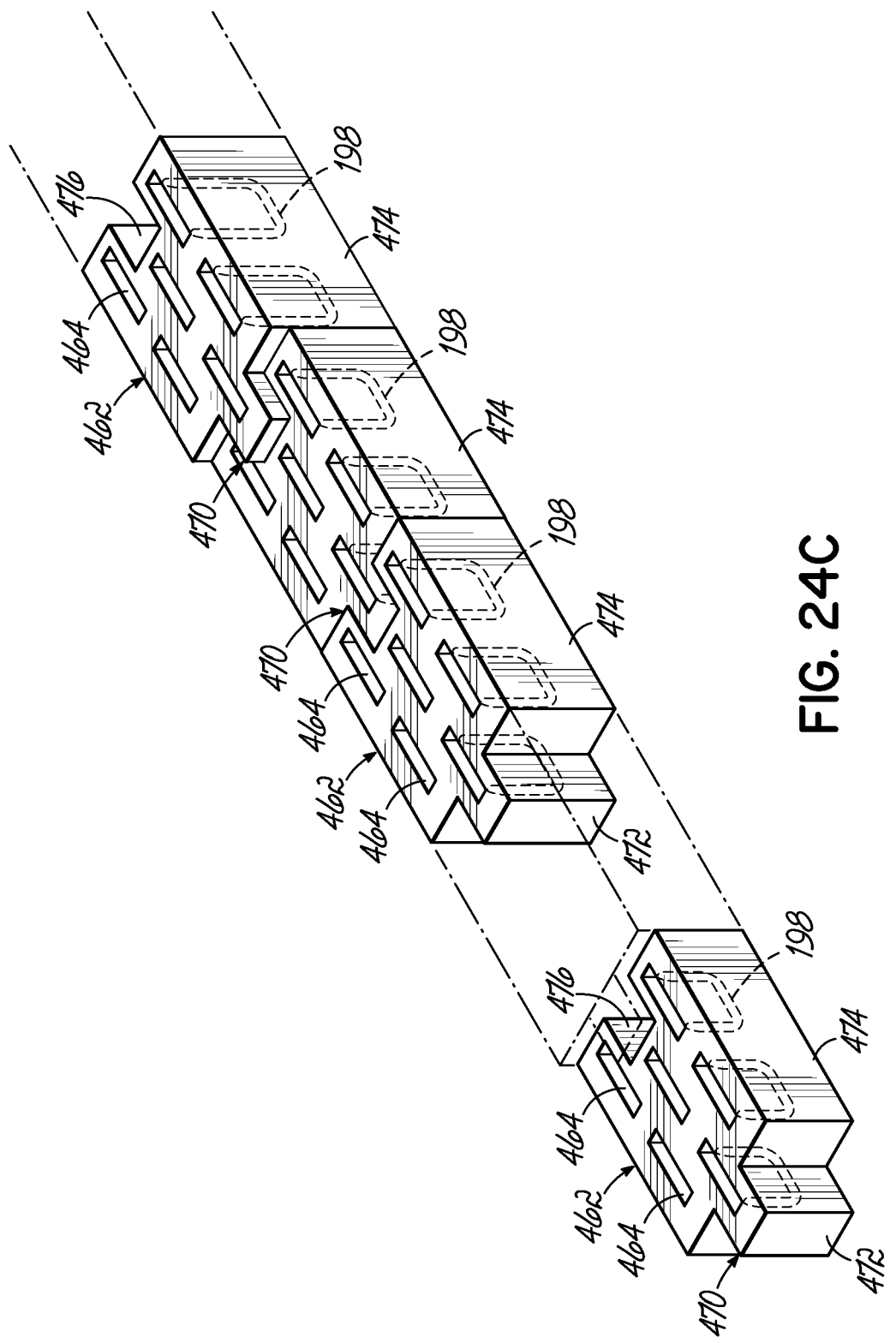
FIG. 24C is an enlarged perspective view of a portion of the cartridge of FIG. 24A following assembly according to FIG. 24B.

With reference to FIGS. 24A, 24B, and 24C, the magazines 462 may have an interlocking feature 470 that, in the exemplary embodiment shown, includes a projection 472 that extends outwardly from a main body 474 of the magazine 462 and a recess 476 that extends into the main body 474 of the magazine 462. When the magazines 462 are assembled, the adjacent magazines 462 engage each other through abutting contact. More particularly, the projection 472 is positioned within the recess 476 to couple adjacent magazines 462 back-to-back. The interlock between adjacent magazines 462 may more firmly stabilize the cartridge 460 during use but allow the surgeon to adjust the overall length of the cartridge 460. The interlocking feature 470 may also more easily allow for the rows 464 to be positioned with the staples 198 staggered from each adjacent row. By way of example, without limitation, the magazine 462 may be from about 5 mm to about 260 mm in length. In one embodiment, the magazine 462 may be, for example, about 60 mm in length. In this case, four magazines 462 may be used to prepare one staple line. Each magazine 462 may include staples 198 having open leg lengths different from the staples 198 in an adjacent or another magazine 462. Other alternative arrangements may also be possible.

The surgeon may determine which magazine 462 to use based on the included open staple leg lengths and the thickness of the stomach as described above. Further, the magazines 462 may vary in height, as shown in FIGS. 24B and 24C with one or more of the heights H1, H2, and H3 of the magazines 462 differing from one another. In this regard, the gap between the cartridge 460 and the anvil (not shown) may vary along the length of the cartridge 460 in a staggered configuration by each magazine 462. In one embodiment, four magazines 462 from the proximal end to the distal end may include staples 198 having an open leg length of 4.4 mm (black), 4.1 mm (green), 3.8 mm (gold), and 3.5 mm (blue), respectively. When these magazines 462 are placed into the cartridge 460 and the stomach 10 is compressed between the anvil (not shown) and the cartridge 460, the gap at each of the four magazines may be 2.3 mm, 2.0 mm, 1.8 mm, and 1.5 mm, respectively. In this regard, the surgeon may advantageously adapt the cartridge 460 depending on the anatomy of the individual patient. Those of ordinary skill in the art will recognize that there may be other configurations of magazines 462 useful in embodiments of the present invention.

Figures 25, 26A, 26B:
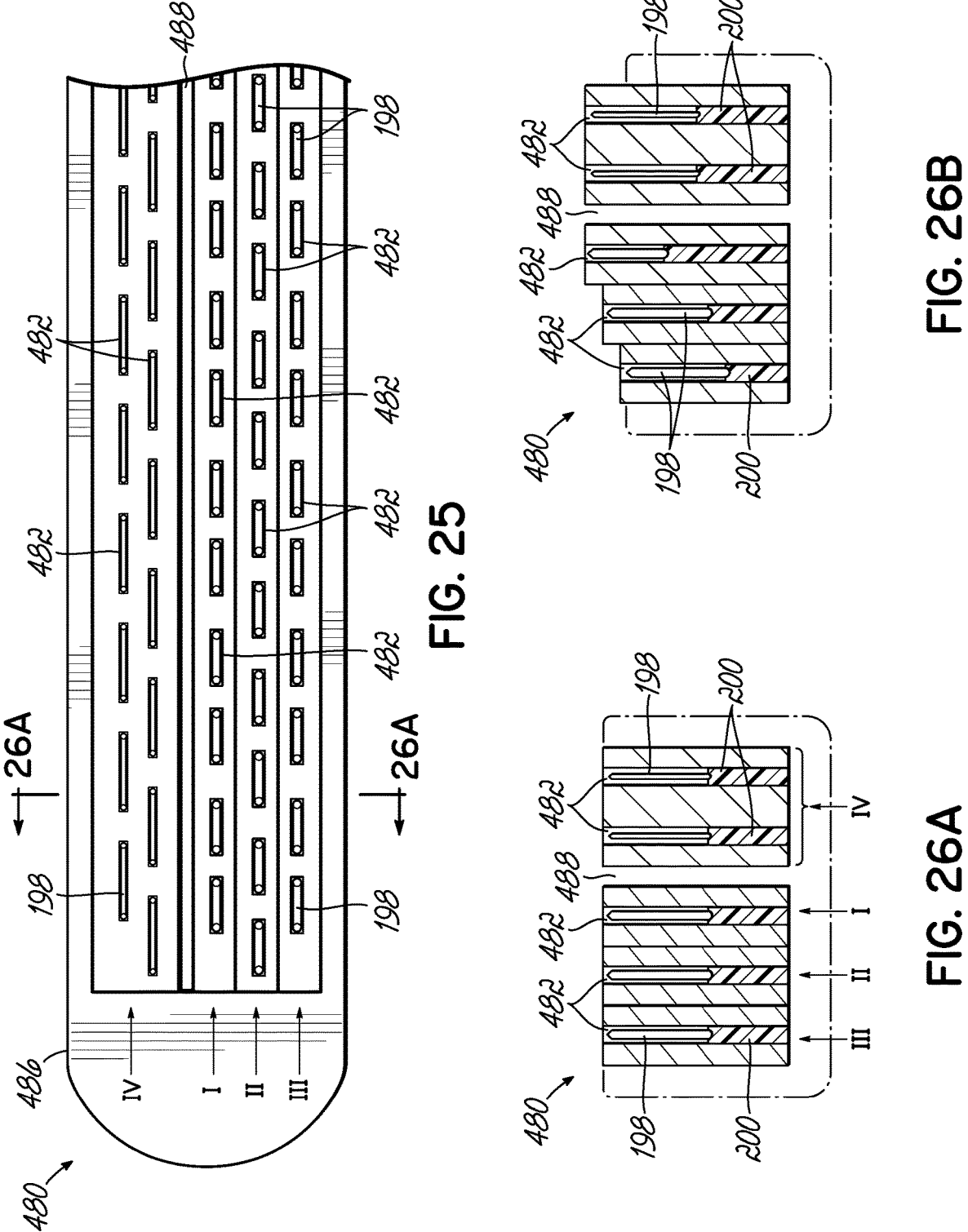
FIG. 25 is a plan view of a cartridge according to one embodiment of the present invention.
FIG. 26A is a cross-sectional view of an end effector according to one embodiment of the invention taken along section line 26A-26A of FIG. 25.
FIG. 26B is a cross-sectional view of an alternative cartridge according to one embodiment of the invention similar to that shown in FIG. 26A.

With reference to FIGS. 25 and 26A and 26B, in one embodiment, a cartridge 480 includes a plurality of magazines 482 that may be elongated as compared to the magazines 462 described above with reference to FIGS. 24A-24C. In one embodiment, each magazine 462 may extend from the proximal end to the distal end of the cartridge 480. Each magazine 482 may include one or more rows of staples 198 in multiple columns. In the exemplary embodiment shown, a separate magazine 482 defines each of rows I, II, III, and IV with row IV having two staggered columns of staples 198. As with the magazines 462 above, each magazine 482 may include staples 198 having different open leg lengths and/or gauges from the staples 198 in adjacent magazines 462. Further, the magazines 462 may vary in height. In this regard, the gap between the cartridge 480 and the anvil (not shown) may vary in the transverse direction, as shown by comparison of FIGS. 27A and 27B. The magazines 482 may be, for example, about 250 mm in length. The surgeon may determine which magazines 482 to use based on the included open staple leg lengths and personal preferences regarding the completed staple line. In one embodiment, the surgeon may choose staples 198 having a larger open leg length adjacent an outer edge 486 of the cartridge 480 and staples 198 having a smaller open leg length adjacent a knife channel 488 in the cartridge 480. In this regard, the surgeon may advantageously adapt the cartridge 480 depending on the anatomy of the individual patient.

Figures 27A, 27B, 27C:
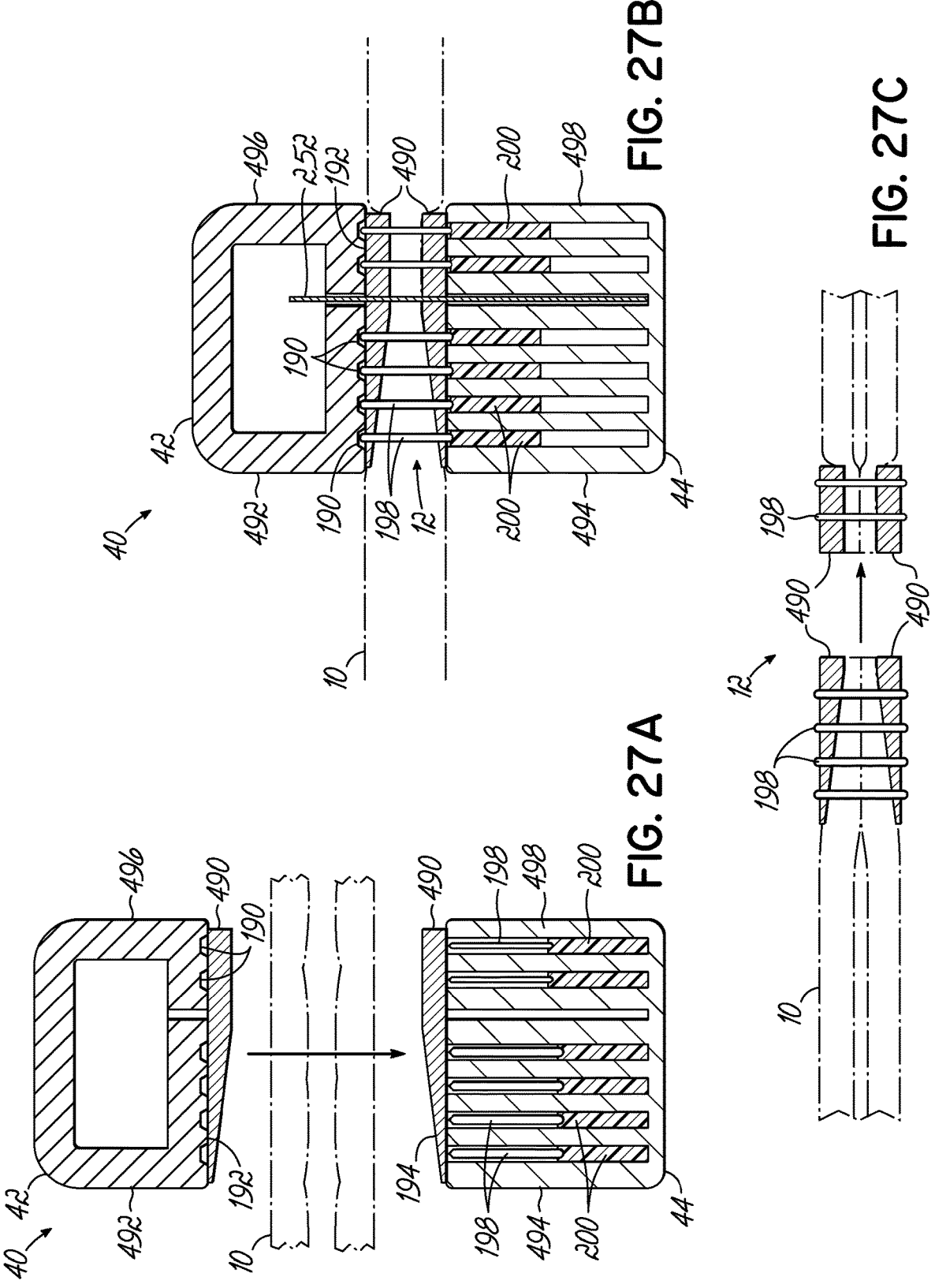
FIGS. 27A and 27B are cross-sectional views of an end effector according to one embodiment of the invention before and after stapling, respectively.
FIG. 27C is a cross-sectional view of the staple line after actuation of an endocutter stapling device according to one embodiment of the invention to complete a staple line.

With reference to FIGS. 27A-27C in which like reference numerals refer to like features throughout the figures, in one embodiment, a shim 490 is coupled to each of the anvil 42 and the cartridge 44. The shims 490 increase in thickness from the first edges 492, 494 to the second edges 496, 498 of the anvil 42 and the cartridge 44. When the stomach 10 is compressed between the anvil 42 and the cartridge 44, the predetermined thickness of the shims 490 provides different levels of compression across the width of the staple line 12, as is shown in FIG. 27B. In other words, the portion of the shims 490 with a greater thickness provides more compression. During actuation of the wedge (not shown), the staple drivers 200 are forced toward the anvil 42, the staples 198 pierce through the shims 490 coupled to each of the anvil 42 and the cartridge 44 to come into contact with the staple pockets 190.

Once the stomach 10 has been stapled, the staples 198 having the same open leg length will also have generally the same closed leg length along the width of the staple line 12 even though the thickness of the stomach gradually decreases toward the edge of the staple line 12. The increased compression along the edge of the resultant stomach pouch aids in providing hemostasis and reducing the possibility of dehiscence. Embodiments of the present invention are not limited to the illustrated arrangement, where both the anvil 42 and the cartridge 44 include a shim 490. In an alternative embodiment, for example, the shim 490 may be coupled to the anvil 42, while the cartridge 44 does not include a shim. Furthermore, the configuration of the shim 490 may be used in conjunction with the shim 410 show in FIGS. 13 and 14A. As a result, the thickness of the shims may change in a direction along the longitudinal axis of the end effector (see e.g., FIG. 13) and may also change in a direction perpendicular to the longitudinal axis of the end effector (see e.g., FIG. 27A).

Figure 28B:
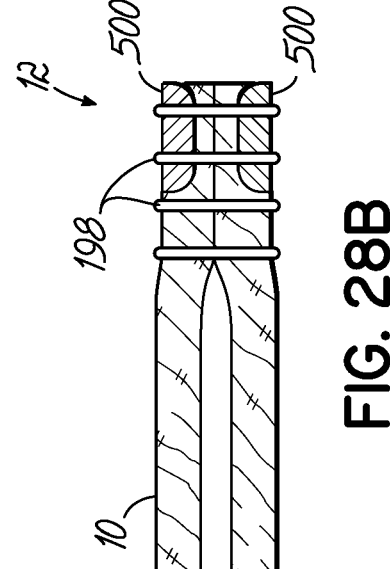
FIG. 28B is a cross-sectional view of the staple line after actuation of the end effector shown in FIG. 28A according to one embodiment of the invention to complete a staple line.
Figure 28A:
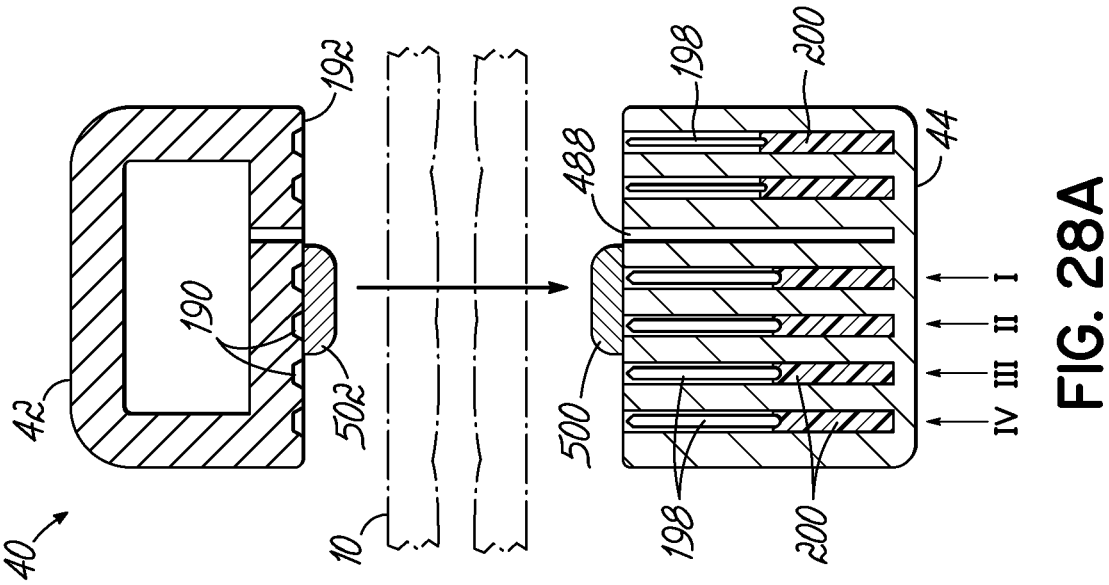
FIG. 28A is a cross-sectional view of an end effector according to one embodiment of the present invention.

With reference to FIGS. 28A and 28B, in which like reference numerals refers to like features throughout the figures, in one embodiment, a shim 500 is positioned on the face 194 of the cartridge 44 adjacent the knife channel 488 over selected rows I and II of staples 198. A second shim 502 is coupled to the face 192 of the anvil 42 and a location that opposes the first shim 500 on the face 194 of the cartridge 44. Once the stomach 10 has been stapled, the shims 500, 502 may form a portion of the staple line 12 and provide a localized increase in compression across a selected width of the tissue in the staple line 12, as is illustrated in FIG. 28B. Alternative arrangements may also be possible.

Figures 29, 30A:
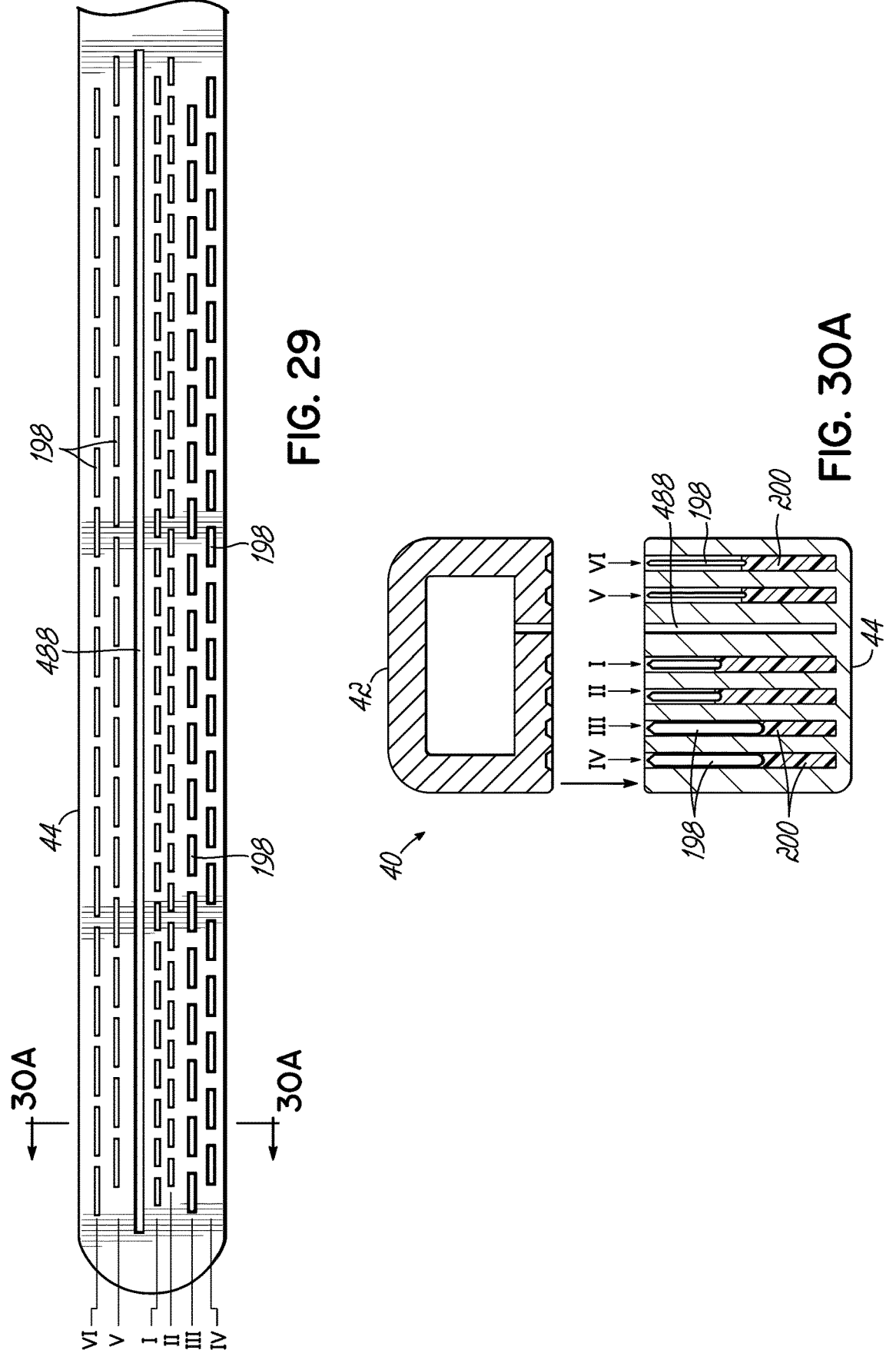
FIG. 29 is a plan view of a cartridge according to one embodiment of the invention.
FIG. 30A is a cross-sectional view of an end effector including a cartridge shown in FIG. 29 taken along section line 30A-30A.

With reference to FIGS. 29 and 30A, in which like reference numerals refer to like features throughout the figures, in one embodiment, the cartridge 44 includes rows I, II, III, V, VI, and VII of staples 198. The staples 198 in one or more of the rows I, II, III, and IV may have different crown lengths, different leg lengths, and/or different wire diameters. In the exemplary embodiment shown, rows I and II may include staples 198 having a shorter leg length than the staples 198 in rows III and VI, as shown in FIG. 30A. Additionally, the staples 198 in rows I and II may have a smaller wire diameter, or gauge, than the wire diameter of the staples 198 in rows III and VI. In this regard, the staples 198 in rows III and VI may provide relatively more mechanical strength to the staple line 12 and the staples 198 and rows I and II. Instead, the staples 198 of rows I and II may provide improved hemostasis compared to the staples 198 in rows III and VI. As discussed above, the rows of staples on the to-be-excised side of the stomach 10 need not match or be similar to the rows of staples 198 on the side of the resultant stomach pouch. For example, rows V and VII may include staples 198 having a similar crown length as the staples 198 in rows III and VI. In one embodiment, the crown length and wire diameter of the staples 198 in each of the rows I, II, III, V, VI, and VII may vary along the length of the cartridge 44 as described above.

Figures 30B, 30C:
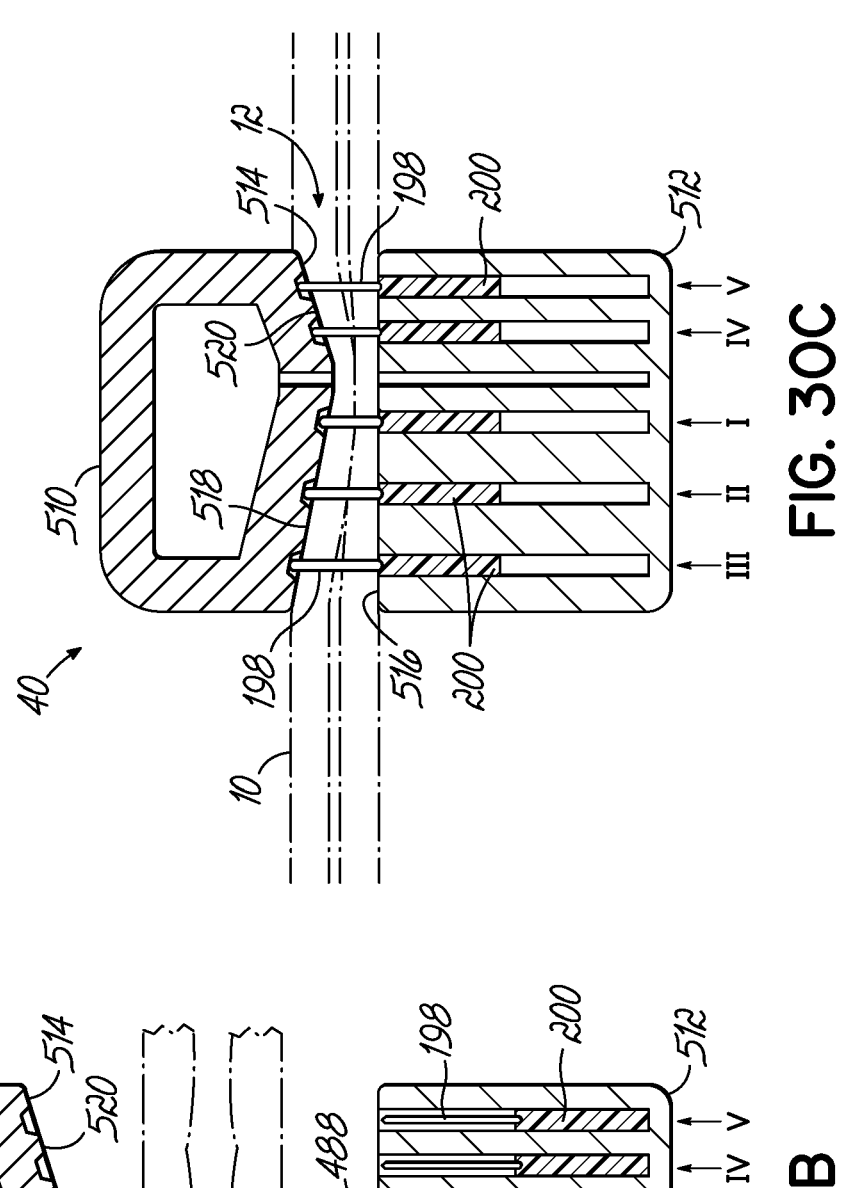
FIG. 30B is a cross-sectional view of an end effector similar to that of FIG. 30A according to one embodiment of the present invention.
FIG. 30C is a cross-sectional view of the end effector of FIG. 30B during stapling of a stomach according to one embodiment of the invention.

With reference to FIGS. 30B and 30C, in which like reference numerals refer to like features throughout the figures, in one embodiment, the end effector 40 includes an anvil 510 and a cartridge 512. The anvil 510 has an anvil face 514, and the cartridge 512 has a face 516, which opposes the face 514 of the anvil 510. As shown, the face 514 as an irregular configuration that does not mirror the planar surface defined by the face 516 of the cartridge 512. In the configuration shown, the anvil 510 has a cross-sectional configuration in which the face 514 is generally V-shaped. In this regard, the face 514 may include two sloped portions 518 and 520 that intersect the knife channel 488 in the anvil 510. The gap between the anvil 510 and the cartridge 512 varies side to side, that is, between the sloped portion 518 and the face 516 and between the sloped portion 520 and the face 516. In the embodiment shown, each row of staples 198 in the cartridge 512 includes staples 198 having the same open leg length. By way of example only, the gap is greater at the outside edges of the anvil 510 and the cartridge 512 than the gap adjacent edges of the knife channel 488. Due to the angle of the sloped portions 518 and 520, the staple pockets 190 will be separated by different distances as compared to an anvil face that is parallel to the face of a cartridge (for example, as shown in FIG. 6A). Further, the spacing of the staple pockets 190 between the sloped portion 518 may differ from the spacing of the staple pockets 190 of the sloped portion 520. More specifically, the angle of the sloped portion 518 relative to the cartridge 512 may be used to determine the location of each staple pocket 190 in the slope portion 518. The same determination may be made with respect to the sloped portion 520. By way of example only, and not limitation, the anvil 510 may be about 2.5 mm wide and may be spaced about 1.0 mm from the cartridge 512 adjacent the knife channel 488 and about 1.4 mm at the edge of the anvil 510. In this embodiment, the angle of the sloped portions 518 and 520 may each be about 10.8 degrees off parallel with respect to the face 516. Where the cartridge 512 has rows I, II, and III of staples 198 that are spaced about 1.25 mm apart, the corresponding rows of pockets 190 in the sloped portion 518 may be spaced about 1.27 mm apart from the row II and may be spaced 2.55 mm apart from the row III.

During activation of the end effector 40, the wedges (not shown) push the staple drivers 200 and the staples 198 toward the anvil 510. Where the same wedge (not shown) forces the staples 198 toward the anvil 510, the staples 198 in row I contact the staple pockets 190 before the staples 198 in rows II and III because of the shorter distance to the sloped portion 518 proximate row I. The staples 198 in row II contact the staple pockets 190 in the face 514 before the staples 198 in row III for the same reason.

Once the stomach 10 has been stapled, the staples 198 having the same open leg length may have different closed leg lengths along the width of the staple line, as is illustrated in FIG. 30C. In this regard, the staples 198 in row I may have a smaller closed leg length compared to the staples 198 in rows II and III. Similarly, the staples 198 in row III may have a larger closed leg length than the staples 198 in rows I and II. In this configuration, the compression provided by the end effector 40 and difference in closed leg length of the staples 198 across the width of the staple line 12 may improve the integrity of the staple line 12.

Figure 31:
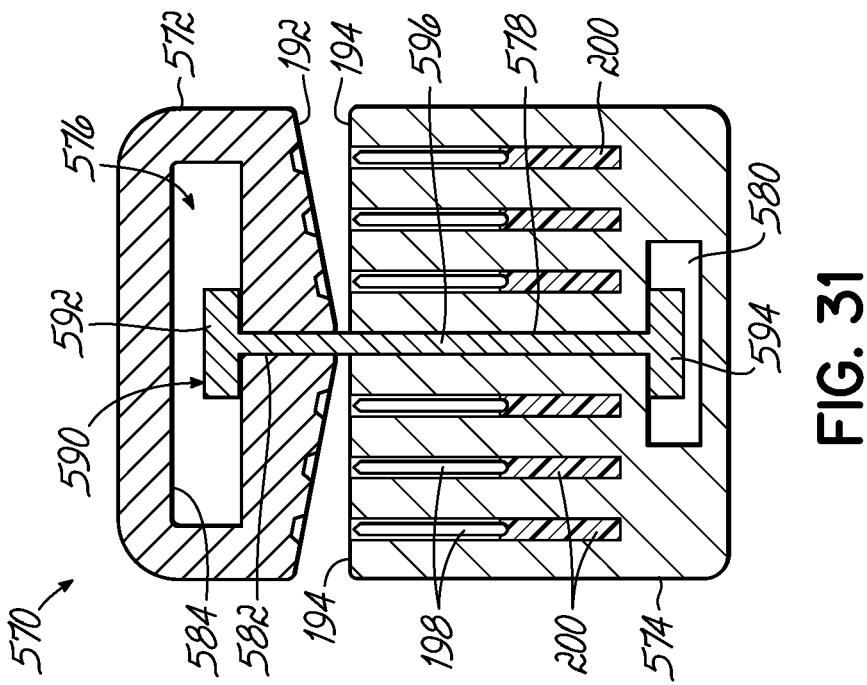

In the exemplary embodiment shown in FIG. 31, in which like reference numerals refer to like features throughout the figures, an end effector 570 includes an anvil 572, a cartridge 574, and an alignment mechanism 576 that aids in alignment of the anvil 572 with the cartridge 574 and further aids in providing uniform compression of the tissue between the anvil 572 and the cartridge 574. A guide slot 578 extends through the cartridge 574 and opens to the cartridge face 194. A guide channel 580 extends axially through the cartridge 574. The guide slot 578 opens to the guide channel 580. The anvil 572 includes a guide slot 582 that opens to an anvil guide channel 584 and opens to the face 192.

In one embodiment, the alignment mechanism 576 includes a knife 590 that has an I-shaped cross sectional configuration, much like an I-beam. The knife 590 has a top flange 592, a bottom flange 594, and a web 596 connecting the top flange 592 to the bottom flange 594. The top flange 592 slidably engages the guide channel 580 of the anvil 572 and the bottom flange 594 slidably engages the guide channel 580 of the cartridge 574. This configuration improves the rigidity of the end effector 570 during stapling/cutting. The I-beam configuration may substantially prevent any torque produced by the stapling/cutting action from twisting the anvil 572 relative to the cartridge 574 as can be appreciated by the cross-section shown in FIG. 31 in which the knife 590 is shown to positively lock the anvil 572 relative to the cartridge 574 and thereby prevent their separation and relative side-to-side motion during cutting/stapling. Other configurations are possible.

Figure 32:
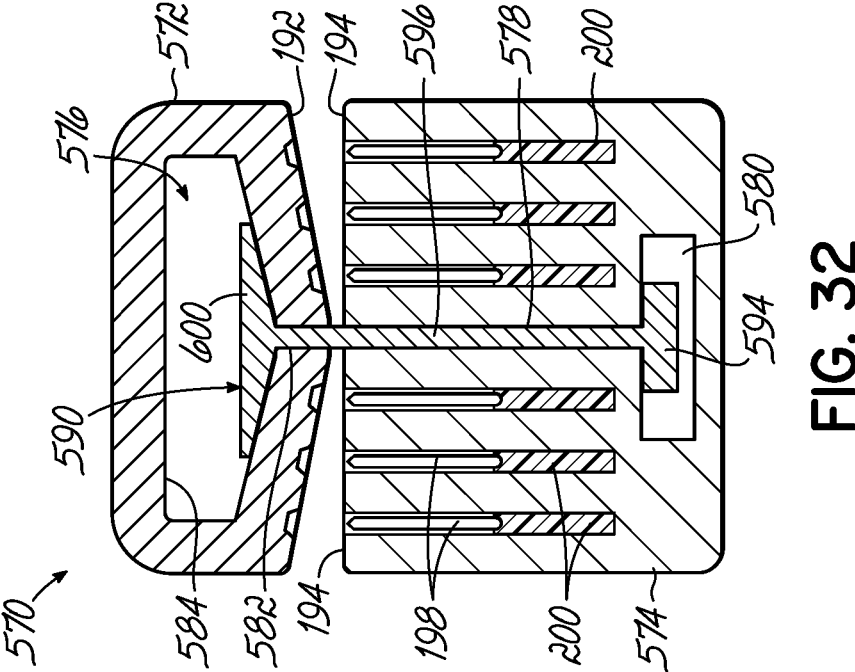
FIGS. 31 and 32 are cross-sectional views of end effectors according to embodiments of the present invention.

In an alternate embodiment, and with reference to FIG. 32, the knife 590 may have a Y-shaped top flange 600. In this embodiment where the anvil face 192 is not parallel to the cartridge face 194 in the transverse direction, the Y-shaped top flange 600 may provide improved alignment within a complimentarily shaped guide channel 584. Alignment mechanisms are further described further described in the commonly-owned International Application No. PCT/US2015/022904, which is incorporated by reference herein in its entirety.

When the anatomical structure is being compressed by the anvil and the cartridge, the compression should be great enough to stop the flow of blood to the area to be stapled and/or cut. At the same time, the anatomical structure should be compressed to create a desired gap between the anvil and the cartridge to achieve a B-shaped staple configuration along the staple line 12. Once a staple is formed in the B-shaped configuration, the configuration resists changes to the formed height. Accordingly, it is important to provide sufficient compression along the length of the end effector, which becomes more challenging as the length of the end effector increases. Conventional end effectors do not address the issue of providing sufficient compression along an end effector where the tissue thickness varies over the length of the anatomical structure being stapled while also providing the desired gap for achieving a B-shaped staple.

Figure 33:
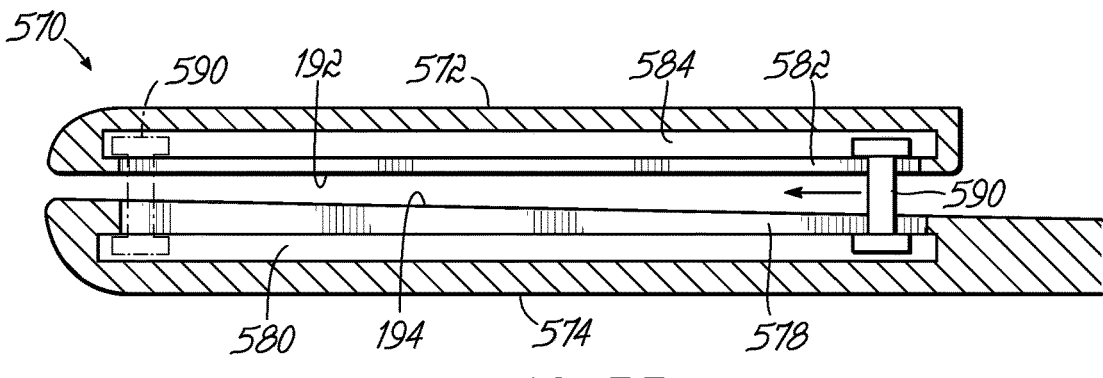
FIGS. 33-36 are elevation views of end effectors according to various embodiments of the present invention.

In one embodiment, and with reference now to FIGS. 33-36, the changing gap between the anvil and the cartridge, as is described above in for example FIG. 11, may affect the track defined by the guide channels 580 and 584 of the alignment mechanism 576. In an aspect of the present invention, adjusting the configuration of the anvil face and/or the cartridge face to compensate for the decrease in tissue thickness from the antrum 24 to the fundus 26 may allow for uniform compression and B-shaped staple formation along the length of the end effector. In FIG. 33, the cartridge face 194 is not parallel to the anvil face 192. However, the guide channel 584 is parallel to the anvil face 192. The orientation of the guide channel 580 may be angled to extend through the cartridge 574 at an angle that is nearly equivalent to but oppositely oriented from the angle between the cartridge face 194 and the anvil face 192. With this configuration, the track of the knife 590 is the same along the end effector 570. The gap between the anvil 572 and the cartridge 574 changes as described above with reference to FIG. 11. In this regard, the angled cartridge face 194 may compensate for the angled thickness of the stomach 10 while sufficient compression and B-shaped staple formation is maintained along the length of the end effector 570. The cartridge 574 may be a unitary body, the angled cartridge face 194 being an integral part of the unitary body. Alternatively, a separate element (e.g., a shim) may be coupled to the cartridge 574 to result in the angled configuration.

Figure 34:
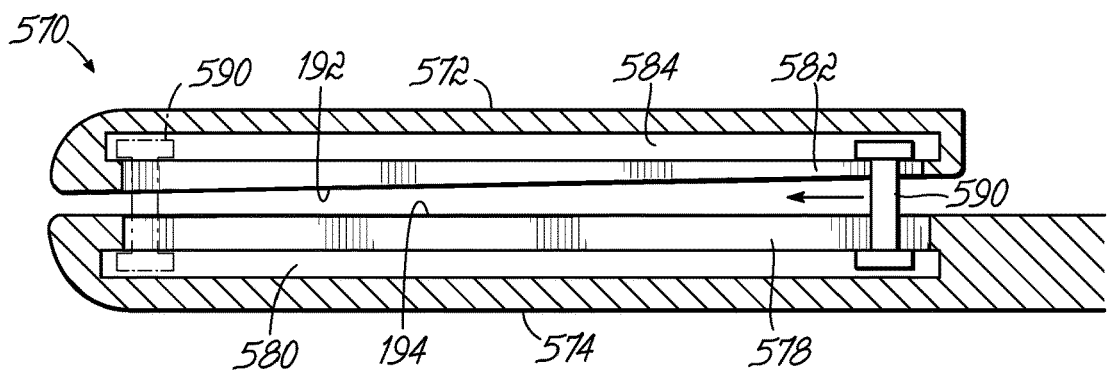

In one embodiment, and with reference to FIG. 34, in which like reference numerals refer to like elements throughout the figures, the anvil face 192 is angled relative to the cartridge face 194, while the guide channel 584 of the anvil 572 is generally parallel to the cartridge face 194. As shown, the guide channel 584 is oriented at an angle relative to the anvil face 192 so that the track for the knife 590 is constant. In this regard, the angled anvil face 192 may compensate for the angled thickness of the stomach 10 while sufficient compression is maintained along the length of the end effector 570. The anvil 572 may be a unitary body, the angled anvil face 192 being an integral part of the unitary body. Alternatively, a separate element (e.g., a shim) may be coupled to the anvil 572 to result in the angled configuration.

Figure 35:
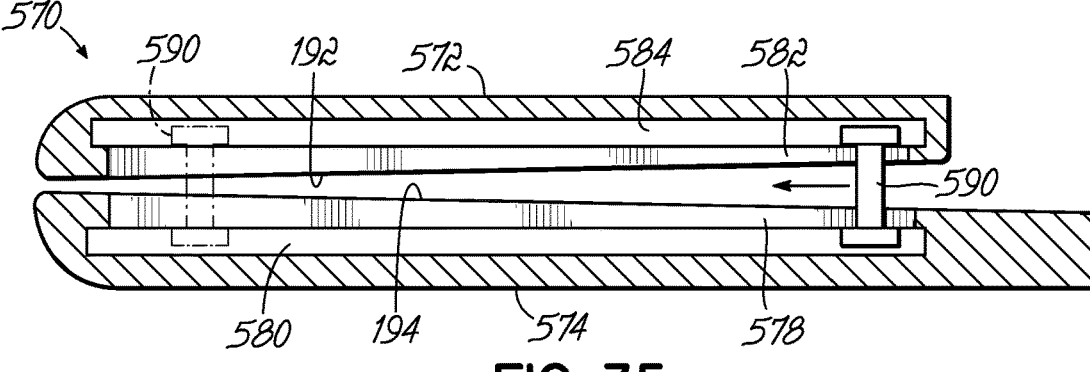
Figure 36:
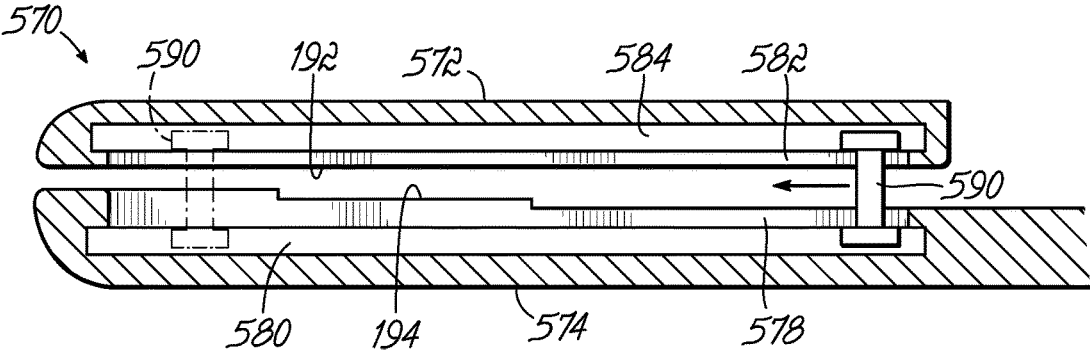

In one embodiment, and with reference to FIG. 35, in which like reference numerals refer to like elements throughout the figures, the guide channels 580 and 584 are parallel to each other but are each angled relative to the faces 192, 194. In FIG. 36, the cartridge face 194 includes a stepped configuration similar to the shown in, for example, FIG. 15A. The guide channels 580 and 584 are parallel to one another. In this regard, the stepped configuration of the cartridge face 194 may compensate for the angled thickness of the stomach 10 while sufficient compression and B-shaped staple formation is maintained along the length of the end effector 570. The cartridge 574 may be a unitary body, the stepped cartridge face 194 being an integral part of the unitary body. Alternatively, a separate element (e.g., a shim) may be coupled to the cartridge 574 to result in the stepped configuration.

FIGS. 37A-40B each illustrate shapes of staples 198 and shapes of staple pockets 190. In FIGS. 37A and 37B, a B-shaped staple is shown. To shape the staples 198 into a conventional B shape, the tips of the staple legs may be bent past the crown. It will be appreciated that this shape may result from deformation caused by forcing a staple 198 into the staple pockets 190 shown in FIGS. 39A and 39B. Staple pockets include paired staple leg receiving cups that are mirror images in the anvil face. In FIGS. 38A and 38B, a "2-D"-shaped staple 198 is shown. This 2-D configuration may be advantageous where staples 198 having the same open leg length are configured to have different closed leg lengths. This configuration may be produced with the staple pocket 190 shown in FIGS. 40A and 40B. If the tips of the staple legs are bent so that they extend past the crown, there is a possibility the tips may snag or puncture tissue near the stomach. To prevent this, the staple pockets 190 can be configured to allow for the arc segment of the bent staple legs to have a wider radius. More specifically, the longitudinal portion of the staple pockets 190 is created by two intersecting arcs. The first arc has a radius of about 0.040 inch to about 0.060 inch that is cut to a depth of 0.010 inch to 0.030 inch. A second arc is has a radius of about 0.030 inch to about 0.050 inch. At the center of the staple pockets 190, the first and second arcs intersect. The distance between the two paired cups is from about one times the radius of the staple wire to about two times the radius of the stapler wire. The transverse shape of the 2-D pocket is created by parabolic arcs that intersect with the longitudinal arcs to create a rectangular shaped cut into the surface of the pocket. The rectangular-shaped cut is about four times to about six times the diameter of the staple wire and the length is about half of the radius to about one times the radius of the span of the crown of the staple. Pocket shapes according to embodiments of the present invention may be sized for staples having any crown length, wire diameter, and leg length. In this manner, the bent tips will not cross the midline of the crowns of the staples 198. In one embodiment, and with reference to FIGS. 38A and 38B where there is a gap increase between the anvil and the cartridge in the transverse plane (transverse to the longitudinal direction), both of the leading (distal) and lagging (proximal) staple legs will be deflected to the same side of the crown (shown in FIG. 38B). Consequently, the legs of the staples 198 may cross.

In embodiments of the end effector, where there is a gap increase between the anvil and the cartridge, for example, like that shown in FIG. 11, the leading leg of each staple 198 will contact the leading pocket and begin bending before the lagging leg contacts the lagging pocket when the surgeon fires the stapling mechanism. With reference to FIGS. 39A-40B, the staple pockets 190 may be configured to bend the leading leg so that it is out of the way of the lagging leg when the lagging leg crosses the leading leg. In this manner, the trajectory of the bent second leg is not interrupted by collision with the already bent leading leg. Those of ordinary skill in the art will recognize that other alternative arrangements may also be possible to prevent the tips of the staple legs from crossing below the staple crowns.

Figure 41:
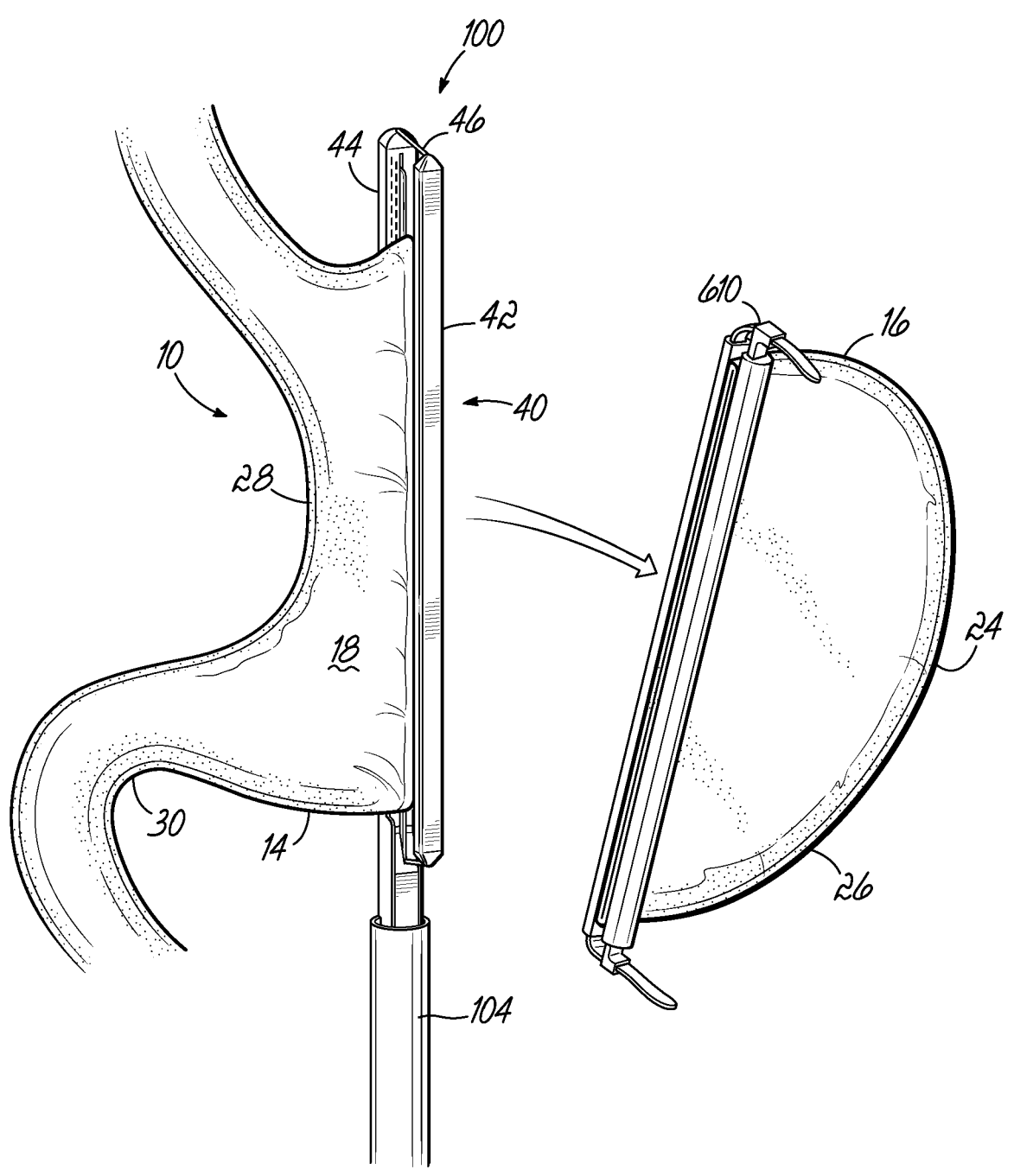
FIG. 41 is an elevation view of one embodiment of the present invention following resection of a stomach.

As discussed above, the portion of the stomach being resected is often stapled along with the stomach sleeve to prevent undesirable leakage of contents therefrom. With reference to FIG. 41, an exemplary embodiment includes the endocutter stapling device 100 described above with reference to FIG. 3 and a clamp 610. Before actuation of the endocutter stapling device 100, the clamp 610 may be clamped onto the tissue adjacent the endocutter stapling device 100 that will be excised after the staple line is complete. In other words, the clamp 610 may be to the anatomical left of the endocutter stapling device 100. With this configuration, stapling the to-be-excised portion of the stomach 10 would not be necessary due to the compression provided by the clamp 610. In this regard, the endocutter stapling device 100 may be configured to only staple the tissue that will become the stomach sleeve. The clamping force provided by the clamp 610 may supplement the clamping force provided by the endocutter stapling device 100. This additional compression near the cut line may result in an improved staple line. After the staple line is complete, the excised portion would still be clamped by the clamp 610, as shown in FIG. 41.

Figure 42:
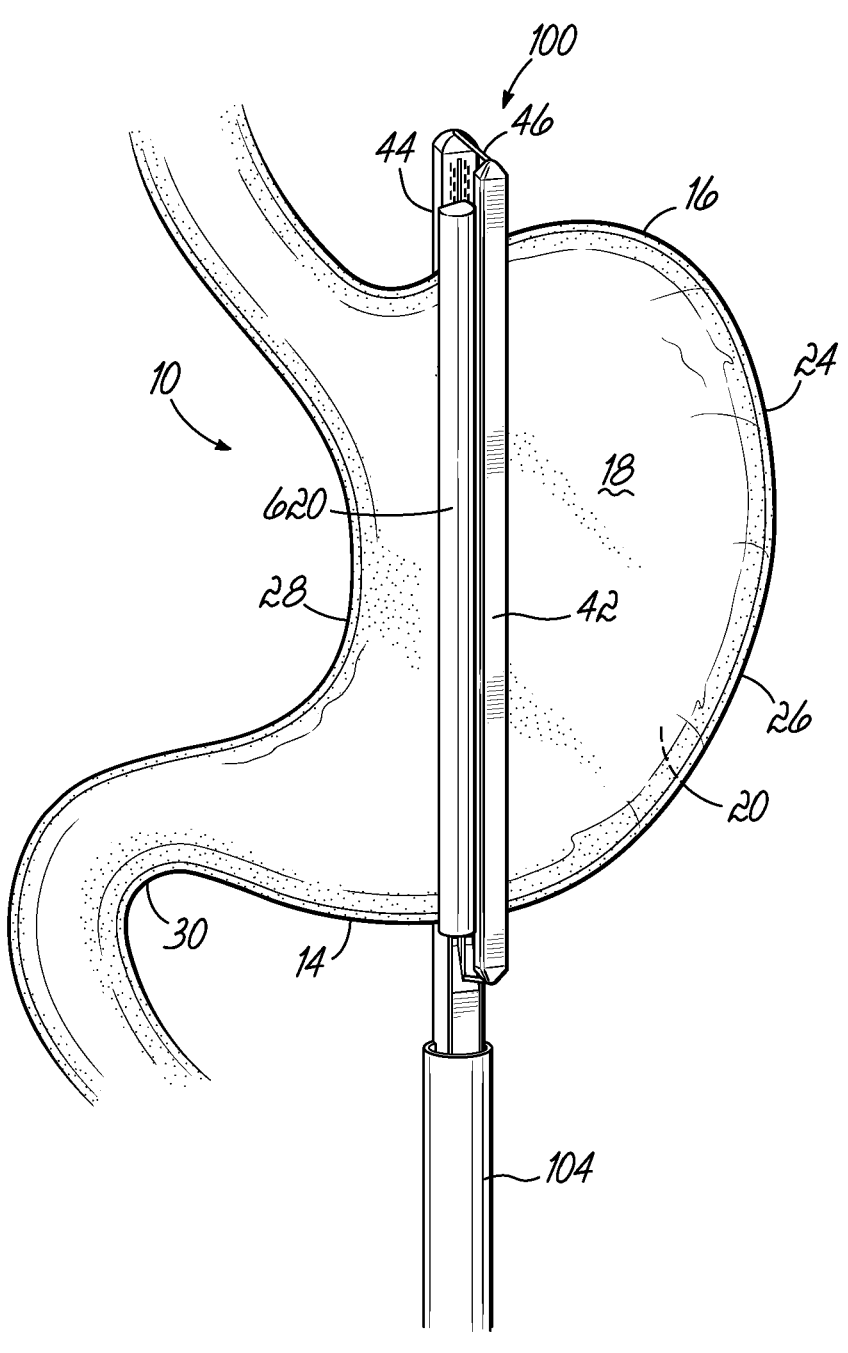
FIG. 42 is a perspective view of an end effector according to one embodiment of the invention positioned on a stomach.

In one embodiment of the present invention, with reference to FIG. 42, a spacer 620 may be coupled to the anvil 42 of the endocutter stapling device 100. The spacer may have a width of, for example, about 1 cm. The staple line 12 is frequently 1 cm away from the gastro esophageal junction 22, and using the spacer 620 to space the endocutter stapling device 100 apart from the gastro esophageal junction 22 would assure a proper spacing from this anatomical landmark. Properly spacing the endocutter stapling device 100 from the gastro esophageal junction 22 ensures that staples are not formed on a part of the esophagus. While the spacer 620 is specifically shown as being coupled to the anvil 42, it would be readily appreciated that in alternate embodiments, the spacer 620 may alternatively or additionally be coupled to the cartridge 44.

While the present invention has been illustrated by a description of various preferred embodiments and while these embodiments have been described in some detail, it is not the intention of the inventor to restrict or in any way limit the scope of the appended claims to such detail. Further, it should be recognized that the spacing and scale of certain elements depicted in the Figures may be exaggerated to aid in the understanding of the present invention. Consequently, the Figures may be seen as schematic representations rather than exact representations of embodiments. Though the embodiments described herein were primarily directed to a stapler, it is clear that many of the aspects of the present invention may be utilized with additional devices. By way of example, the embodiments described herein may operate as a surgical clamp or a stabilizing device independent of the aspects of the present invention that allow the embodiments to act as a stapler. Additional advantages and modifications will readily appear to those skilled in the art. The various features of the invention may be used alone or in any combination depending on the needs and preferences of the user.

What is claimed is:

1. An end effector for stapling and cutting an anatomical structure, the end effector comprising:
   (a) an anvil, the anvil comprising;
      (i) a first anvil end, a second anvil end, and an anvil face; and
   (b) a cartridge having a first cartridge end, a second cartridge end, and a cartridge face defining a cartridge blade channel, the cartridge being configured to retain a plurality of staples, wherein the first anvil end is coupled with the first cartridge end at a distal portion of the end effector and the second anvil end is coupled with the second cartridge end at a proximal portion of the end effector, wherein each of the plurality of staples comprises a first staple leg having a first tip, a second staple leg having a second tip, and a crown connecting the first staple leg and the second staple leg and having a midpoint, wherein actuating the end effector moves each of the plurality of staples from;
      (i) an open staple configuration wherein the first staple leg and the second staple leg are generally perpendicular to a longitudinal axis of the crown;
      (ii) a closed staple configuration wherein a first portion of the first staple leg and a second portion of the second staple leg overlap and cross the midpoint of the crown, and wherein the first tip and the second tip remain above and to a same side of the crown; and
   (c) a blade that is movable from a first position at the first anvil end to a second position at the second anvil end.

2. The end effector of claim 1, wherein the end effector has a first end and a second end, the end effector further comprising a staple driver ramp operably configured to urge the plurality of staples from the cartridge towards the anvil face, wherein the staple driver ramp is movable from the second end of the end effector to the first end of the end effector such that the end effector is operably configured to deploy the plurality of staples from the cartridge as the blade is moved from the second end to the first end.

3. The end effector of claim 1, wherein a portion of the anvil face is angled relative to a portion of the cartridge face.

4. The end effector of claim 1, wherein the anvil face comprises a stepped configuration having a first segment and a second segment that are offset each reside in different planes.

5. The end effector of claim 1, wherein the first staple leg and the second staple leg of at least one of the plurality of staples have different lengths.

6. The end effector of claim 1, further comprising a plurality of staple pockets, wherein at least one of the plurality of staple pockets comprises a first cup and a second cup for staple formation, the first cup and the second cup having different configurations.

7. The end effector of claim 6, wherein the first cup has a first arc with a first radius of from 0.040 inches to 0.060 inches and a first depth of from 0.010 inches to 0.030 inches, and the second cup has a second arc with a second radius of from 0.030 inches to 0.050 inches and a second depth of from 0.010 to 0.030 inches.

8. An end effector for stapling and cutting an anatomical structure, the end effector comprising:
(a) an anvil, the anvil comprising;
    (i) a first anvil end, a second anvil end, and an anvil face; and
(b) a cartridge having a first cartridge end, a second cartridge end, and a cartridge face defining a cartridge blade channel, the cartridge being configured to retain a plurality of staples, wherein the first anvil end is coupled with the first cartridge end at a distal portion of the end effector and the second anvil end is coupled with the second cartridge end at a proximal portion of the end effector, wherein each of the plurality of staples comprises a first staple leg having a first tip, a second staple leg having a second tip, and a crown connecting the first staple leg and the second staple leg and having a midpoint, wherein actuating the end effector moves each of the plurality of staples from;
    (i) an open staple configuration wherein the first staple leg and the second staple leg are generally perpendicular to a longitudinal axis of the crown;
    (ii) a closed staple configuration wherein the first staple leg and the second staple leg lie in different planes and a first portion of the first staple leg and a second portion of the second staple leg overlap and cross the midpoint of the crown, and wherein the first tip and the second tip remain above and to a same side of the crown; and
(c) a blade that is movable from a first position at the first anvil end to a second position at the second anvil end.

9. The end effector of claim 8, further comprising a plurality of staple pockets, wherein a pocket shape of each of the plurality of staple pockets is configured to shape one of the plurality of staples to be in the closed staple configuration.

10. The end effector of claim 9, wherein the end effector has a first end and a second end, the end effector further comprising a staple driver ramp operably configured to urge the plurality of staples from the cartridge towards the anvil face, wherein the staple driver ramp is movable from the second end of the end effector to the first end of the end effector such that the end effector is operably configured to deploy the plurality of staples from the cartridge as the blade is moved from the second end to the first end.

11. The end effector of claim 8, wherein at least one of the plurality of staple pockets comprises a first cup and a second cup for staple formation, the first cup and the second cup having different configurations.

12. The end effector of claim 11, wherein the first cup has a first arc with a first radius of from 0.040 inches to 0.060 inches and a first depth of from 0.010 inches to 0.030 inches, and the second cup has a second arc with a second radius of from 0.030 inches to 0.050 inches and a second depth of from 0.010 to 0.030 inches.

13. The end effector of claim 8, wherein a portion of the anvil face is angled relative to a portion of the cartridge face.

14. The end effector of claim 8, wherein the anvil face comprises a stepped configuration having a first segment and a second segment that each reside in different planes.

15. The end effector of claim 8, wherein the first staple leg and the second staple leg of at least one of the plurality of staples have different lengths.

16. An end effector for stapling and cutting an anatomical structure, the end effector comprising:
(a) an anvil, the anvil comprising;
    (i) a first anvil end, a second anvil end, and an anvil face; and
(b) a cartridge having a first cartridge end, a second cartridge end, and a cartridge face defining a cartridge blade channel, the cartridge being configured to retain a plurality of staples, wherein the first anvil end is coupled with the first cartridge end at a distal portion of the end effector and the second anvil end is coupled with the second cartridge end at a proximal portion of the end effector, wherein each of the plurality of staples comprises a first staple leg having a first tip, a second staple leg having a second tip, and a crown connecting the first staple leg and the second staple leg and having a midpoint, wherein actuating the end effector moves each of the plurality of staples from;
    (i) an open staple configuration wherein the first staple leg and the second staple leg are generally perpendicular to a longitudinal axis of the crown;
    (ii) a closed staple configuration wherein a first portion of the first staple leg and a second portion of the second staple leg are separated from the midpoint of the crown, and wherein the first tip and the second tip remain above the crown; and
(c) a blade that is movable from a first position at the first anvil end to a second position at the second anvil end.

17. The end effector of claim 16, further comprising a plurality of staple pockets, wherein a pocket shape of each of the plurality of staple pockets is configured to shape one of the plurality of staples to be in the closed staple configuration and, along a length of the anvil, the first leg angle and the second leg angle of the plurality of staples vary.

18. The end effector of claim 17, wherein the plurality of staple pockets are arranged in rows, a pocket shape of each of the plurality of staple pockets is configured to shape one of the plurality of staples to be in the closed staple configuration, and the first leg angle and the second leg angle of the plurality of staples in adjacent rows vary.

19. The end effector of claim 17, wherein at least one of the plurality of staple pockets comprises a first cup and a second cup for staple formation, the first cup and the second cup having different configurations.

20. The end effector of claim 19, wherein the first cup has a first arc with a first radius of from 0.040 inches to 0.060 inches and a first depth of from 0.010 inches to 0.030 inches, and the second cup has a second arc with a second radius of from 0.030 inches to 0.050 inches and a second depth of from 0.010 to 0.030 inches.

21. The end effector of claim 16, wherein the end effector has a first end and a second end, the end effector further comprising a staple driver ramp operably configured to urge the plurality of staples from the cartridge towards the anvil face, wherein the staple driver ramp is movable from the second end of the end effector to the first end of the end effector such that the end effector is operably configured to deploy the plurality of staples from the cartridge as the blade is moved from the second end to the first end.

22. The end effector of claim 16, wherein a portion of the anvil face is angled relative to a portion of the cartridge face.

23. The end effector of claim 16, wherein the anvil face comprises a stepped configuration having a first segment and a second segment that each reside in different planes.

24. The end effector of claim 16, wherein the first staple leg and the second staple leg of at least one of the plurality of staples have different lengths.

* * * * *